US008877211B2

(12) United States Patent
Chowdhury et al.

(10) Patent No.: US 8,877,211 B2
(45) Date of Patent: Nov. 4, 2014

(54) BOVINE HERPES VIRUS VACCINE WITH MULTIPLE MUTATIONS

(75) Inventors: Shafiqul I. Chowdhury, Baton Rouge, LA (US); Hui Yong Wei, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 13/325,182

(22) Filed: Dec. 14, 2011

(65) Prior Publication Data

US 2013/0034585 A1 Feb. 7, 2013

Related U.S. Application Data

(60) Provisional application No. 61/501,545, filed on Jun. 27, 2011.

(51) Int. Cl.
| | | |
|---|---|---|
| *A61K 39/245* | (2006.01) | |
| *C12N 15/63* | (2006.01) | |
| *C12N 7/01* | (2006.01) | |
| *A61P 31/22* | (2006.01) | |
| *C12N 7/00* | (2006.01) | |
| *A61K 39/00* | (2006.01) | |

(52) U.S. Cl.
CPC ....... *A61K 39/245* (2013.01); *A61K 2039/5254* (2013.01); *A61K 2039/552* (2013.01); *C12N 2710/16771* (2013.01); *C12N 2710/16734* (2013.01); *C12N 7/00* (2013.01); *C12N 2710/16762* (2013.01)
USPC .................. 424/229.1; 424/204.1; 424/230.1; 424/231.1; 424/205.1; 435/235.1; 435/320.1

(58) Field of Classification Search
CPC ............... A61K 39/12; A61K 39/245; A61K 2039/5252; A61K 2039/521; A61K 2039/51; A61K 2039/522; A61K 2039/525; A61K 38/162; A61K 39/00; A61K 2039/55516; A61K 2039/5254; A61K 2039/53; C07K 14/005; C07K 16/081; C07K 16/087; C12N 15/86; C12N 2710/16122; C12N 2710/16422
See application file for complete search history.

(56) References Cited

U.S. PATENT DOCUMENTS

| | | | |
|---|---|---|---|
| 5,151,267 A | 9/1992 | Babiuk et al. ................. 424/89 |
| 5,676,951 A | 10/1997 | Rusewijk et al. .......... 424/229.1 |
| 6,086,902 A | 7/2000 | Zamb et al. ................ 424/204.1 |
| 6,284,251 B1 | 9/2001 | Chowdhury ............... 424/199.1 |
| 6,403,097 B1 | 6/2002 | Rusewijk et al. .......... 424/199.1 |
| 8,637,046 B2 * | 1/2014 | Osterrieder et al. ....... 424/201.1 |

FOREIGN PATENT DOCUMENTS

WO WO2010039934 A1 * 4/2010

OTHER PUBLICATIONS

Brideau et al. Directional transneuronal infection by pseudorabies virus is dependent on an acidic internalization motif in the Us9 cytoplasmic tail. Journal of Virology, 2000, vol. 74, p. 4549-4561.*
Al-Mubarak, A. et al., "A glycine-rich bovine herpesvirus 5 (BHV-5) gE-specific epitope within the ectodomain is important for BHV-5 neurovirulence," J Virol, vol. 78, No. 9, pp. 4806-4816 (2004).
Brun, Mario CS et al., "Bovine herpesvirus type 1 (BoHV-1) anterograde neuronal transport from trigeminal ganglia to nose and eye requires glycoprotein E," J. NeuroVir., iFirst, pp. 1-6 (2009).
Butchi, N.B. et al., "Envelope protein Us9 is required for the anterograde transport of bovine herpesvirus type 1 from trigeminal ganglia to nose and eye upon reactivation," J Neurovirol., vol. 3, pp. 384-388 (2007).
Chowdhury, S.I. et al., "A Bovine Herpesvirus Type 1 (BHV-1) mutant virus with truncated glycoprotein E cytoplasmic tail has defective anterograde neuronal transport in rabbit dorsal root ganglionic primary neuronal cultures in a microfluidic chamber system," J. Neurovirol, vol. 16, pp. 457-465 (2010).
Chowdhury, S.I. et al., "Bovine herpesvirus 5 glycoprotein E is important for neuroinvasiveness and neurovirulence in the olfactory pathway of the rabbit," J Virol, vol. 74, No. 5, pp. 2094-2106 (2000).
Chowdhury, S.I., "Construction and characterization of an attenuated bovine herpesvirus type 1 (BHV-1) recombinant virus," Vet Microbiol, vol. 52, Nos. 1-2, pp. 13-23 (1996).
Chowdhury, S.I., et al., "Construction and characterization of a glycoprotein E gene-deleted bovine herpesvirus type 1 recombinant," Am J Vet Res, vol. 60, No. 2, pp. 227-232 (1999).
Chowdhury, S.I. et al., "The bovine hervesvirus type 1 envelope protein Us9 acidic domain is crucial for anterograde axonal transport," Vet. Microbiol., epub ahead of print (May 13, 2011).
Chowdhury, S.I. et al., "The Us9 gene of bovine herpesvirus 1 (BHV-1) effectively complements a Us9-null strain of BHV-5 for anterograde transport, neurovirulence, and neuroinvasiveness in a rabbit model," J Virol, vol. 80, No. 9, pp. 4396-4405 (2006).
Ellis, J.A., "Update on viral pathogenesis in BRD," Anim Health Res Rev, vol. 10, No. 2, pp. 149-153 (2009).

(Continued)

*Primary Examiner* — Benjamin P Blumel
*Assistant Examiner* — Rachel Gill
(74) *Attorney, Agent, or Firm* — Bonnie J. Davis; John H. Runnels

(57) ABSTRACT

A BHV-1 mutant virus has been made that incorporates into a single virus two or more deletions in one or more of three genes—glycoprotein N, glycoprotein E and Us9. Specifically, a BHV-1 $U_L49.5\Delta30\text{-}32$ CT-null virus was made and tested. This mutant virus was then used to incorporate additional changes, e.g., the glycoprotein E cytoplasmic-tail deletion, the Us9 deletion, or both. This triple mutant BHV-1 $U_L49.5\Delta30\text{-}32$ CT-null/gE CTΔ/Us9Δ virus will be superior to the current BHV-1 mutants because the mutant virus will not be shed following reactivation, will be a DIVA based on gE CT-specific serum antibodies, and will induce better protective response by inducing higher SN titers and better cellular immune response. This new virus will have sufficient viral replication in the nasal epithelium and will be a good vaccine for protection of cattle from BHV-1. The new mutant viruses can also be used as vectors for exogenous genes.

11 Claims, 32 Drawing Sheets

(56) References Cited

OTHER PUBLICATIONS

Gopinath, R.S. et al., "Effects of virion host shut-off activity of bovine herpesvirus 1 on MHC class I expression," Viral Immunol, vol. 14, No. 4, pp. 595-608 (2002).
Harland, R.J. et al., "The effect of subunit or modified live bovine herpesvirus-1 vaccines on the efficacy of a recombinant *Pasteurella haemolytica* vaccine for the prevention of respiratory disease in feedlot calves," Can Vet J, vol. 33, No. 11, pp. 734-741 (1992).
Hewitt, E.W., "The MHC class I antigen presentation pathway: strategies for viral immune evasion," Immunology, vol. 110, No. 2, pp. 163-169 (2003).
Hinkley, S. et al., "Bovine herpesvirus-1 infection affects the peptide transport activity in bovine cells," Virus Res, vol. 53, No. 1, pp. 91-96 (1998).
Hutchings, D.L. et al., "Lymphocyte proliferative responses to separated bovine herpesvirus 1 proteins in immune cattle," J. Virol., vol. 64, pp. 5114-5122 (1990).
Jones, C. et al., "A review of the biology of bovine herpesvirus type 1 (BHV-1), its role as a cofactor in the bovine respiratory disease complex and development of improved vaccines," Anim Health Res Rev, vol. 8, No. 2, pp. 187-205 (2007).
Jons, A. et al., "Glycoproteins M and N of pseudorabies virus form a disulfide-linked complex," J Virol, vol. 72, No. 1, pp. 550-557 (1998).
Kaashoek, M.J. et al., "Virulence, immunogenicity and reactivation of bovine herpesvirus 1 mutants with a deletion in the gC, gG, gI, gE, or in both the gI and gE gene," Vaccine, vol. 16, pp. 802-809 (1998).
Kaashoek, M.J. et al., "Virulence, immunogenicity and reactivation of seven bovine herpesvirus 1.1 strains: clinical and virological aspects," Vet Rec, vol. 139, No. 17, pp. 416-421 (1996).
Kaashoek, M.J. et al., "Virulence and immunogenicity in calves of thymidine kinase- and glycoprotein E-negative bovine herpesvirus 1 mutants," Vet Microbiol, vol. 48, pp. 143-153 (1996).
Knittler, M.R., et al., "Nucleotide binding by TAP mediates association with peptide and release of assembled MHC class I molecules," Curr Biol, vol. 9, No. 18, pp. 999-1008 (1999).
Konig, P. et al., "Glycoprotein M of bovine herpesvirus 1 (BHV-1) is nonessential for replication in cell culture and is involved in inhibition of bovine respiratory syncytial virus F protein induced syncytium formation in recombinant BHV-1 infected cells," Vet Microbiol, vol. 86, Nos. 1-2, pp. 37-49 (2002).
Koppers-Lalic, D. et al., "The UL41-encoded virion host shutoff (vhs) protein and vhs-independent mechanisms are responsible for down-regulation of MHC class I molecules by bovine herpesvirus 1," J Gen Virol, vol. 82, Pt 9, pp. 2071-2081 (2001).
Koppers-Lalic, D. et al., "Varicellovirus UL 49.5 proteins differentially affect the function of the transporter associated with antigen processing, TAP," PLoS Pathog, vol. 5, No. 5, pp. e1000080 (2008).
Koppers-Lalic, D. et al., "Varicelloviruses avoid T cell recognition by UL49.5-mediated inactivation of the transporter associated with antigen processing," Proc Natl Acad Sci USA, vol. 102, No. 14, pp. 5144-5149 (2005).
Liang, X. et al., "Bovine herpesvirus 1 UL49.5 homolog gene encodes a novel viral envelope protein that forms a disulfide-linked complex with a second virion structural protein," J Virol, vol. 70, No. 3, pp. 1448-1454 (1996).
Lipinska, A.D. et al., "Bovine herpesvirus 1 UL49.5 protein inhibits the transporter associated with antigen processing despite complex formation with glycoprotein," M. J Virol, vol. 80, No. 12, pp. 5822-5832 (2006).
Liu, Z.F. et al., "A bovine herpesvirus type 1 mutant virus specifying a carboxyl-terminal truncation of glycoprotein E is defective in anterograde neuronal transport in rabbits and calves," J Virol, vol. 82, No. 15, pp. 7432-7442 (2008).
Loch, S. et al., "Signaling of a varicelloviral factor across the endoplasmic reticulum membrane induces destruction of the peptide-loading complex and immune evasion," J Biol Chem, vol. 283, No. 19, pp. 13428-13436 (2008).

Mars, M.H. et al., "Efficacy of a live glycoprotein E-negative bovine herpesvirus 1 vaccine in cattle in the field," Vaccine, vol. 19, pp. 1924-1930 (2001).
Muylkens, B. et al., "Intraspecific bovine herpesvirus 1 recombinants carrying glycoprotein E deletion as a vaccine marker are virulent in cattle," J Gen Virol., vol. 87, pp. 2149-2154 (2006).
Neefjes, J.J. et al., "Selective and ATP-dependent translocation of peptides by the MHC-encoded transporter," Science, vol. 261, No. 5122, pp. 769-771 (1993).
Rudolph, J. et al., "The gene 10 (UL49.5) product of equine herpesvirus 1 is necessary and sufficient for functional processing of glycoprotein M," J Virol, vol. 76, No. 6, pp. 2952-2963 (2002).
Smith, G.A. et al., "A self-recombining bacterial artificial chromosome and its application for analysis of herpesvirus pathogenesis," Proc Natl Acad Sci USA, vol. 97, No. 9, pp. 4873-4878 (2000).
Tikoo, S.K. et al., "Bovine herpesvirus 1 (BHV-1): biology, pathogenesis, and control," Adv Virus Res, vol. 45, pp. 191-223 (1995).
Tischer, B.K. et al., "Two-step red-mediated recombination for versatile high-efficiency markerless DNA manipulation in *Escherichia coli*," Biotechniques, vol. 40, No. 2, pp. 191-197 (2006).
van Drunen Littel-van den Hurk, S. et al., "Bovine herpesvirus-1 vaccines," Immunol Cell Biol, vol. 71, Pt 5, pp. 405-420 (1993).
van Drunen Littel-van den Hurk, W. et al., "Protective immunity in cattle following vaccination with conventional and marker bovine herpesvirus-1 (BHV1) vaccines," Vaccine, vol. 15, No. 1, pp. 36-44 (1997).
van Endert, P.M. et al., "Powering the peptide pump: TAP crosstalk with energetic nucleotides," Trends Biochem Sci, vol. 27, No. 9, pp. 454-461 (2002).
van Oirschot, J.T. et al., "Advances in the development and evaluation of bovine herpesvirus 1 vaccines," Vet Microbiol, vol. 52, Nos. 1-2, pp. 43-54 (1996).
Verweij, M.C. et al., "The varicellovirus UL49.5 protein blocks the transporter associated with antigen processing (TAP) by inhibiting essential conformational transitions in the 6+6 transmembrane TAP core complex," J Immunol, vol. 18, No. 7, pp. 4894-4907 (2008).
Wei, H. et al., "Bovine Herpesvirus Type 1 (BHV-1) Glycoprotein N Luminal Domain Residues 30 to 32 and Cytoplasmic Tail Residues Together Down Regulate MHC-I Efficiently: Lack of These Sequences Induce Better Protective Immune Responses in Calves," pp. 1-40 (accepted for publication Sep. 9, 2011).
Wei, H. et al., "Bovine herpesvirus type 1 (BHV-1) $U_L49.5$ luminal domain residues 30 to 32 are critical for MHC-1 down-regulation in virus-infected cells," PLoS ONE, vol. 6, No. 10, pp. e25742 (Oct. 26, 2011).
Wei, H. et al., "Coadministration of cidofovir and smallpox vaccine reduced vaccination side effects but interfered with vaccine-elicited immune responses and immunity to monkeypox," J Virol., vol. 83, pp. 1115-1125 (2009).
Wei, H. et al., "Definition of APC presentation of phosphoantigen (E)-4-hydroxy-3-methyl-but-2-enyl pyrophosphate to Vgamma2Vdelta 2 TCR," J Immunol, vol. 181, No. 7, pp. 4798-4806 (2008).
Wei, H. et al., "DR*W201/P65 tetramer visualization of epitope-specific CD4 T-cell during *M. tuberculosis* infection and its resting memory pool after BCG vaccination," PLoS One, vol. 4, No. 9, pp. e6905. (2009).
Whitbeck, J.C. et al., "Synthesis, processing, and oligomerization of the bovine herpes virus 1 gE and gI membrane proteins," J Virol., vol. 70, pp. 7878-7884 (1996).
Wu, S.X. et al., "Bovine herpesvirus 1 glycoprotein M forms a disulfide-linked heterodimer with the U(L)49.5 protein," J Virol, vol. 72, No. 4, pp. 3029-3036 (1998).
Yewdell, J.W. et al., "Making sense of mass destruction: quantitating MHC class I antigen presentation," Nat Rev Immunol, vol. 3, No. 12, pp. 952-961 (2003).

* cited by examiner

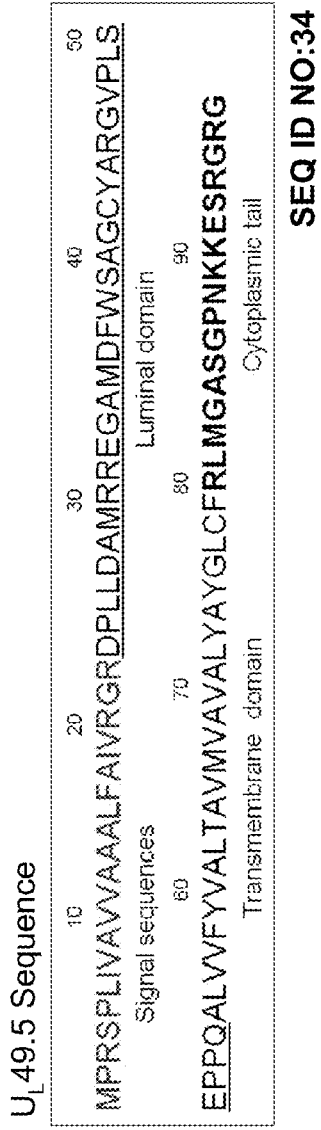

Wt U_L49.5 and U_L49.5 CT-null sequences

Atgccgcggtcgccgtcatcgttgcggttgtggccgccgcgctgtttgccatcgtgc
gcggccgcgacccctgctagacgcgatgcgggcgagggcaatggacttttg
gagcgcaggctgcgcgcggggtgccgctctcggagccaccgcgcaggccctg
gttgtttttacgtggccctgaccgcggtaatggtgccgtggccctgtacgcgtacg
ggcttgcttaggctcatgggcgccagcgggcccaataaaaaggagtcgcgggg 238      244 246 247
                      ↓        ↓  ↓  ↓
                              deletion  TAA gcggggctga

SEQ ID NO:37

Fig. 2

PCR primers for generating BHV-1 U$_L$49.5 CT-null mutant

SEQ ID NO:38 gtaatggtgcgcgtggccctgtacggcgtacggcgtcttgctttaGGCTCatgggcgccagcggccccaataaaaaggagtcgcgggggcggggc
V  M  V  A  V  L  Y  A  V  G  L  Q  F  R  L  M  G  A  S  G  P  N  K  E  S  R  G  R  G

SEQ ID NO:39

SEQ ID NO:2 pEPKan-s specific sequences
                                                                           aggatgacgacgataagtaggg
aatggtgcgtggccctgtACGGCGTACGGGCTTTGCTTT------taaGCGGCCAGCGGGCCCAATAAA
                      TGCGCATGCCCGAAACGAAA------attCGCGGTCGCCCGGGTTATTT
                                                                           ttcctcagcgccccgc
gattagtcttaaccaattaaccaac
pEPKan-s specific sequences

SEQ ID NO:3

Fig. 3

PCR primers for generating BHV-1 U$_L$49.5Δ30-32 CT-null mutant

SEQ ID NO:40

I V R G R D P L L D A M R R E G A M D F W
                                     30       32
                                    ↓         ↓
tgccatcgtgcgcggccgcgaccccctgctagacgcgatgCGGCGCGAGggggcaatggactttggag

SEQ ID NO:41    Forward primer

SEQ ID NO:4

5'    20bps                         Δ30-32                                                      20bps
tgccatcgtgcgcggccgcgACCCCCTGCTAGACGCGATG----------GGGGCAATGGACTTTTGGAG
TGGGGACGATCTGCGCTAC----------CCCCGTTACCTGAAAACCTC <u>aattagtcttaaccaattaaccaat</u>
5'
pEPKan-s specific sequences

SEQ ID NO:5

<u>aggatgacgacgataatagtagg</u>
pEPKan-s specific sequences
20bps
gggtcgacgatcgcgcgc-
20bps
Reverse primer

Fig. 4

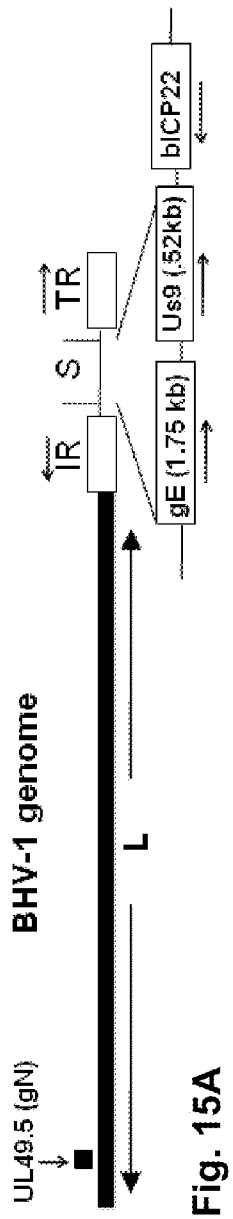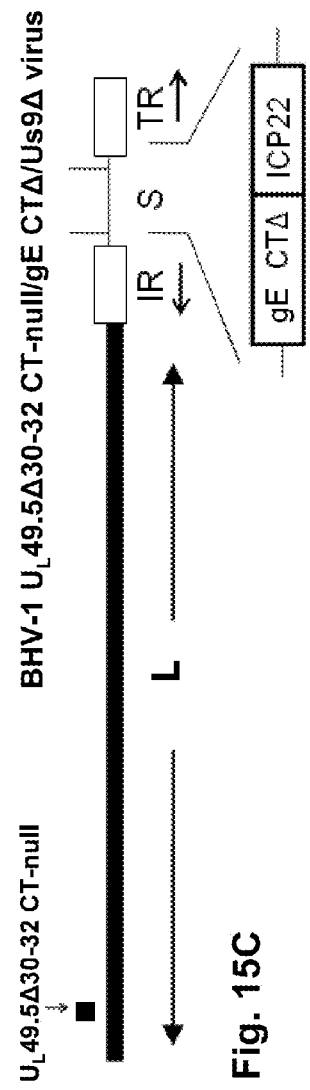
Fig. 15A
Fig. 15B
Fig. 15C

Construction of pBHV-1 gE CTΔ/Us9Δ deletion vector

U_L

```
Start gE →  atgcaaccca ccgcgccgcc ccggcggcgg ttgctgccgc tgctgctgcc gcagttattg    60
            cttttcgggc tgatggccga ggccaagccc gcgaccgaaa cccgggctc ggcttcggtc    120
            gacacggtct tcacgcgcg cgctggcgcg ccgtctttc tccagggcc cgcggcgcg     180
            ccggacgtgc gcgccgttcg cggctggagc gtcctcgcgg gcgcctgctc gccgcccgtg   240
            ccggagcccg tctgcctcga cgaccgcgag tgcttcaccg acgtggccct ggacgcggcc   300
            tgcctgcgaa ccgccgccgt ggcccgctg gcatcgcgg agctcgccga gcggccgac    360
            tcaacgggcg acaaagagtt tgttctcgcc gaccgcacg tctcggcgca gctgggtcgc   420
            aacgcgaccg gggtgctgat cgcggccgca gccgaggagg acggcggcgt gtacttcctg   480
            tacgaccggc tcatcggcga cgccggcgac gaggagacgc agttggcgct gacgctgcag   540
            gtcgacgcg ccggcgcgca gggcgccgcg cgggacgagg agagggaacc agcgaccggg   600
            cccacccgcg gccgccgcc ccaccgcacg acgacgcg cgccccgcg gcggcacggc      660
            gcgcgcttcc gcgtgctgcc gtaccactcc cacgtataca cccgggcga ttcctttctg   720
            ctatcggtgc gtctgcagtc tgagtttttc gacgaggctc ccttctcggc cagcatcgac   780
            tggtacttcc tgcggacggc cggcgactgc gcgctcatcc gcatatacga gacgtgcatc   840
            ttccaccccg aggcacggc ctgcctgcac cccgccgacg cgcagtgcag cttcgcgtcg   900
            ccgtaccgct ccgagaccgt gtacagcgg ctgtacgagc agtgccgccc ggaccctgcc    960
            ggtcgctgcc gcacgagtg cgagggcgcc gcgtacgcgg cgccgttgc gcacctgcgt   1020
            ccgccaata acagcgtaga cctggtctt gacgacgcgc cggctgcgc ctccgggctt    1080
            tacgtctttg tgctgcagta caacggccac gtggaagctt gggactacag cctagtcgtt   1140
            acttcggacc gtttggtgcg cgcggtcacc gaccacacgc gcccgaggc cgcagccgcc    1200
            gacgctccg agccaggcc accgctcacc agcgagccgg cgggcgcgcc cacccggccc   1260
            gcgcctggc ttgtggtgct ggtgggcgcg cttggactcg cgggactggt gggcatcgca   1320
                                           NT 1353 ———→ deletion
            gccctcgccg ttcgggtgtg cgcgcgcgc gcagcaga agcgcaccta cgacatcctc   1380
                                          arg ala ser
                                          (451) (452)
            aaccccttcg ggcccgtata caccagcttg ccgaccaacg agccgctcga cgtggtggtg   1440
            ccagttagcg acgacgaatt ttccctcgac gaagactctt tgcggatga cgacagcgac   1500
            gatgacgggc ccgctagcaa cccccctgcg gatgcctacg acctcgccgg cgccccagag   1560
            ccaactagcg ggtttgcgcg agccccgcc aacggcacg gtcgagtcg ctctgggttc   1620
            aaagtttggt ttaggacc gcttgaagac gatgccgcgc cagcgggac ccggccgca    1680
            ccagattaca ccgtggtagc agcgcgactc aagtccatcc tccgctaggc gcccccccc    1740
                                                       Stop gE →
            ccgcgcgctg tgccgtctga cggaaagcac ccgcgtgtag ggctgcatat aaatggagcg   1800
            ctcacacaaa gcctcgtgcg gctgcttcga aggcatggag agtccacgca gcgtcgtcaa   1860
                                               Start Us9 →
            cgaaaactat cgaggcgctg atgaggccga tgcagcgcc ccttcaccgc cgccggaagg   1920
            ctccatcgtg tccatcccca tcctcgagct caccatcgag gacgcgccgg ccagcgcaga   1980
Us9         agcaaccggc accgcggcag ccgcaccgg tgggcgcact ccagacgcga acgcagcacc    2040
            cggcggctac gtgccagttc ccgcggcgga tgtggactgc tattataccg aaagcgacag    2100
            cgagacggca ggcgagttt tgatacgcat gggcggcag cagcggcgc ggcatcggcg   2160
            gcgcgctgc atgatagcag cggccctgac ttgcattggc ctcgggccct gcgcggcgg    2220
            ggcagcggca ggcgccgtcc tggcgttgga ggtagtgccc cggccctgag gccccgagac   2280
                                                       Stop Us9 →
            ccccggccct gaggcctgg gcgggcc gactgtccc tccccctc ccccgtcc     2340
            gccgcgagt aaaggctgtc taatttttc cgcacgccg cgcctgtctt cttagggagg   2400
              Deletion ←—— NT 2358
            ggaaggaggg gagggaggggg aaggagggga gggaggggaa gggggagggg gaggggaagg   2460
            aggggaggga gggaaggag gggaggggagg ggaaggaggg gagggaggggg aaggagggga   2520
bICP22      gggaggggaa gggagggagg gagggggaagg aggggaggga ggggaaggag gggaggggagg   2580
            ggaaggaggg gaggggagggg aaggagggga gggaggggaa ggggggagag gggggccgcc    2640
            gaggattcgg gccggcgag cgagcgggcc aaagctcgg ctc                        2683
```

Fig. 18 gE ectodomain sequence

ACTGGTGGGCATCGCAGCCCTCGCCGTTCGGGTGTG
CGCGCGCCGCGCATAACTGACTAATAAAggtaccGTCT
arg Ala 451 stop stop stop - polyA KpnI bICP22
AATTTTTCCGCACGCCCGCGCCTGTCTTCTTAGGGA
GGGGAAGGAGGGGAGGGAGGGGAAGGAGGGGAGG
GAGGGGAAGGAGGGGAGGGAGGGGAAGGAGGGGA
TTCGGGCCGGCCGAGGATTCGGGCCGGCCGAGCGA
GCGGGCCAA
bICP22 sequence

SEQ ID NO:43

PCR amplification of ~400bp BHV-1 gE CT fragment using gE CT-specific primer pairs, P7 and P8

PCR amplification of ~550bp BHV-1 Us9 fragment using Us9 ORF-specific primer pairs, P11 and P12

PCR amplification of ~1350bp BHV-1 gE ectodomain fragment using gE ectodomain-specific primer pairs, P5 and P6

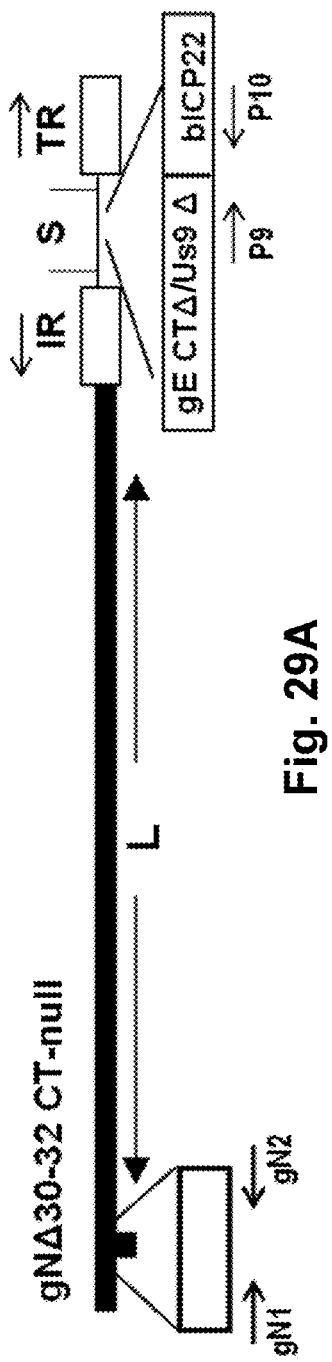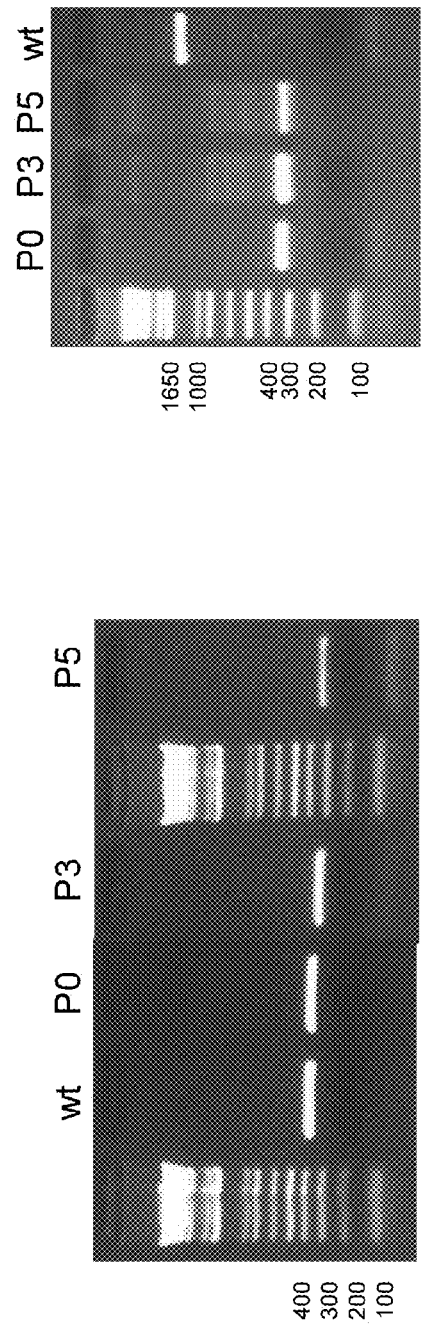
Fig. 29A
Fig. 29B
Fig. 29C

Fig. 30

SEQUENCE LISTING

```
<160> NUMBER OF SEQ ID NOS: 43

<210> SEQ ID NO 1
<211> LENGTH: 16
<212> TYPE: PRT
<213> ORGANISM: Bovine herpes virus-1

<400> SEQUENCE: 1

Gln Ala Val His Ala Leu Arg Glu Arg Ser Pro Arg Ala His Arg Cys
1               5                   10                  15

<210> SEQ ID NO 2
<211> LENGTH: 82
<212> TYPE: DNA
<213> ORGANISM: Artificial Sequence
<220> FEATURE:
<223> OTHER INFORMATION: Synthetic primer

<400> SEQUENCE: 2
aatggtcgcc gtggccctgt acgcgtacgg gctttgcttt taagcgccag cgggcccaat      60
aggatgacga cgataagtag gg                                              82

<210> SEQ ID NO 3
<211> LENGTH: 85
<212> TYPE: DNA
<213> ORGANISM: Artificial Sequence
<220> FEATURE:
<223> OTHER INFORMATION: Synthetic primer

<400> SEQUENCE: 3 cgccccgcg actccttttt attgggcccg ctggcgctta aaagcaaagc ccgtacgcgt       60
caaccaatta accaattctg attag                                           85

<210> SEQ ID NO 4
<211> LENGTH: 82
<212> TYPE: DNA
<213> ORGANISM: Artificial Sequence
<220> FEATURE:
<223> OTHER INFORMATION: Synthetic primer

<400> SEQUENCE: 4
tgccatcgtg cgcggccgcg accccctgct agacgcgatg ggggcaatgg acttttggag      60
aggatgacga cgataagtag gg                                              82

<210> SEQ ID NO 5
<211> LENGTH: 85
<212> TYPE: DNA
```

```
<213> ORGANISM: Artificial Sequence
<220> FEATURE:
<223> OTHER INFORMATION: Synthetic primer

<400> SEQUENCE: 5
cgcgcgcgta gcagcctgcg ctccaaaagt ccattgcccc catcgcgtct agcaggggt      60 caaccaatta accaattctg attag                                          85

<210> SEQ ID NO 6
<211> LENGTH: 83
<212> TYPE: DNA
<213> ORGANISM: Artificial Sequence
<220> FEATURE:
<223> OTHER INFORMATION: Synthetic primer

<400> SEQUENCE: 6 acccctgct agacgcgatg cggcgcgagg gggcaatgga cggctgctac gcgcgcgggg     60
taggatgacg acgataagta ggg                                            83

<210> SEQ ID NO 7
<211> LENGTH: 85
<212> TYPE: DNA
<213> ORGANISM: Artificial Sequence
<220> FEATURE:
<223> OTHER INFORMATION: Synthetic primer

<400> SEQUENCE: 7
gcggtggctc cgagagcggc accccgcgcg cgtagcagcc gtccattgcc ccctcgcgcc    60
caaccaatta accaattctg attag                                          85

<210> SEQ ID NO 8
<211> LENGTH: 84
<212> TYPE: DNA
<213> ORGANISM: Artificial Sequence
<220> FEATURE:
<223> OTHER INFORMATION: Synthetic primer

<400> SEQUENCE: 8
atgcggcgcg aggggggcaat ggacttttgg agcgcaggct gcgtgccgct ctcggagcca   60
ccaggatgac gacgataagt aggg                                           84

<210> SEQ ID NO 9
<211> LENGTH: 86
<212> TYPE: DNA
<213> ORGANISM: Artificial Sequence
<220> FEATURE:
<223> OTHER INFORMATION: Synthetic primer

<400> SEQUENCE: 9
taaaaaacaa ccagggcctg cggtggctcc gagagcggca cgcagcctgc gctccaaaag    60
tcaaccaatt aaccaattct gattag                                         86

<210> SEQ ID NO 10
<211> LENGTH: 91
<212> TYPE: DNA
<213> ORGANISM: Artificial Sequence
<220> FEATURE:
<223> OTHER INFORMATION: Synthetic primer

<400> SEQUENCE: 10
tgccatcgtg cgcggccgcg acccctgct agacgcgatg cggccgcgg ggcaatgga       60 cttttggaga ggatgacgac gataagtagg g                                   91
```

-continued

<210> SEQ ID NO 11
<211> LENGTH: 94
<212> TYPE: DNA
<213> ORGANISM: Artificial Sequence
<220> FEATURE:
<223> OTHER INFORMATION: Synthetic primer

<400> SEQUENCE: 11
cgcgcgcgta gcagcctgcg ctccaaaagt ccattgcccc cgcggccgcc atcgcgtcta 60
gcagggggtc aaccaattaa ccaattctga ttag 94

<210> SEQ ID NO 12
<211> LENGTH: 22
<212> TYPE: DNA
<213> ORGANISM: Artificial Sequence
<220> FEATURE:
<223> OTHER INFORMATION: Synthetic primer

<400> SEQUENCE: 12
agagcgccag cgagtcgggc tc 22

<210> SEQ ID NO 13
<211> LENGTH: 22
<212> TYPE: DNA
<213> ORGANISM: Artificial Sequence
<220> FEATURE:
<223> OTHER INFORMATION: Synthetic primer

<400> SEQUENCE: 13
agtccattgc cccctcgcgc cg 22

<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
gcgcgcgtag cagcctgcgc t 21

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
ctccgagagc ggcaccccgc 20

<210> SEQ ID NO 16
<211> LENGTH: 9
<212> TYPE: PRT
<213> ORGANISM: Bovine herpes virus-1

<400> SEQUENCE: 16

Ser Val Asn Lys Thr Glu Arg Ala Tyr
1 5

<210> SEQ ID NO 17
<211> LENGTH: 4
<212> TYPE: PRT
<213> ORGANISM: Bovine herpes virus-1

```
<400> SEQUENCE: 17

Phe Trp Ser Ala
1

<210> SEQ ID NO 18
<211> LENGTH: 4
<212> TYPE: PRT
<213> ORGANISM: Bovine herpes virus-1

<400> SEQUENCE: 18

Tyr Ala Arg Gly
1

<210> SEQ ID NO 19
<211> LENGTH: 38
<212> TYPE: DNA
<213> ORGANISM: Artificial Sequence
<220> FEATURE:
<223> OTHER INFORMATION: Synthetic primer

<400> SEQUENCE: 19
gcgagctgcg aattcgggaa cggcgcacgc gagagatg                            38

<210> SEQ ID NO 20
<211> LENGTH: 48
<212> TYPE: DNA
<213> ORGANISM: Artificial Sequence
<220> FEATURE:
<223> OTHER INFORMATION: Synthetic primer

<400> SEQUENCE: 20
gcggtacctt tattagtcag ttatgcgcgg cgcgcgcaca cccgaacg                 48

<210> SEQ ID NO 21
<211> LENGTH: 35
<212> TYPE: DNA
<213> ORGANISM: Artificial Sequence
<220> FEATURE:
<223> OTHER INFORMATION: Synthetic primer

<400> SEQUENCE: 21
ccgcgagtag gtaccgtcta atttttttccg cacgc                              35

<210> SEQ ID NO 22
<211> LENGTH: 35
<212> TYPE: DNA
<213> ORGANISM: Artificial Sequence
<220> FEATURE:
<223> OTHER INFORMATION: Synthetic primer

<400> SEQUENCE: 22
catcgacgtc aggatcctct tccgctgcat cgcca                               35

<210> SEQ ID NO 23
<211> LENGTH: 24
<212> TYPE: DNA
<213> ORGANISM: Artificial Sequence
<220> FEATURE:
<223> OTHER INFORMATION: Synthetic primer

<400> SEQUENCE: 23
cgccagggtt ttcccagtca cgac                                           24

<210> SEQ ID NO 24
```

```
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
tcacacagga aacagctatg ac                                           22

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
cccgctggcg cccatgagcc ta                                           22

<210> SEQ ID NO 26
<211> LENGTH: 30
<212> TYPE: DNA
<213> ORGANISM: Artificial Sequence
<220> FEATURE:
<223> OTHER INFORMATION: Synthetic primer

<400> SEQUENCE: 26
cgtttacaag ccgcggacgt gcgcgacatg                                   30

<210> SEQ ID NO 27
<211> LENGTH: 40
<212> TYPE: DNA
<213> ORGANISM: Artificial Sequence
<220> FEATURE:
<223> OTHER INFORMATION: Synthetic primer

<400> SEQUENCE: 27
tttattagtc agttatgcgc ggcgcgcgca cacccgaacg                        40

<210> SEQ ID NO 28
<211> LENGTH: 28
<212> TYPE: DNA
<213> ORGANISM: Artificial Sequence
<220> FEATURE:
<223> OTHER INFORMATION: Synthetic primer

<400> SEQUENCE: 28
atgatcgcag ccctcgccgt tcgggtgt                                     28

<210> SEQ ID NO 29
<211> LENGTH: 25
<212> TYPE: DNA
<213> ORGANISM: Artificial Sequence
<220> FEATURE:
<223> OTHER INFORMATION: Synthetic primer

<400> SEQUENCE: 29
gtagcggagg atggacttga gtcgc                                        25

<210> SEQ ID NO 30
<211> LENGTH: 23
<212> TYPE: DNA
<213> ORGANISM: Artificial Sequence
<220> FEATURE:
<223> OTHER INFORMATION: Synthetic primer

<400> SEQUENCE: 30
```

```
caggcccacc gctcaccagc gag                                            23

<210> SEQ ID NO 31
<211> LENGTH: 25
<212> TYPE: DNA
<213> ORGANISM: Artificial Sequence
<220> FEATURE:
<223> OTHER INFORMATION: Synthetic primer

<400> SEQUENCE: 31
gagccggagc tttggcccgc tcgct                                          25

<210> SEQ ID NO 32
<211> LENGTH: 24
<212> TYPE: DNA
<213> ORGANISM: Artificial Sequence
<220> FEATURE:
<223> OTHER INFORMATION: Synthetic primer

<400> SEQUENCE: 32
atggagagtc cacgcagcgt cgtc                                           24

<210> SEQ ID NO 33
<211> LENGTH: 23
<212> TYPE: DNA
<213> ORGANISM: Artificial Sequence
<220> FEATURE:
<223> OTHER INFORMATION: Synthetic primer

<400> SEQUENCE: 33
gaagacaggc gcgggcgtgc gga                                            23

<210> SEQ ID NO 34
<211> LENGTH: 96
<212> TYPE: PRT
<213> ORGANISM: Bovine herpes virus-1

<400> SEQUENCE: 34

Met Pro Arg Ser Pro Leu Ile Val Ala Val Val Ala Ala Ala Leu Phe
1               5                   10                  15

Ala Ile Val Arg Gly Arg Asp Pro Leu Leu Asp Ala Met Arg Arg Glu
            20                  25                  30

Gly Ala Met Asp Phe Trp Ser Ala Gly Cys Tyr Ala Arg Gly Val Pro
        35                  40                  45

Leu Ser Glu Pro Pro Gln Ala Leu Val Val Phe Tyr Val Ala Leu Thr
    50                  55                  60

Ala Val Met Val Ala Val Ala Leu Tyr Ala Tyr Gly Leu Cys Phe Arg
65                  70                  75                  80

Leu Met Gly Ala Ser Gly Pro Asn Lys Lys Glu Ser Arg Gly Arg Gly
                85                  90                  95

<210> SEQ ID NO 35
<211> LENGTH: 32
<212> TYPE: PRT
<213> ORGANISM: Bovine herpes virus-1

<400> SEQUENCE: 35

Asp Pro Leu Leu Asp Ala Met Arg Arg Glu Gly Ala Met Asp Phe Trp
1               5                   10                  15

Ser Ala Gly Cys Tyr Ala Arg Gly Val Pro Leu Ser Glu Pro Pro Gln
            20                  25                  30
```
<210> SEQ ID NO 36
<211> LENGTH: 29
<212> TYPE: PRT
<213> ORGANISM: Bovine herpes virus-1

<400> SEQUENCE: 36

```
Asp Pro Leu Leu Asp Ala Met Gly Ala Met Asp Phe Trp Ser Ala Gly
1               5                   10                  15

Cys Tyr Ala Arg Gly Val Pro Leu Ser Glu Pro Pro Gln
            20                  25
```

<210> SEQ ID NO 37
<211> LENGTH: 291
<212> TYPE: DNA
<213> ORGANISM: Bovine herpes virus-1

<400> SEQUENCE: 37

```
atgccgcggt cgccgctcat cgttgcggtt gtggccgccg cgctgtttgc catcgtgcgc     60
ggccgcgacc ccctgctaga cgcgatgcgg cgcgaggggg caatggactt ttggagcgca    120
ggctgctacg cgcgcggggt gccgctctcg gagccaccgc aggccctggt tgttttttac    180
gtggccctga ccgcggtaat ggtcgccgtg gccctgtacg cgtacgggct ttgctttagg    240
ctcatgggcg ccagcgggcc caataaaaag gagtcgcggg ggcggggctg a             291
```

<210> SEQ ID NO 38
<211> LENGTH: 93
<212> TYPE: DNA
<213> ORGANISM: Bovine herpes virus-1

<400> SEQUENCE: 38

```
gtaatggtcg ccgtggccct gtacgcgtac gggctttgct ttaggctcat gggcgccagc     60
gggcccaata aaaaggagtc gcgggggcgg ggc                                  93
```

<210> SEQ ID NO 39
<211> LENGTH: 31
<212> TYPE: PRT
<213> ORGANISM: Bovine herpes virus-1

<400> SEQUENCE: 39

```
Val Met Val Ala Val Ala Leu Tyr Ala Tyr Gly Leu Cys Phe Arg Leu
1               5                   10                  15

Met Gly Ala Ser Gly Pro Asn Lys Lys Glu Ser Arg Gly Arg Gly
            20                  25                  30
```

<210> SEQ ID NO 40
<211> LENGTH: 21
<212> TYPE: PRT
<213> ORGANISM: Bovine herpes virus-1

<400> SEQUENCE: 40

```
Ile Val Arg Gly Arg Asp Pro Leu Leu Asp Ala Met Arg Arg Glu Gly
1               5                   10                  15

Ala Met Asp Phe Trp
            20
```

<210> SEQ ID NO 41
<211> LENGTH: 69
<212> TYPE: DNA
<213> ORGANISM: Bovine herpes virus-1

<400> SEQUENCE: 41

-continued

```
tgccatcgtg cgcggccgcg accccctgct agacgcgatg cggcgcgagg gggcaatgga    60
cttttggag                                                             69
```

<210> SEQ ID NO 42
<211> LENGTH: 2683
<212> TYPE: DNA
<213> ORGANISM: Bovine herpes virus-1

<400> SEQUENCE: 42

```
atgcaaccca ccgcgccgcc ccggcggcgg ttgctgccgc tgctgctgcc gcagttattg    60
cttttcgggc tgatggccga ggccaagccc gcgaccgaaa ccccgggctc ggcttcggtc   120
gacacggtct tcacggcgcg cgctggcgcg cccgtctttc tcccagggcc cgcggcgcgc   180
ccggacgtgc gcgccgttcg cggctggagc gtcctcgcgg gcgcctgctc gccgcccgtg   240
ccggagcccg tctgcctcga cgaccgcgag tgcttcaccg acgtggccct ggacgcggcc   300
tgcctgcgaa ccgcccgcgt ggccccgctg ccatcgcgg agctcgccga gcggcccgac   360
tcaacgggcg acaaagagtt tgttctcgcc gacccgcacg tctcggcgca gctgggtcgc   420
aacgcgaccg gggtgctgat cgcggccgca gccgaggagg acggcggcgt gtacttcctg   480
tacgaccggc tcatcggcga cgccggcgac gaggagacgc agttggcgct gacgctgcag   540
gtcgcgacgg ccggcgcgca gggcgccgcg cgggacgagg agagggaacc agcgaccggg   600
cccacccccg gcccgccgcc ccaccgcacg acgacacgcg cgccccgcg gcggcacggc   660 gcgcgcttcc gcgtgctgcc gtaccactcc cacgtataca ccccgggcga ttcctttctg   720
ctatcggtgc gtctgcagtc tgagtttttc gacgaggctc ccttctcggc cagcatcgac   780
tggtacttcc tgcggacggc cggcgactgc gcgctcatcc gcatatacga gacgtgcatc   840
ttccaccccg aggcaccggc ctgcctgcac cccgccgacg cgcagtgcag cttcgcgtcg   900
ccgtaccgct ccgagaccgt gtacagccgg ctgtacgagc agtgccgccc ggaccctgcc   960
ggtcgctggc cgcacgagtg cgagggcgcc gcgtacgcgg cgcccgttgc gcacctgcgt  1020
cccgccaata acagcgtaga cctggtctttt gacgacgcgc cggctgcggc ctccgggctt  1080
tacgtctttg tgctgcagta caacggccac gtggaagctt gggactacag cctagtcgtt  1140
acttcggacc gtttggtgcg cgcggtcacc gaccacacgc gccccgaggc cgcagccgcc  1200
gacgctcccg agccaggccc accgctcacc agcgagccgg cgggcgcgcc caccgggccc  1260
gcgccctggc ttgtggtgct ggtgggcgcg cttggactcg cgggactggt gggcatcgca  1320
gccctcgccg ttcgggtgtg cgcgcgccgc gcaagccaga agcgcaccta cgacatcctc  1380
aaccccttcg ggcccgtata caccagcttg ccgaccaacg agccgctcga cgtggtggtg  1440
ccagttagcg acgacgaatt tccctcgac gaagactctt ttgcggatga cgacagcgac  1500
gatgacgggc ccgctagcaa cccccctgcg gatgcctacg acctcgccgg cgccccagag  1560
ccaactagcg ggtttgcgcg agccccgcc aacggcacgc gctcgagtcg ctctgggttc  1620
aaagtttggt ttagggaccc gcttgaagac gatgccgcgc cagcgcggac cccggccgca  1680
ccagattaca ccgtggtagc agcgcgactc aagtccatcc tccgctaggc gccccccccc  1740
ccgcgcgctg tgccgtctga cggaaagcac ccgcgtgtag gctgcatat aaatggagcg  1800 ctcacacaaa gcctcgtgcg gctgcttcga aggcatggag agtccacgca gcgtcgtcaa  1860
cgaaaactat cgaggcgctg atgaggccga tgcagcgccc ccttcaccgc cgccggaagg  1920
ctccatcgtg tccatcccca tcctcgagct caccatcgag gacgcgccgg ccagcgcaga  1980
```

```
agcaaccggc accgcggcag ccgcacccgc tgggcgcact ccagacgcga acgcagcacc    2040
cggcggctac gtgccagttc ccgcggcgga tgtggactgc tattatagcg aaagcgacag    2100
cgagacggca ggcgagtttt tgatacgcat ggggcggcag cagcggcggc ggcatcggcg    2160
gcggcgctgc atgatagcag cggccctgac ttgcattggc ctcggggcct gcgcggcggc    2220
ggcagcggca ggcgccgtcc tggcgttgga ggtagtgccc cggccctgag gccccgagac    2280
ccccggccct gaggccctgg ggcggggccc gactgtcccc ttcccccctc cccccgtcc    2340 gcccgcgagt aaaggctgtc taattttttc cgcacgcccg cgcctgtctt cttagggagg    2400
ggaaggaggg gagggagggg aaggagggga gggaggggaa ggaggggagg gaggggaagg    2460
aggggaggga ggggaaggag gggagggagg ggaaggaggg gagggagggg aaggagggga    2520
gggaggggaa ggaggggagg gaggggaagg aggggaggga ggggaaggag gggagggagg    2580
ggaaggaggg gagggagggg aaggagggga gggagggaa ggaggggatt cgggccggcc    2640
gaggattcgg gccggccgag cgagcgggcc aaagctccgg ctc                     2683

<210> SEQ ID NO 43
<211> LENGTH: 223
<212> TYPE: DNA
<213> ORGANISM: Bovine herpes virus-1

<400> SEQUENCE: 43
actggtgggc atcgcagccc tcgccgttcg ggtgtgcgcg cgccgcgcat aactgactaa     60
taaaggtacc gtctaatttt ttccgcacgc ccgcgcctgt cttcttaggg aggggaagga    120
ggggagggag gggaaggagg ggagggaggg gaaggagggg agggagggga aggaggggat    180
tcgggccggc cgaggattcg ggccggccga gcgagcgggc caa                      223
```

BOVINE HERPES VIRUS VACCINE WITH MULTIPLE MUTATIONS

The benefit of the Jun. 27, 2011 filing date of U.S. provisional application Ser. No. 61/501,545 is claimed under 35 U.S.C. §119(e).

This invention was made with United States government support under grant nos. USDA 2007-35204-05420 and 2009-35204-05200 awarded by the United States Department of Agriculture. The government has certain rights in this invention.

This invention pertains to a recombinant BHV-1 vaccine virus that incorporates into a single virus two or more deletions in one or more of three genes—$U_L49.5$ (gN), gE and Us9.

Bovine herpesvirus type 1 (BHV-1) is an important pathogen of cattle that can cause severe respiratory tract infection known as infectious bovine rhinotracheitis (IBR). IBR can cause abortion in pregnant cows [1-3; see also, U.S. Pat. No. 6,221,360] and a substantial drop in milk and meat production. BHV-1 is also an important component of the Bovine Respiratory Disease Complex (BRDC or "Shipping fever") [3,4]. During primary infection, BHV-1 replicates in the nasal and upper respiratory tract epithelium and transiently depresses cell-mediated immunity and evades the host cytotoxic $CD8^+$ T cell recognition by down regulating the cell surface expression of major histocompatibility complex class I (MHC-I) molecules [10,11,15]. This immunosuppression combined with lesions in the upper respiratory tract facilitates secondary bacterial infections and pneumonia [3]. Both IBR disease and BRDC cause considerable losses for the cattle industry worldwide and cost the US cattle industry at least $1 billion dollars annually [2].

Another problem with BHV-1 infection in cattle is that the virus establishes a life-long latency in trigeminal ganglia (TG) following the primary infection [3]. During the primary infection, the virus enters the sensory nerve endings (axon terminals) of the trigeminal nerve in the nasopharynx and is transported up the axon retrogradely to the neuronal cell bodies in the TG where BHV-1 establishes life-long latency [3]. Periodically throughout the life of the animal, the latent virus in the TG reactivates due to immunosuppression or stress. Following reactivation, the virus is transported down the axon to the primary infection sites in the nose and/or eye. The viral infection causes ocular and nasal virus shedding [3] which facilitates virus transmission to other cattle. Thus this reactivation followed by shedding maintains an ongoing viral infection in susceptible cattle populations.

In BHV-1-infected cells, envelope protein $U_L49.5$ (a BHV-1 homolog of envelope glycoprotein N (gN)) was found to block the Transporter associated with Antigen Presentation (TAP) function required for the display of viral peptides on the cell surface. To promote the immune response from the host, the MHC-I molecules must be loaded with viral peptides. BHV-1 $U_L49.5$ binds to the TAP complex, blocks the TAP conformational changes, and degrades TAP [10]. Consequently, peptides are not loaded onto the MHC-I molecules in the endoplasmic reticulum (ER) which is required for the MHC-I transport to cell surface and cell surface expression [10,11]. This results in transient MHC-I down-regulation in a susceptible host and helps the virus evade destruction by the CD8+ T cells at an early stage of virus infection of the host [3].

BHV-1 mutants have been made and analyzed for use as vaccines. One commercial vaccine is based on a deletion of the glycoprotein E (gE) gene. Following intranasal infection, both the gE-ORF-deleted (the entire gE gene deleted) and the gE cytoplasmic tail (CT)-truncated BHV-1 recombinant viruses were determined to be equally attenuated in calves and to have defective anterograde axonal transport [32,36]. Therefore, following dexamethasone-induced reactivation in the TG, no nasal virus shedding in calves infected with either virus was seen (32). Importantly, BHV-1 gE cytoplasmic tail-deleted virus-infected calves have two-fold higher serum neutralizing (SN) titers relative to calves infected with the entire gE ORF-deleted [32]. In addition, a BHV-1 gE-specific antibody raised against residues 366-575, which includes the entire gE cytoplasmic tail (453-575), was shown to immunoprecipitate BHV-1 gE [28,39].

The Us9-deleted BHV-1 is also known to be attenuated in calves. This mutated virus has defective anterograde transport in calves, and thus no virus shedding following dexamethasone-induced reactivation [43]. Importantly, calves infected with the Us9-deleted BHV-1 have similar SN titers relative to the wild-type BHV-1-infected calves [43]. Recently, a BHV-1 mutant virus lacking only the Us9 acidic portion, domain residues 83-90, was shown to be defective in axonal anterograde transport [40].

Other genetically engineered gene-deleted vaccines have been developed that are attenuated and that can be serologically distinguished from wild-type field strains. Numerous viral mutants (e.g., gC-, gE-, gG-, deleted [33, 37, 43] and thymidine kinase (TK)-deleted [25,38]) have been constructed and analyzed for the in vivo pathogenic properties, reactivation properties, and immunogenicity. [See also, U.S. Pat. No. 5,151,267] Studies with gC-, gG-, or TK-deleted viruses showed that these mutant viruses either reactivate from latency and/or retain some degree of virulence [37, 38]. The genetically engineered gE gene-deleted IBR marker vaccine has become increasingly used because the vaccine virus is attenuated and, unlike the traditional Modified Live Viruses (MLVs), the vaccine virus can be serologically distinguished from the wild-type virus. In addition, the gE gene-deleted vaccine virus has defective anterograde neuronal transport from neuronal cell bodies in the trigeminal ganglia (TG) to nerve endings in the nasal epithelium, and the virus is not shed in the nose following latency reactivation in the TG [3, 33, 37, 38, 43; see also, U.S. Pat. Nos. 6,403,097; 6,284,251; 6,086,902; and 5,676,951]. The MLVs and gE gene-deleted vaccines have been shown to be immunosuppressive and not optimally efficacious [17, 41, 42]. For example, comparative vaccine efficacy studies showed that relative to gC- and gG-deleted viruses, the gE-deleted virus is less efficacious [37]. A gE cytoplasmic tail (CT)-truncated virus was shown to be equally attenuated in animals relative to gE-ORF-deleted marker vaccine, and had no nasal virus shedding following reactivation [32].

Another problem that must be addressed by a vaccine for a BHV-1 virus infection is the immunosuppressive ability of the BHV-1 virus. Normally, proteosomally processed viral proteins yield peptides that bind to TAP heterodimer, consisting of the subunits TAP1 and TAP2 [5-7]. Following viral peptide binding, the TAP1/TAP2 heterodimer undergoes conformational changes [5-7]. Subsequently, peptides are transported into the ER and loaded onto MHC-I molecules to form MHC/peptide complexes which are transported to and presented on the antigen-presenting cell surface [8, 9]. However, in BHV-1-infected cells, envelope protein $U_L49.5$ (a homolog to and also known as glycoprotein N (gN)) binds to TAP, interferes with its peptide transport function and also degrades the TAP [10,11]. Consequently, BHV-1 interferes with the MHC class I antigen presentation pathway, and during the initial phase of viral infection, escapes host cellular immune surveillance and elimination [9,11-15]. Modified live vaccines (MLV) against BHV-1 including genetically engineered gE-deleted marker vaccines are being used for vaccination against BHV-1. However, problems associated with BHV-1 infection in the vaccinated animals exist, especially in the feedlot. Since both the traditional and gE-deleted MLVs have wild-type $U_L49.5$, these vaccines like the wild-type virus, are transiently immunosuppressive. Therefore, there is a need for further improvement of the current MLVs [16-19].

Alphaherpesvirus $U_L49.5$ and gM homologs are associated with cellular and virion membranes and the $U_L49.5$ (gN) homologs form complexes with envelope glycoprotein gM [20-22]. BHV-1 $U_L49.5$ predicted ORF is composed of an N-terminal signal sequence of 22 amino acids (aa), an extracellular luminal domain of 32 aa, a transmembrane (TM) domain of 25 aa, and a short cytoplasmic tail (CT) of 17 aa [10,22,23]. A BHV-1 $U_L49.5$ CT-truncated virus lacking the cytosolic 17 amino acids has been shown to no longer degrade bovine TAP molecules, but to retain the TAP inhibition and MHC-I down-regulation functions [15].

Using N-terminal and C-terminal truncated versions of BHV-1 $U_L49.5$ expressed in a Baculovirus expression vector system, $U_L49.5$ luminal domain residues 23-32 and $U_L49.5$ cytoplasmic tail residues 94-96 were found to be essential for $U_L49.5$-mediated degradation of human TAP [24]. However, $U_L49.5$ luminal domain residues 28-32 alone are sufficient for human TAP inhibition and down-regulation of human MHC-I surface expression [24].

We have developed a recombinant BHV-1 vaccine virus that incorporates into a single virus at least two deletions in one or more of three genes—$U_L49.5$ (also called herein "glycoprotein N" or "gN"), gE and Us9. Specifically, we made and tested a BHV-1 $U_L49.5\Delta30$-32 CT-null virus. We then used this mutant virus to incorporate additional deletions, e.g., the gE cytoplasmic-tail deletion, Us9 deletion, or both. This triple mutant BHV-1 $U_L49.5\Delta30$-32 CT-null/gE CTΔ/Us9Δ virus is believed to be superior to current BHV-1 mutants because this mutant virus will not be shed following reactivation, will be serologically distinguishable from wild-type, and will induce better protective response by inducing quicker and higher SN titers and cellular immune responses. We will test the new mutant viruses in rabbits for viral replication in the nasal epithelium and for differential serological marker properties relative to wild-type BHV-1. We have verified that this BHV-1 $U_L49.5\Delta30$-32 CT-null/gE CTΔ/Us9Δ virus has the expected deletions, and that these deletions are stable through at least five serial passages.

We have constructed BHV-1 $U_L49.5$ luminal domain mutants with a short sequence deletion using a BHV-1 $U_L49.5$ cytoplasmic tail (CT) null virus or wt BHV-1 as a backbone, and analyzed their TAP inhibition and MHC-I molecule surface expression properties in infected MDBK cells relative to wt BHV-1. The results demonstrated that $U_L49.5$ residues 30 to 32 are essential for the BHV-1 $U_L49.5$-mediated TAP inhibition/MHC-I down-regulation function. The mutant $U_L49.5$ lacking luminal domain residues 30-32 was shown to abolish the TAP1 degradation and the TAP1-mediated MHC-I down-regulation. Most notably, in a calf infection and challenge experiment, we found the following: (i) BHV-1 $U_L49.5\Delta30$-32 CT-null virus replicated efficiently in the nasal epithelium; (ii) a 2-fold increase in serum neutralization (SN) titers was seen in BHV-1 $U_L49.5\Delta30$-32 CT-null virus-infected calves relative to the wild-type BHV-1 infected calves both at 21-days post infection and at 2 weeks post challenge; and iii) a 3-fold (270%) and 50% increase was seen in CD8+ cell proliferation in BHV-1 $U_L49.5\Delta30$-32 CT-null virus-infected calves relative to the wild-type BHV-1 infected calves at 7 days post-infection and 7 days post wild-type BHV-1 challenge, respectively.

BRIEF DESCRIPTION OF DRAWINGS

FIG. 1A illustrates the predicted amino acid (aa) sequences of BHV-1 $U_L49.5$ open reading frame (ORF) (SEQ ID NO:34), with the bold letters indicating the $U_L49.5$ cytoplasmic tail residues and the underlined region indicating the $U_L49.5$ luminal domain residues. In the $U_L49.5\Delta30$-32 CT-null mutant, the $U_L49.5$ residues 30RRE32 of the luminal domain are deleted, along with the $U_L49.5$ cytoplasmic tail residues 80RL81. In addition, $U_L49.5$ residues 82M through 96G are not expressed due to an amber mutation replacing the 82M to a stop codon.

FIG. 1B illustrates a schematic drawing showing the wt $U_L49.5$ with the luminal domain residues listed (SEQ ID NO:35), and residues 30RRE32 italicized and bolded.

FIG. 1C illustrates a schematic drawing showing the $U_L49.5$ CT-null the luminal domain residues listed (SEQ ID NO:35), and residues 30RRE32 italicized and bolded.

FIG. 1D illustrates a schematic drawing showing the $U_L49.5\Delta30$-32 CT-null mutant showing the luminal domain residues remaining after the deletion of residues 30-32 (SEQ ID NO:36).

FIG. 2 illustrates the DNA sequence of wild type BHV-1 $U_L49.5$ (SEQ ID NO:37) and shows the changes to generate BHV-1 $U_L49.5$ CT-null, i.e., the deletion of nucleotides 238 to 244 and the mutation of nucleotides 246 and 247 to AA to introduce a strong stop codon TAA.

FIG. 3 illustrates the strategy used to design PCR primers for generating the BHV-1 $U_L49.5$ CT-null mutant by showing the relevant section of the $U_L49.5$ peptide (SEQ ID NO:39) and DNA sequence (SEQ ID NO:38), and the forward (SEQ ID NO:2) and reverse (SEQ ID NO:3) primer pair.

FIG. 4 illustrates the strategy used to design the PCR primers for generating the BHV-1 $U_L49.5\Delta30$-32 CT-null mutant by showing the relevant section of the $U_L49.5$ peptide (SEQ ID NO:41) and DNA sequence (SEQ ID NO:40), and the forward (SEQ ID NO:4) and reverse (SEQ ID NO:5) primer pair.

FIG. 15A is a schematic illustration of the BHV-1 genome showing the locations of the BHV-1 gN ($U_L$49.5), gE, Us9, and bICP22 genes, with the orientations of gE, Us9, and bICP22 gene transcriptions indicated by arrows.

FIG. 15B is a schematic illustration of the BHV-1 wt $U_L$49.5 residues, highlighting the luminal domain residues of BHV-1 wt (SEQ ID NO:35) and of BHV-1 $U_L$49.5Δ30-32 CT-null (SEQ ID NO:36).

FIG. 15C is a schematic illustration of the BHV-1 $U_L49.5\Delta30$-32 CT-null/gE CT$\Delta$/Us9$\Delta$ viral genome.

FIG. 16B is a list of primers (P1, SEQ ID NO:19; P2, SEQ ID NO:20; P3, SEQ ID NO:21; and P4, SEQ ID NO:22) used to generate pBHV-1 gE CT$\Delta$/Us9$\Delta$. Poly A and Stop sequences designed in P2 are complementary. The nucleotide numbers, 1329-1353, refer to SEQ ID NO:42 shown in FIG. 18.

FIG. 18 shows the nucleotide sequence spanning the gE, Us9, and part of bICP22 genes of BHV-1 wt genome (SEQ ID NO:42; GenBank accession #AJ004801). The Start and Stop codons for gE and Us9 are marked. The gE CT residue 451 alanine which is retained in the BHV-1 $U_L49.5\Delta30$-32 CT-null/gE CT$\Delta$/Us9$\Delta$ viral genome is also marked.

FIG. 20 shows the nucleotide sequence (SEQ ID NO:43) spanning the gE ectodomain-bICP22 junction area sequences of plasmid clone pBHV-1 gE CT$\Delta$/Us9$\Delta$ DNA. The gE aa451 (alanine) encoded by GCA is marked by the arrow. In addition, the triple stop codons, poly A sequence, and KpnI sites immediately left (downstream of bICP22 based on the gene orientation shown in FIG. 15A) of the bICP22 are shown. The references to nucleotide sequence numbers are as shown in SEQ ID NO:42, FIG. 18.

FIG. 29A is a schematic drawing of the genome organization of BHV-1 $U_L49.5\Delta30$-32 CT-null/gE CT$\Delta$/Us9$\Delta$ virus, showing the location of the PCR and/or sequencing primers for verification of the stability of the deleted sequences after five serial passages in MDBK cells.

FIG. 29B shows the results of PCR amplification of the BHV-1 $U_L49.5\Delta30$-32 CT-null/gE CT$\Delta$/Us9$\Delta$ virus DNA at passage 0 (P0), three serial passages (P3), and five serial passages (P5) using the $U_L49.5$-specific primer pair of $U_L49.5$-1/$U_L49.5$-2 as shown in Table 3 and FIG. 29A.

FIG. 29C shows the results of PCR amplification of the BHV-1 $U_L49.5\Delta30$-32 CT-null/gE CT$\Delta$/Us9$\Delta$ virus DNA at passage 0 (P0), three serial passages (P3), and five serial passages (P5) using the gE-ICP22 primer pair of P9/P10 as shown in Table 3 and FIG. 29A.

Figure 30:
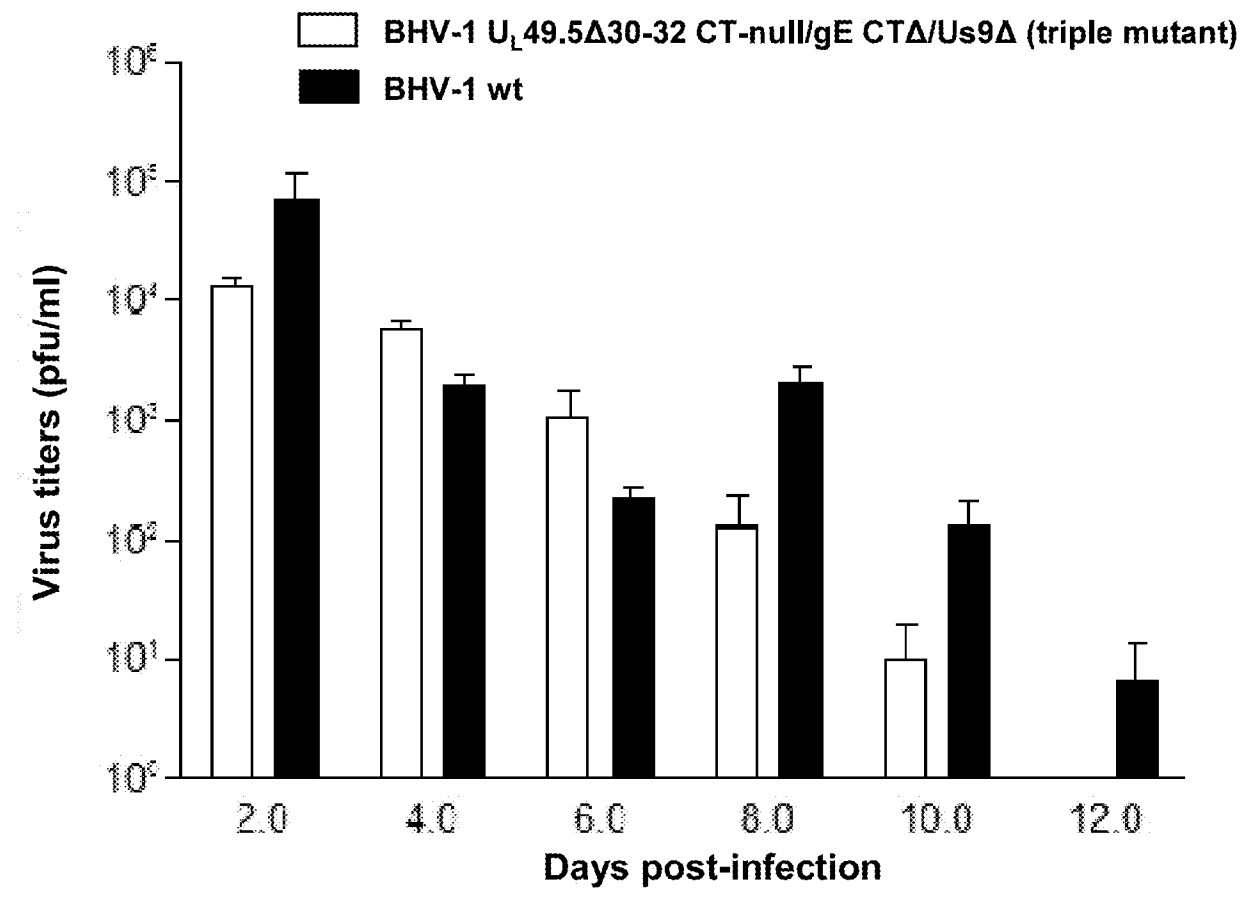

FIG. 30 illustrates the results of an analysis of nasal virus shedding in rabbits either infected with BHV-1 wt virus or infected with BHV-1 $U_L49.5\Delta30$-32 CT-null/gE CT$\Delta$/Us9$\Delta$ virus at the indicated intervals (days post infection (dpi)). The data represent an average of five rabbits in each treatment group.

MODES FOR CARRYING OUT INVENTION

Figure 5:
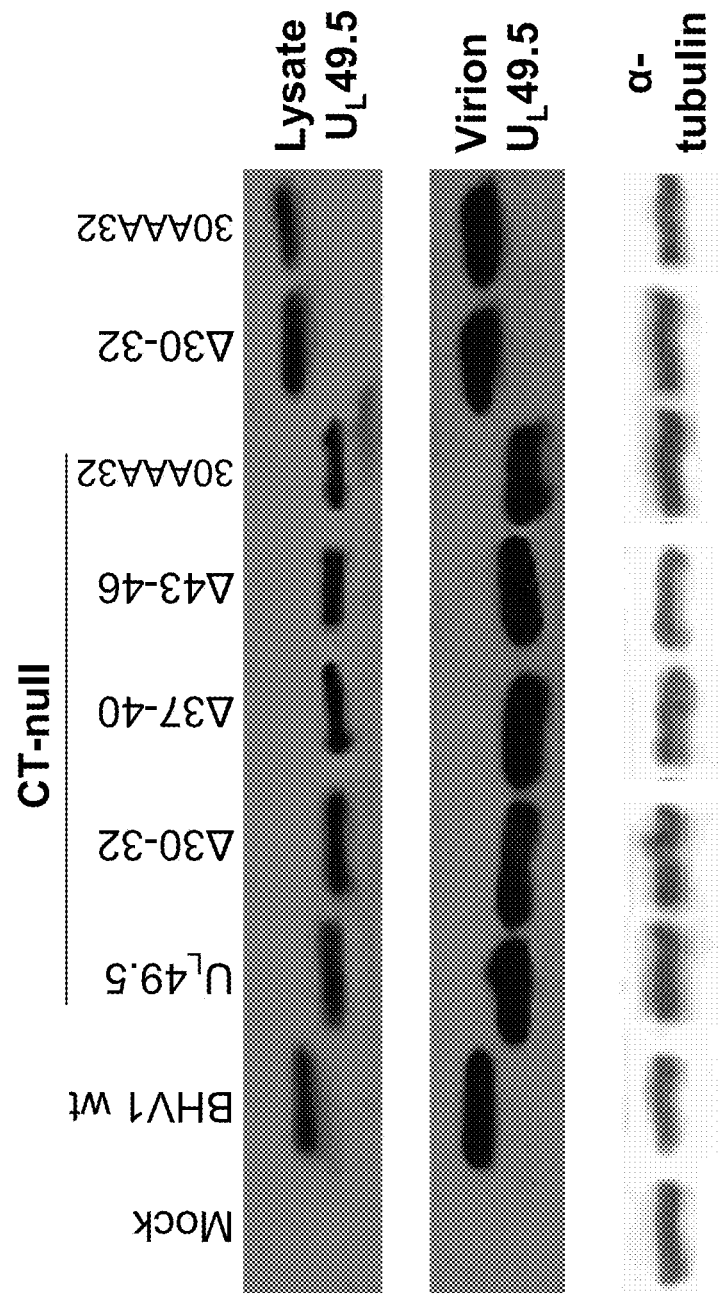
FIG. 5 illustrates the results of an immunoblotting analysis of mutant $U_L49.5$ expressed in the infected cells and incorporated in the virion envelope by various $U_L49.5$ mutant viruses, including uninfected (Mock), BHV-1 wt, BHV-1 CT-null, BHV-1 $U_L49.5\Delta30$-32 CT-null, BHV-1 $U_L49.5\Delta37$-40 CT-null, BHV-1 $U_L49.5\Delta43$-46 CT-null, BHV-1 $U_L49.5$ 30AAA32 CT-null, BHV-1 $U_L49.5\Delta30$-32, and BHV-1 $U_L49.5$ 30AAA32. The virus-infected cell lysates or partially purified virions were separated by a 10-20% gradient SDS-PAGE and incubated with rabbit anti-BHV-1 α-$U_L49.5$ specific antibody. Equal amounts of the extracted cell lysates or virions were loaded, and α-tublin was used as a control.

We have developed a recombinant BHV-1 vaccine virus that incorporates into a single virus two or more deletions in one or more of three genes—$U_L49.5$ (gN), gE and Us9. Specifically, we made and tested a BHV-1 $U_L49.5\Delta30$-32 CT-null virus, and then used this virus to incorporate additional changes, e.g., the gE cytoplasmic-tail deletion, Us9 deletion, or both. This triple mutant BHV-1 $U_L49.5\Delta30$-32 CT-null/gE CTΔ/Us9Δ virus was shown to be stable, and will be a superior vaccine to the current BHV-1 mutants. The advantages of this new mutant used as a BHV-1 vaccine are the following: (1) the mutant virus will not be shed following reactivation; (2) the mutant virus is serologically distinguishable from wt BHV-1 (a DIVA based on gE CT-specific serum antibodies); and (3) the mutant virus will induce a better and faster protective response by inducing higher SN titers and better cellular immune responses. The new mutant viruses can also be used as vectors for exogenous gene expression.

We constructed BHV-1 $U_L49.5$ luminal domain mutants in the wt $U_L49.5$ or $U_L49.5$ CT-null backgrounds and determined their TAP inhibition, TAP degradation and MHC-I down-regulation properties in virus-infected MDBK cells relative to mock- and BHV-1 wt-infected MDBK cells. Further, we determined the effects of $U_L49.5$ mutations that abolished the $U_L49.5$-mediated TAP inhibition/MHC-I down-regulation functions (BHV-1 $U_L49.5\Delta30$-32 CT-null) on virus replication and $U_L49.5$ (gN)/gM interaction. We found that: (1) Relative to wt-infected cells, cells-infected with $U_L49.5$ mutants having residues 30-32 deleted or substituted with alanine have significantly increased TAP mediated peptide transport and MHC-I surface expression. However, when BHV-1 $U_L49.5\Delta30$-32 mutation is combined with deletion of the $U_L49.5$ CT residues, there was a significant increase in peptide transport and MHC-I surface expression. (2) Either deletion of $U_L49.5$ residues 30-32 or of $U_L49.5$ CT-null mutation individually prevented $U_L49.5$-mediated bovine TAP1 degradation. (3) BHV-1 $U_L49.5\Delta30$-32 mutant virus replicated with wild-type efficiency in MDBK cells. (4) Mutant $U_L49.5\Delta30$-32/gM interaction and gM processing in mutant virus-infected cells were not affected.

Embodiments for this invention include, but are not limited to, the following: (1) a mutant BHV-1 virus comprising at least two mutations in $U_L49.5$; (2) a mutant BHV-1 virus in which the two mutations in glycoprotein N are found in the cytoplasmic tail and in the luminal residues 30RRE32; and (3) a BHV-1 virus comprising two mutations in glycoprotein N and further comprising one or more mutations in glycoprotein E or in envelope protein Us9.

Other embodiments include, but are not limited to, the following: (1) a mutant BHV-1 virus comprising at least two mutations in glycoprotein N and further comprising one or more mutations in glycoprotein E in which at least one mutation is in the cytoplasmic tail of gE, e.g., gE CT-null; and (2) a mutant BHV-1 virus comprising at least two mutations in glycoprotein N and further comprising one or more mutations in the envelope protein Us9 in which at least one mutation is chosen from deletion of the entire Us9 gene or of the acidic portion, residues 83-90.

Other embodiments include, but are not limited to, the following: (1) a mutant BHV-1 virus comprising at least two mutations in $U_L49.5$ in which the two mutations are found in the cytoplasmic tail and in the luminal residues 30 to 32 and further comprising one or more mutations in glycoprotein E or in envelope protein Us9; (2) a mutant BHV-1 virus comprising at least two mutations in $U_L49.5$ in which the two mutations are found in the cytoplasmic tail and in the luminal residues 30RRE32 and further comprising the mutations of gE CT-null and Us9-deletion; and (3) a mutant BHV-1 virus comprising at least two mutations in $U_L49.5$ in which the two mutations are found in the cytoplasmic tail and in the luminal residues 30 to 32 and further comprising the mutations of gE CT-null and Us9-acidic portion, residues 83-90.

Other embodiments include, but are not limited to, the following: (1) a live vaccine based on any of the above embodiments of the attenuated mutant BHV-1 virus; (2) a vaccine based on the any of the above embodiments of the attenuated mutant BHV-1 virus that does not shed following reactivation, is a DIVA, and induces a protective response at a level higher than achieved by a vaccine based on a virus that does not have one or more mutations in $U_L49.5$; and (3) a vaccine composition comprising one or more of the vaccines based on any of the above embodiments of the attenuated mutant BHV-1 viruses and that further comprising a pharmaceutically acceptable vehicle or an adjuvant.

In another embodiment, any of the above embodiments of the attenuated, mutant BHV-1 viruses can be used as a vector which contains one or more heterologous genes introduced by recombinant DNA techniques. Examples of such heterologous genes include, without limitation, genes that code for an immunogenic peptide, e.g., cytokines, or genes that code for protective antigens of another pathogen, e.g., bovine viral diarrhea virus, bovine respiratory syncytial virus, bovine respiratory corona virus, parainfluenza virus, *Mannheimia haemolytica* (bacterial pathogen), etc. (See, U.S. Pat. No. 6,086,902). Such heterologous genes can be controlled by an exogenous gene that is a known promoter gene.

Example 1

BHV-1 $U_L49.5\Delta30$-32 CT-Null Production and Effect on MHC-1: Materials and Methods Cells and Virus Strain.

The Madin-Darby bovine kidney (MDBK) cell line obtained from the American Type Culture Collection (Manassas, Va.) was maintained in Dulbecco's modified Eagle's medium (DMEM) supplemented with 5-10% heat-inactivated fetal bovine serum (FBS) (HyClone Laboratories, Inc., South Logan, Utah). The BHV-1 Cooper (Colorado-1) strain, obtained from the American Type Culture Collection (Cat # CRL-1390; Manassas, Va.), was propagated and titrated in MDBK cells as previously published [25].

Plasmids and Bacterial Strains.

Vector pGEX-4T-2 (GE Healthcare, Piscataway, N.J.) and *E. coli* strain BL21 (GE Healthcare) were used to express BHV-1 $U_L49.5$-GST or bovine TAP1-GST fusion proteins. *E. coli* strain DH10B (Invitrogen, Carlsbad, Calif.) was used to maintain all the infectious BHV-1 BAC clones. *E. coli* strain SW105 (kindly provided by Dr. N. G. Copeland, Frederick, Md.) was used for Red recombination.

Antibodies.

Chicken anti-Calreticulin (ER) polyclonal Ab (ab14234, Abcam, Cambridge, Mass.), biotinylated donkey anti-rabbit IgG (ab6801, Abcam), HRP-conjugated donkey anti-rabbit IgG (Cat. 31458, Thermo Labsystems, Franklin, Mass.), phycoerytrin (PE)-conjugated donkey anti-goat antibody (F0107, R&D Systems, Minneapolis, Minn.), TRITC-conjugated donkey anti-chicken Ab (43R-ID057RD, Fitzgerald Industries, Acton, Mass.), Alexa flour 488-conjugated donkey anti-goat Ab (Molecular Probes, Invitrogen, Carlsbad, Calif.), Alexa flour 594-conjugated donkey anti-rabbit Ab (Molecular Probes), mouse anti-MHC I Ab (H58A, VMRD, Inc., Pullman, Wash.), and FITC-conjugated rat anti-mouse IgG (eBioscience, San Diego, Calif.) were purchased from the respective commercial sources.

Production of Anti-BHV-1 $U_L$49.5-, gM- and Anti-Bovine TAP1-Specific Polyclonal Sera: (i) Anti-BHV-1 µM-Specific Antibody.

A peptide corresponding to the predicted amino acid residues 191-205 ([H]-QAVHALRERSPRAHRC-OH; SEQ ID NO:1) of BHV-1 µM was synthesized and conjugated to polyethylene glycol as published [26,27] and used to immunize New Zealand white rabbits (Cocalico Biologicals, Reamstown, Pa.) to generate anti-BHV-1 µM serum.

Production of Anti-BHV-1 $U_L$49.5-, gM- and Anti-Bovine TAP1-Specific Polyclonal Sera: (ii) Anti-BHV-1 $U_L$49.5-Specific Antibody.

The DNA fragment corresponding to $U_L$49.5 amino acid residues 23 to 60 (Genbank Accession No. AJ004801) was cloned into pGEX-4T-2 vector and expressed in E. coli BL21 as a GST fusion protein. The $U_L$49.5-specific peptide was purified using a glutathione-sepharose column followed by thrombin protease cleavage and used to immunize rabbits (Cocalico Biologicals) as published [27].

Production of Anti-BHV-1 $U_L$49.5-, gM- and Anti-Bovine TAP1-Specific Polyclonal Sera: (iii) Anti-Bovine TAP1-Specific Antibody.

The predicted amino acid residues 117 to 167 and residues 351 to 415 (Accession No. AAY34698) of bovine TAP1 were amplified by PCR, cloned into Vector pGEX-4T-2, expressed as GST fusion proteins, and purified to immunize rabbits and goats as described above.

Cell Transfection and Generation of $U_L$49.5 Expressing Cell Line.

To generate a $U_L$49.5 expressing cell line, first the entire BHV-1 $U_L$49.5 ORF coding region ($U_L$49.5 gene) was amplified from the wild type BHV-1 Cooper strain genomic DNA by PCR and cloned into the eukaryotic expression vector, pEF6/V5-His TOPO (Invitrogen). Positive clones containing $U_L$49.5-specific sequences were identified by PCR and sequencing of the $U_L$49.5 ORF coding region. One positive $U_L$49.5-pEF6/V5-His clone DNA was transfected into MDBK cells by Lipofectamine (Invitrogen) as published [27]. Forty-eight hours after transfection, confluent cells were treated with trypsin and diluted 5-fold in DMEM containing 10 µg/ml of Blasticidin (Invitrogen) and plated in 25 cm$^2$ flasks. The Blasticidin concentration was decreased to 5 µg/ml after 7 days, and thereafter the medium was replaced every 3 days until the distinct Blasticidin-resistant colonies developed. Blasticidin-resistant clones were then isolated and analyzed for $U_L$49.5 expression by indirect immunofluorescence (IF) and immunoprecipitation assays.

Radiolabelling of Mock- or Virus-Infected MDBK Cell Proteins, SDS-PAGE and Immunoprecipitation/Immunoblotting Analysis.

[$^{35}$S] methionine-cysteine labeling of the mock- or virus-infected MDBK cells was performed as published earlier [28, 29]. Cell lysates and immunoprecipitates were denatured at 100° C. in reducing sample buffer containing β-mercaptoethanol for the $U_L$49.5 samples, and separated in a 5~20% linear gradient sodium dodecyl sulfate-polyacrylamide gel (SDS-PAGE) [23]. However, for gM and TAP1 analyses, cell lysates and immunoprecipitates were incubated at 56° C. in reducing sample buffer with 100 mM dithiothreitol (DTT) and then loaded on a 5~20% linear gradient or 10% SDS-PAGE respectively [22, 23, 28].

Construction of BHV-1 $U_L$49.5 Cytoplasmic Tail Null Virus (BHV-1 $U_L$49.5 CT-Null BAC).

A two-step Red-mediated mutagenesis protocol was followed as published earlier [30] to construct a $U_L$49.5 cytoplasmic tail null virus. Briefly, primers for $U_L$49.5 CT-null-forward (for) and $U_L$49.5 CT-null-reverse (rev) (SEQ ID NO:2 and SEQ ID NO:3, respectively) were designed to delete 7 nucleotides of $U_L$49.5 ORF (238 to 244, AGGCTCA) and to mutate the nucleotides 246-247 (GG) to AA (FIGS. 2 and 3, Table 1). The PCR amplified I-SceI/aphAI cassette was digested with Dpn I, purified and electroporated together with pBAD-I-SceI DNA into SW105 competent cells harboring pBHV-1 WT BAC for 1$^{st}$ recombination as published earlier [30-32]. Several kanamycin-sensitive colonies were obtained after the 2$^{nd}$ recombination. Finally, positive pBHV-1 BAC $U_L$49.5 CT-null colonies were identified by PCR and sequencing of the $U_L$49.5 ORF in the putative mutant colonies. The BAC-excised BHV-1 $U_L$49.5 CT-null virus was generated from a pBHV-1 BAC $U_L$49.5 CT-null clone by Cre-mediated BAC excision as described earlier [30-32].

TABLE 1

PCR primers used for generation of BHV-1 $U_L$49.5 mutants and for colony identification

| Primer | Sequence (5' to 3') |
| --- | --- |
| Mutagenesis$^a$ | |
| CT-null For (SEQ ID NO: 2) | 5'-AATGGTCGCCGTGGCCCTGTACGCGTACGGGCTTTGCTTTTAAGCGCCAGCGGGCCCAATaggatgacgacgataagtaggg-3' |
| CT-null Rev (SEQ ID NO: 3) | 5'-CGCCCCGCGACTCCTTTTTATTGGGCCCGCTGGCGCTTAAAAGCAAAGCCCGTACGCGTcaaccaattaaccaattctgattag-3' |
| Δ30-32 For (SEQ ID NO: 4) | 5'-TGCCATCGTGCGCGGCCGCGACCCCCTGCTAGACGCGATGGGGGCAATGGACTTTTGGAGaggatgacgacgataagtaggg-3' |
| Δ30-32 Rev (SEQ ID NO: 5) | 5'-CGCGCGCGTAGCAGCCTGCGCTCCAAAAGTCCATTGCCCCCATCGCGTCTAGCAGGGGGTcaaccaattaaccaattctgattag-3' |
| Δ37-40 For (SEQ ID NO: 6) | 5'-ACCCCCTGCTAGACGCGATGCGGCGCGAGGGGGCAATGGACGGCTGCTACGCGCGCGGGGTaggatgacgacgataagtaggg-3' |
| Δ37-40 Rev (SEQ ID NO: 7) | 5'-GCGGTGGCTCCGAGAGCGGCACCCCGCGCGCGTAGCAGCCGTCCATTGCCCCCTCGCGCCcaaccaattaaccaattctgattag-3' |
| Δ43-46 For (SEQ ID NO: 8) | 5'-ATGCGGCGCGAGGGGGCAATGGACTTTTGGAGCGCAGGCTGCGTGCCGCTCTCGGAGCCACCaggatgacgacgataagtaggg-3' |
| Δ43-46 Rev | 5'-TAAAAAACAACCAGGGCCTGCGGTGGCTCCGAGAGCGGCACGCAGCCTGCGCTCCAAAAGTcaaccaattaaccaattctg |

TABLE 1-continued

PCR primers used for generation of BHV-1 U_L49.5 mutants and for colony identification

| Primer | Sequence (5' to 3') |
|---|---|
| (SEQ ID NO: 9) | attag-3' |
| 30aaa32 For (SEQ ID NO: 10) | 5'-TGCCATCGTGCGCGGCCGCGACCCCCTGCTAGACGCGATGgcggccgcgGGGGCAATGGACTTTTGGAGaggatgacg acgataagtaggg-3' |
| 30aaa32 Rev (SEQ ID NO: 11) | 5'-CGCGCGCGTAGCAGCCTGCG*CTCCAAAAGTCCATTGCCCC*cgcggccgc*CATCGCGTCTAGCAGGGGGT*caaccaat taaccaattctgattag-3' |
| Colony PCR[b] | | | |
| U_L49.5 For | agagcgccagcgagtcgggctc (SEQ ID NO: 12) | d30-32 SRev | agtccattgccccCTCGCGCCG (SEQ ID NO: 13) |
| d37-40 SRev | gcgcgcgtagcagccTGCGCT (SEQ ID NO: 14) | d43-46 SRev | ctccgagagcggcacCCCGC (SEQ ID NO: 15) |

[a]BHV-1 UL49.5-specific sequences are shown in uppercase letter; the italicized and italicized-underlined sequences are complementary to each other in inverse orientation. Nucleotides in lowercase indicated the pEPkan-S-specific sequences.
[b]Primers used for identification of BHV-1 UL49.5 BAC mutants form the selected kanamycin-sensitive colonies by PCR. The bold letters indicate the reverse complement sequences corresponding to the deleted UL49.5 nucleotides respectively.

BAC Mutagenesis to Incorporate Short Deletions or Alanine Substitutions Within $U_L49.5$ Luminal Domain.

As shown in Table 1, primer pairs specific for short sequence deletion at $U_L49.5$ amino acid residues 30 to 32 ($U_L49.5\Delta30$-32), 37 to 40 ($U_L49.5\Delta37$-40), and 43 to 46 ($U_L49.5\Delta43$-46) or alanine substitutions at residues 30 to 32 ($U_L49.5$ 30AAA32) were synthesized. The PCR products were amplified, purified, and electroporated into the SW105 competent cells harboring pBHV-1 BAC (wt) or pBHV-1 BAC $U_L49.5$ CT-null for 1$^{st}$ recombination, and 2$^{nd}$ recombination was performed as described above. Reconstituted BAC containing or BAC-excised mutant viruses were then generated as published earlier [30-32]. BAC-excised $U_L49.5$ mutant viruses were plaque purified and designated as BHV-1 $U_L49.5\Delta30$-32, BHV-1 $U_L49.5$ 30AAA32, BHV-1 $U_L49.5\Delta30$-32 CT-null, BHV-1 $U_L49.5$ 30AAA32 CT-null, BHV-1 $U_L49.5\Delta37$-40 CT-null, and BHV-1 $U_L49.5\Delta43$-46 CT-null, respectively.

Viral Growth Kinetics and Plaque Size Determination.

One step growth curve assays were performed as published earlier [25, 33]. Average plaque size was calculated by measuring 50 randomly selected plaques for each mutant virus (under a microscope with a graduated ocular objective).

TAP1 and $U_L49.5$ Intracellular Staining and Laser Scanning Confocal Microscopy.

MDBK cells grown on permanox chamber slides (Cole-Parmer, Vernon Hills, Ill.) were infected with wt BHV-1 or BHV-1 $U_L49.5$ mutant viruses. Cells were fixed at different times post-infection with freshly prepared 1% paraformaldehyde in PBS, permeabilized with FACS permeabilizing solution, and blocked with 2% IgG free bovine serum albumin. The cells were incubated (for 60 min) with a cocktail of goat anti-bovine TAP1 (1:800), rabbit anti-$U_L49.5$ (1:3200) and chicken anti-Calreticulin (ER) (1:3200) antibodies, washed, and subsequently stained (for 15 min) with a cocktail of Alexa flour 488-conjugated donkey anti-goat (1:2000), TRITC-conjugated donkey anti-chicken (1:2000), and Alexa flour 594-conjugated donkey anti-rabbit (1:2000) antibodies. After 5 washes, coverslips were mounted onto slides and examined with a Zeiss LSM510 laser scanning confocal microscopy using 20× and 40× objectives. Cellular ER-, bovine TAP1- and $U_L49.5$-specific labeling was excited at laser wavelengths of 410 nm, 517 nm, and 617 nm, respectively.

Analysis of Peptide Transport in the BHV-1 $U_L49.5$ Mutants-Infected Cells.

MDBK cells grown on 6-well plate were infected at a MOI of 10 with BHV-1 wt, BHV-1 $U_L49.5$ CT-null and various $U_L49.5$ luminal domain mutant viruses. At different timepoints (2, 5, and 8 hours post infection (hpi)), the cells were trypsinized, permeabilized, and incubated with 5 µl of Phycoerythrin-conjugated mouse anti-calreticulin (anti-ER) MAb (Clone FMC 75, Abcam) and the FITC-conjugated synthetic peptide, SVNKTERAY, in the absence and presence of ATP (10 mM, Sigma) for 20 min at 37° C. in the dark. The cells were fixed after three washes and analyzed for fluorescence intensity by a FACS Calibur flow cytometer. At least 30,000 gated events based on forward and side scatters and pulse width were analyzed using Summit Data Acquisition and Analysis software (DakoCytomation, Glostrup, Denmark). The mock infected MDBK cells served as a control.

Detection of MHC-I Expression on the Infected Cell Surface by FACS.

Approx. $10^6$ of MDBK cells either mock infected or infected (1 MOI) with BHV-1 wt, BHV-1 $U_L49.5$ CT-null, or individual BHV-1 mutant virus were collected at 12 or 18 hpi, blocked with IgG free BSA, and incubated (for 20 min) with mouse anti-bovine MHC I antibody (Ab). After PBS washes, cells were incubated with 5 µl of FITC-conjugated rat anti-mouse Ab and fixed with 2% formalin and then analyzed by flow cytometer. The stained cells were gated based on forward and side scatters and pulse width. At least 30,000 gated events were analyzed using Summit Data Acquisition and Analysis Software (DakoCytomation) as previously published [35]. MDBK cells infected similarly with the respective viruses were stained by FITC-conjugated mouse IgG2a and used as the isotype controls.

Example 2

BHV-1 $U_L49.5\Delta30$-32 CT-Null Construction and Characterization

A BHV-1 $U_L49.5$ CT-null mutant virus was constructed by deletion of 7 nucleotides (238-AGGCTCA-244) and mutation of nucleotides 246G and 247G to AA to introduce a strong stop codon, TAA (See FIGS. 1A, 2 and 3). FIG. 1A gives the predicted amino acid (aa) sequence of BHV-1 $U_L49.5$ open reading frame (ORF), with the bold letters indicating the $U_L$49.5 cytoplasmic tail residues and the underlined region indicating the $U_L$49.5 luminal domain residues. In the $U_L$49.5Δ30-32 CT-null mutant, the $U_L$49.5 residues 30RRE32 of the luminal domain were deleted, along with the $U_L$49.5 cytoplasmic tail residues 80RL81. In addition, $U_L$49.5 residues 82M through 96G are not expressed due to an amber mutation replacing the 82M to a stop codon. FIG. 2 shows the DNA sequence of wild type BHV-1 $U_L$49.5 and the changes to generate the mutant BHV-1 $U_L$49.5 CT-null, i.e., the deletion of nucleotides 238 to 244 and the mutation of nucleotides 246 and 247 to AA to introduce a strong stop codon TAA. The primers used in making the mutant viruses are shown in Table 1, and schematics of the PCR primers used to make BHV-1 $U_L$49.5 CT-null and BHV-1 $U_L$49.5Δ30-32 CT-null are shown in FIGS. 3 and 4, respectively.

Based on an alignment of predicted amino acid sequences of $U_L$49.5 luminal domains of several animal alpha herpesviruses; BHV-1, pseudorabiesvirus (PRV, Accession No. U38547.1), equine herpesvirus 1 type (EHV-1, Accession No. AY665713.1), equine herpesvirus type 4 (EHV-4, Accession No. NC_001844), and canine herpesvirus (CHV, Patent EPO 910406), a BHV-1 luminal domain motif $U_L$49.5 30-RX-EXXXXFW-XXXCXXXG-46 was found to be conserved within the corresponding $U_L$49.5 luminal domains of several alpha herpesviruses (Data not shown). To determine whether any of these conserved sequences are functionally important for TAP inhibition, several BHV-1 $U_L$49.5 luminal domain mutants in wild-type (wt) and $U_L$49.5 CT-null backbone were designed and constructed (FIG. 1C). To determine the role of residues 30-32 alone in TAP inhibition and TAP degradation, both $U_L$49.5Δ30-32 and alanine exchanged ($U_L$49.5 30AAA32) mutants, later, were constructed in the BHV-1 wt backbone (FIG. 1D).

BAC excised BHV-1 $U_L$49.5 mutant viruses were analyzed by immunoprecipitation and/or immunoblotting to determine molecular mass and level of mutant $U_L$49.5 expression, incorporation of the mutant $U_L$49.5 in the envelope, and effect of $U_L$49.5 mutation on gM processing or $U_L$49.5/gM interaction. FIG. 5 shows the results of the immunoblotting analysis of mutant $U_L$49.5 expressed in the infected cells and incorporated in the virion envelope by various $U_L$49.5 mutant viruses, including uninfected (Mock), BHV-1 wt, BHV-1 $U_L$49.5 CT-null, BHV-1 $U_L$49.5Δ30-32 CT-null, BHV-1 $U_L$49.5Δ37-40 CT-null, BHV-1 $U_L$49.5Δ43-46 CT-null, BHV-1 $U_L$49.5 30AAA32 CT-null, BHV-1 $U_L$49.5Δ30-32, and BHV-1 $U_L$49.5 30AAA32. The virus infected cell lysates or partially purified virions were separated by a 10-20% gradient SDS-PAGE and incubated with rabbit anti-BHV-1 α-$U_L$49.5 specific Ab. Equal amounts of the extracted cell lysates or virions were loaded, and the α-tublin was used as a control.

As shown in FIG. 5, relative to wt $U_L$49.5 (with an approximate molecular mass of 10 kDa), the approximate molecular mass of the CT-null $U_L$49.5 is 8 kDa, which is consistent with the predicted molecular mass of $U_L$49.5 lacking the C-terminal 17 aa residues. For the BHV-1 $U_L$49.5Δ30-32 CT-null, BHV-1 $U_L$49.5Δ37-40 CT-null, BHV-1 $U_L$49.5Δ43-46 CT-null, and BHV-1 $U_L$49.5 30AAA32 CT-null viruses, all have a $U_L$49.5 with molecular mass of approximately 8 kDa which is similar to the parental virus BHV-1 $U_L$49.5 CT-null. However, the BHV-1 $U_L$49.5Δ30-32 and $U_L$49.5 30AAA32 (both on a wt backbone) have an approximate molecular mass of 10 kDa similar to wt $U_L$49.5 (FIG. 5). Importantly, all mutant $U_L$49.5 proteins were incorporated into their respective virion envelopes (FIG. 5).

Figure 6:
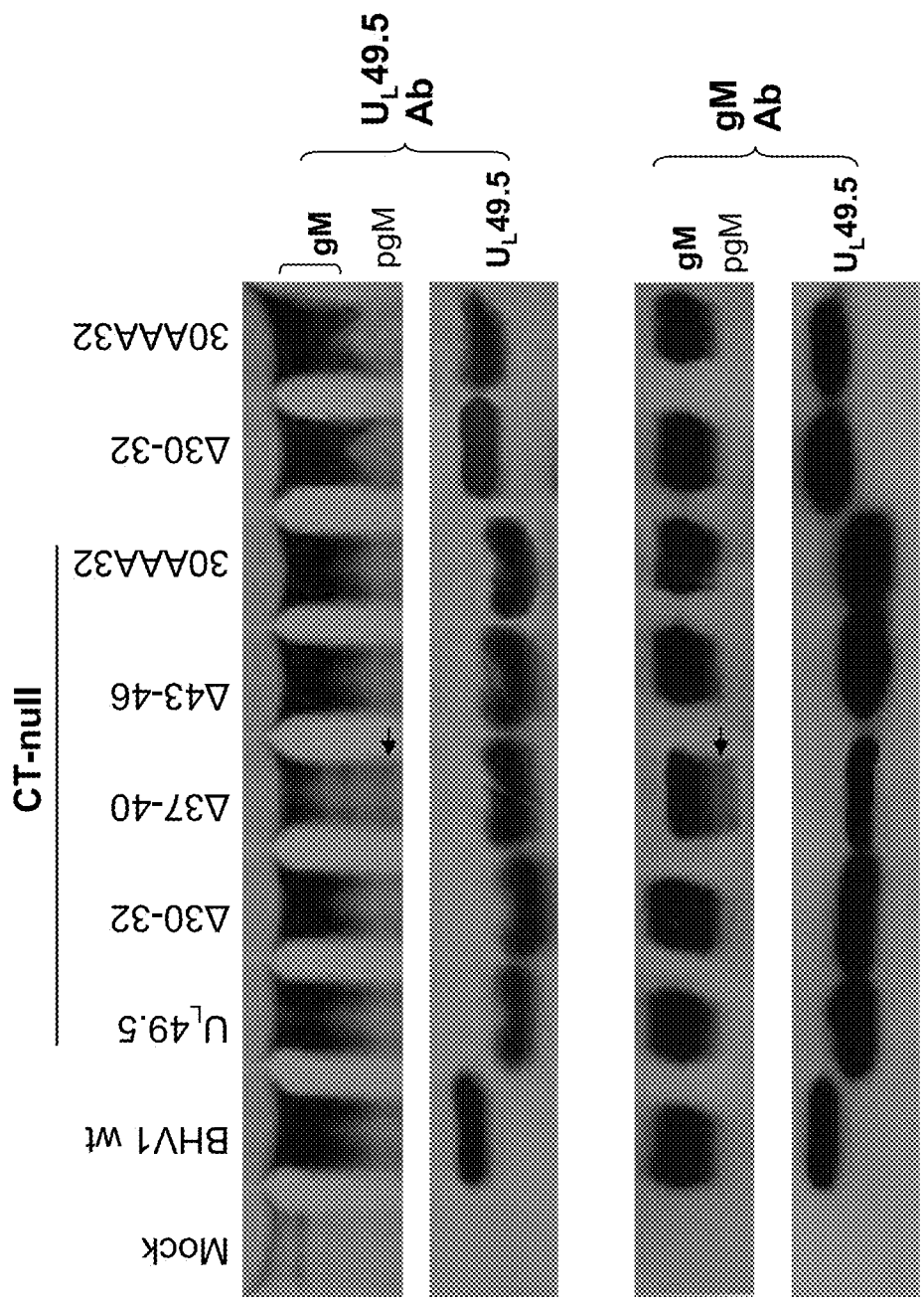
FIG. 6 illustrates the results of an analysis of gM-$U_L49.5$ interaction by radioimmunoprecipitation assay (RIPA). $^{35}$S-labeled lysates from the mock-infected or virus-infected MDBK cells (uninfected (Mock), BHV-1 wt, BHV-1 CT-null, BHV-1 $U_L49.5\Delta30$-32 CT-null, BHV-1 $U_L49.5\Delta37$-40 CT-null, BHV-1 $U_L49.5\Delta43$-46 CT-null, BHV-1 $U_L49.5$ 30AAA32 CT-null, BHV-1 $U_L49.5\Delta30$-32, and BHV-1 $U_L49.5$ 30AAA32 were immuno-precipitated with rabbit anti $U_L49.5$- (top two panels) or anti gM-specific polyclonal serum (bottom two panels), separated by SDS-PAGE, and visualized by autoradiography. Unprocessed gM (pgM, marked with an arrow) and processed gM are marked.

FIG. 6 illustrates the gM-$U_L$49.5 interaction by radioimmunoprecipitation assay (RIPA). $^{35}$S labeled lysates from the mock-infected or virus-infected MDBK cells (uninfected (Mock), BHV-1 wt, BHV-1 $U_L$49.5 CT-null, BHV-1 $U_L$49.5Δ30-32 CT-null, BHV-1 $U_L$49.5Δ37-40 CT-null, BHV-1 $U_L$49.5Δ43-46 CT-null, BHV-1 $U_L$49.5 30AAA32 CT-null, BHV-1 $U_L$49.5Δ30-32, and BHV-1 $U_L$49.5 30AAA32) were immunoprecipitated with rabbit anti $U_L$49.5- (top two panels) or anti gM-specific polyclonal serum (bottom two panels) and separated by SDS-PAGE and visualized by autoradiography.

As shown in FIG. 6, these results of immunoprecipitation using $U_L$49.5- or gM-specific rabbit polyclonal antibodies show that: (i) amounts of wt and mutant $U_L$49.5 ($U_L$49.5 CT-null, $U_L$49.5Δ30-32 CT-null, $U_L$49.5Δ43-46 CT-null, and $U_L$49.5Δ37-40 CT-null) immunoprecipitated by anti $U_L$49.5 antibody in each case were very similar (FIG. 6), (ii) the amount and molecular mass of mature gM coimmunoprecipitated by the anti-$U_L$49.5 antibody from infected cell lysates of BHV-1 wt, BHV-1 $U_L$49.5 CT-null, BHV-1 $U_L$49.5Δ30-32 CT-null, and BHV-1 $U_L$49.5Δ43-46 CT-null viruses were very similar; but in the case of BHV-1 $U_L$49.5Δ37-40 CT-null, the amount of processed (mature) gM coimmunoprecipitated was reduced (FIG. 6); and (iii) consistent with the latter results, with the exception of BHV-1 $U_L$49.5Δ37-40 CT-null, anti gM antibody coimmunoprecipitated similar amounts of $U_L$49.5 from the all the virus-infected cell lysates. In the case of BHV-1 $U_L$49.5Δ37-40 CT-null, the amount of $U_L$49.5 coimmunoprecipitated was reduced; and additionally, there was an increase in the amount of unprocessed gM (FIG. 6).

Taken together, these results indicated that the mutant viruses have essentially normal $U_L$49.5 expression and all but one mutant ($U_L$49.5Δ37-40 CT-null) have a normal gM processing and $U_L$49.5/gM interaction. The BHV-1 $U_L$49.5Δ37-40 CT-null virus had slightly defective gM processing and $U_L$49.5/gM interaction.

Example 3

Figure 7A:
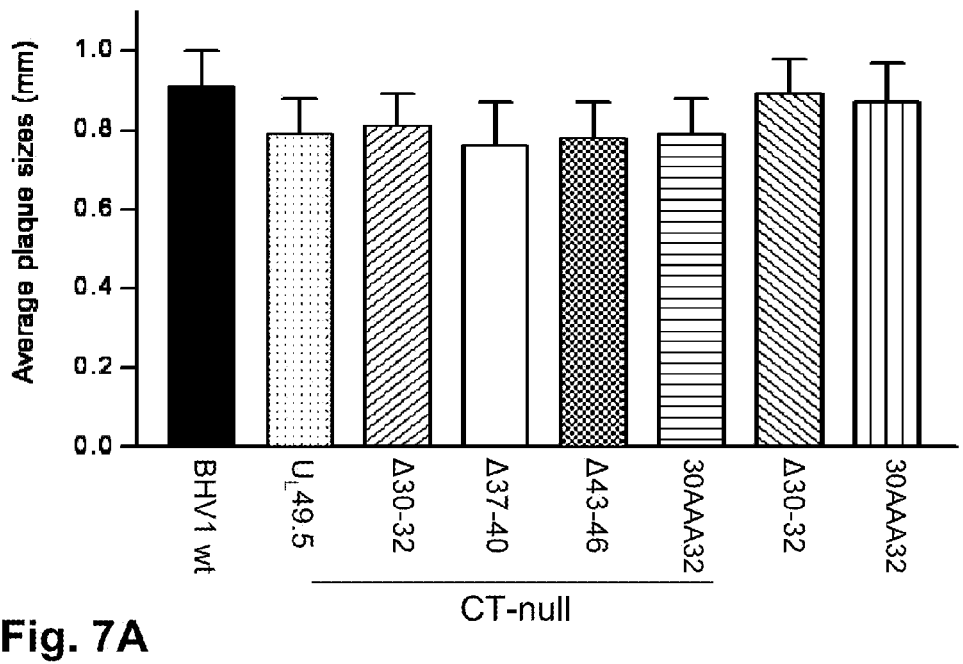
FIG. 7A illustrates the average plaque size measured at 48 h post infection (hpi) of various BHV-1 $U_L$49.5 mutants (BHV-1 wt, BHV-1 CT-null, BHV-1 $U_L$49.5Δ30-32 CT-null, BHV-1 $U_L$49.5Δ37-40 CT-null, BHV-1 $U_L$49.5Δ43-46 CT-null, BHV-1 $U_L$49.5 30AAA32 CT-null, BHV-1 $U_L$49.5Δ30-32, and BHV-1 $U_L$49.5 30AAA32) in MDBK cells. Average plaque diameters of 50 randomly selected plaques are shown as mean±standard deviation.
Figure 7B:
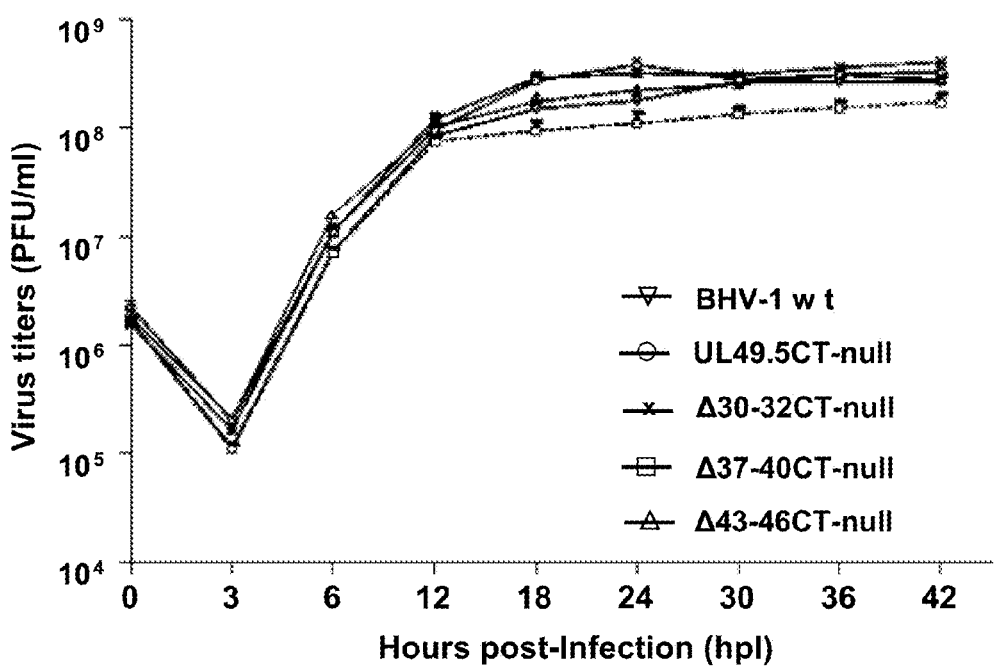
FIG. 7B illustrates the one-step growth kinetics of BHV-1 wt and three representative BHV-1 $U_L$49.5 mutants ($U_L$49.5Δ30-32, $U_L$49.5Δ37-40 and $U_L$49.5Δ43-46) in the CT-null backbone. Each data point represents the average of duplicate samples obtained from separate infections.

Growth Characteristics of Reconstituted $U_L$49.5 Mutant Viruses In Vitro in MDBK Cells FIG. 7A illustrates the average plaque size measured at 48 h post infection (hpi) of various BHV-1 $U_L$49.5 mutants (BHV-1 wt, BHV-1 $U_L$49.5 CT-null, BHV-1 $U_L$49.5Δ30-32 CT-null, BHV-1 $U_L$49.5Δ37-40 CT-null, BHV-1 $U_L$49.5Δ43-46 CT-null, BHV-1 $U_L$49.5 30AAA32 CT-null, BHV-1 $U_L$49.5Δ30-32, and BHV-1 $U_L$49.5 30AAA32) in MDBK cells. Average plaque diameters of 50 randomly selected plaques are shown as mean±standard deviation. The average plaque sizes shown in FIG. 7A demonstrated that all BHV-1 $U_L$49.5 mutants had virtually similar plaque sizes when compared with BHV-1 wt.

To examine whether the various deletions within the luminal domain affected viral replication kinetics and virus yield in infected MDBK cells, one-step growth properties of the various $U_L$49.5 mutants were determined. FIG. 7B illustrates the one-step growth kinetics of BHV-1 wt and three representative BHV-1 $U_L$49.5 mutants ($U_L$49.5Δ30-32, $U_L$49.5Δ37-40 and $U_L$49.5Δ43-46) in the CT-null backbone. Each data point represents the average of duplicate samples obtained from separate infections. Note that BHV-1 $U_L$49.5Δ37-40 CT-null exhibited slightly delayed viral replication kinetics between 12 to 42 hpi. The graph of the one step growth kinetics shown in FIG. 7B shows that all BHV-1 $U_L$49.5 mutants had virtually similar growth kinetics when compared with BHV-1 wt.

Example 4

Peptide Transport in BHV-1 $U_L49.5$ Mutant Virus-Infected Cells

Figure 8A:
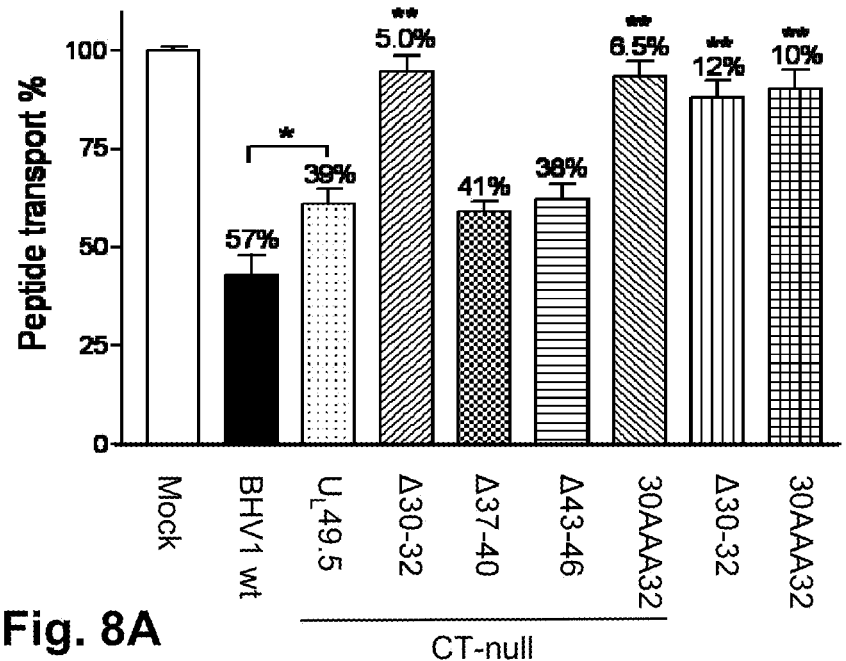
FIG. 8A illustrates the results of an analysis of transporter associated with antigen processing (TAP) peptide transport function in various BHV-1 $U_L$49.5 mutant-infected cells. The mock-, BHV-1 $U_L$49.5 wt or various BHV-1 $U_L$49.5 mutant virus-infected MDBK cells (10 MOI) were harvested at 5 h post infection. The percentage above the bars denotes the decreased peptide-specific FITC (fluorescein isothiocyanate) intensity for each sample as compared with the mock-infected cells, and the statistical significance is indicated by stars: *, P<0.05, **, P<0.01.
Figure 8B:
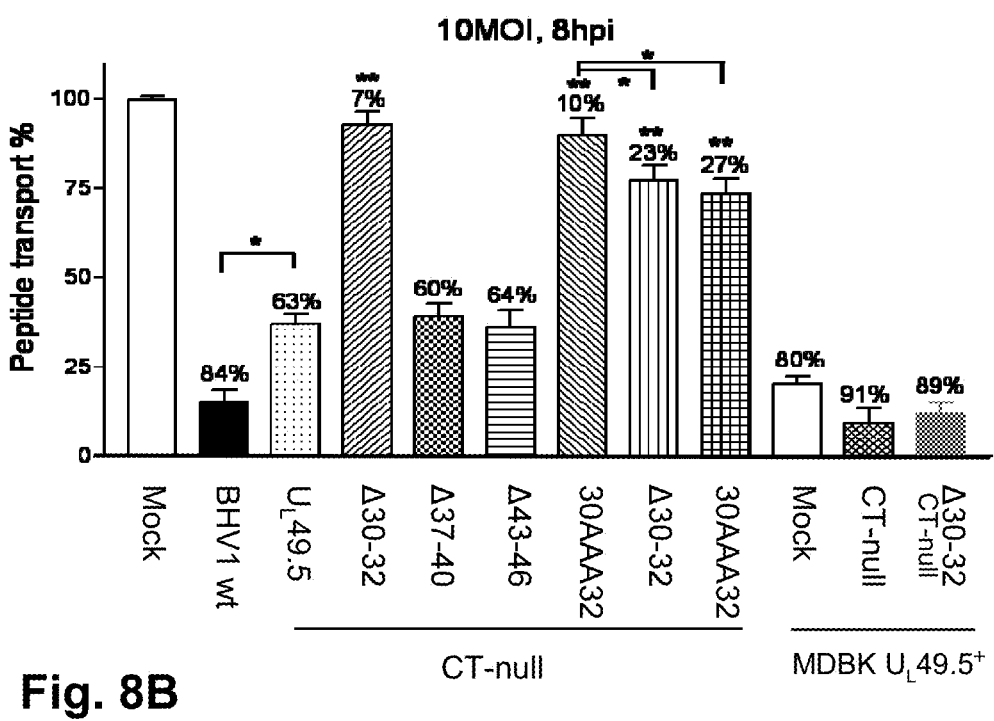
FIG. 8B illustrates the results of an analysis of transporter associated with antigen processing (TAP) peptide transport function in various BHV-1 $U_L$49.5 mutant-infected cells. The mock-, BHV-1 $U_L$49.5 wt or various BHV-1 $U_L$49.5 mutant virus-infected MDBK cells (10 MOI) were harvested at 8 h post infection. The percentage above the bars denotes the decreased peptide-specific FITC (fluorescein isothiocyanate) intensity for each sample as compared with the mock-infected cells, and the statistical significance is indicated by stars: *, P<0.05, **, P<0.01.

Peptide transport was assessed, in the presence (FIGS. 8A and 8B) and absence of ATP (data not shown), in mock-infected MDBK cells and MDBK-$U_L$49.5+ cells or as infected with BHV-1 wt, BHV-1 $U_L$49.5 CT-null and individual BHV-1 $U_L$49.5 mutant viruses. In addition, peptide transport was determined in mock-infected MDBK cells (FIGS. 8A and 8B), mock-infected MDBK-$U_L$49.5$^+$ cells, and BHV-1 $U_L$49.5 mutant virus-infected MDBK-$U_L$49.5$^+$ cells (FIGS. 8A and 8B). FIG. 8B illustrates the results of an analysis of transporter associated with antigen processing (TAP) peptide transport function in various BHV-1 $U_L$49.5 mutant-infected cells at 5 hours past infection (hpi) and 8 hpi, respectively. The percentage above the bars denotes the decreased peptide-specific FITC (fluorescein isothiocyanate) intensity for each sample when compared with the mock-infected cells, and the statistical significance is indicated by stars: *, P<0.05, **, P<0.01. At 5 hpi, the effect of $U_L$49.5 mutations on peptide transport in BHV-1 $U_L$49.5 mutant virus-infected cells, relative to BHV-1 wt-infected cells, was noticeable, but the effects were more prominent at 8 hpi (Comparing FIG. 8A (5 hpi) to FIG. 8B (8 hpi)). Relative to peptide transport in BHV-1 wt-infected MDBK cells at 8 hpi, peptide transport in cells infected with: (i) BHV-1 $U_L$49.5Δ30-32 and BHV-1 $U_L$49.5 30AAA32 was increased 4 fold (23% and 27% inhibition, respectively versus 84% inhibition for the wt; P<0.01); (ii) BHV-1 $U_L$49.5 CT-null was increased 2.5 fold (63% inhibition versus 84% for the wt; P<0.05); and (iii) BHV-1 $U_L$49.5Δ30-32 CT-null or BHV-1 $U_L$49.5 30AAA32 CT-null was increased to about 6 fold (7% and 10% inhibition, respectively versus 84% for the wt; P<0.01) (FIG. 8B). Since there was also an additional 1.2-1.5 fold increase of peptide transport in BHV-1 $U_L$49.5Δ30-32 CT-null-/BHV-1 $U_L$49.5 30AAA32 CT-null-infected cells compared with the corresponding BHV-1 $U_L$49.5Δ30-32/BHV-1 $U_L$49.5 30AAA32 cells (7%/10% versus 23%/27% inhibition, respectively)(FIG. 8B), the increase in peptide transport due to the $U_L$49.5 CT sequence deletion alone was significant (P<0.05). As expected, in the absence of ATP, there was no peptide transport in either wt or mutant-viruses infected MDBK cells (data not shown).

Regardless of BHV-1 $U_L$49.5Δ30-32 or BHV-1 $U_L$49.5Δ30-32 CT-null or BHV-1 $U_L$49.5 CT-null virus infection, peptide transport in infected MDBK-$U_L$49.5$^+$ cells was inhibited to almost wt $U_L$49.5 level (~90%) (FIG. 8B). Therefore, the relative increase in peptide transport in MDBK cells infected with BHV-1 $U_L$49.5 mutants with residues 30-32- deleted or substituted with alanine and BHV-1 $U_L$49.5 CT-null virus is due to the lack of $U_L$49.5 residues important for TAP mediated peptide transport function.

Example 5

Figure 9A:
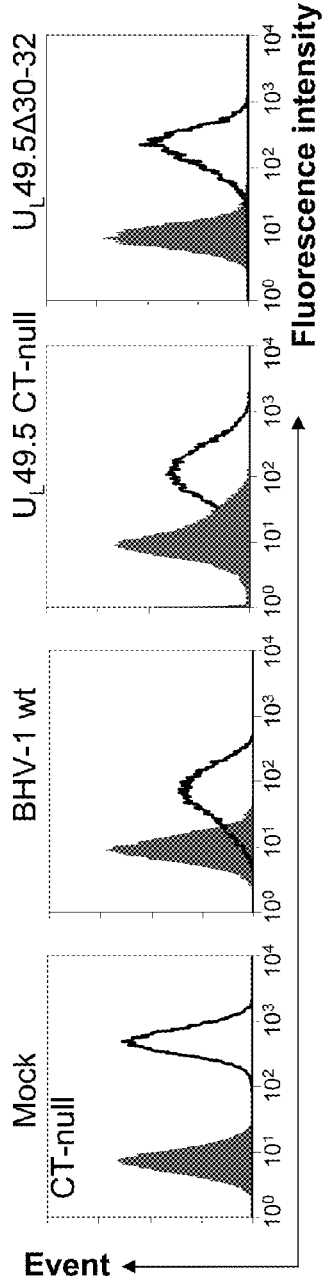
FIG. 9A illustrates representative fluorescence activated cell sorter (FACS) histograms showing the profile of MHC-I expression in the mock-, BHV-1 wt-, BHV-1 $U_L$49.5 CT-null- and BHV-1 $U_L$49.5Δ30-32 CT-null-infected cell surface. Normal mouse IgG2a served as an isotype-matched control (filled curve). Infected MDBK cells or $U_L$49.5-expressing MDBK-$U_L$49.5+ cells were stained with anti-MHC-I Ab, subsequently incubated with FITC-conjugated rat anti-mouse IgG, and subjected to FACS analysis.
Figure 9B:
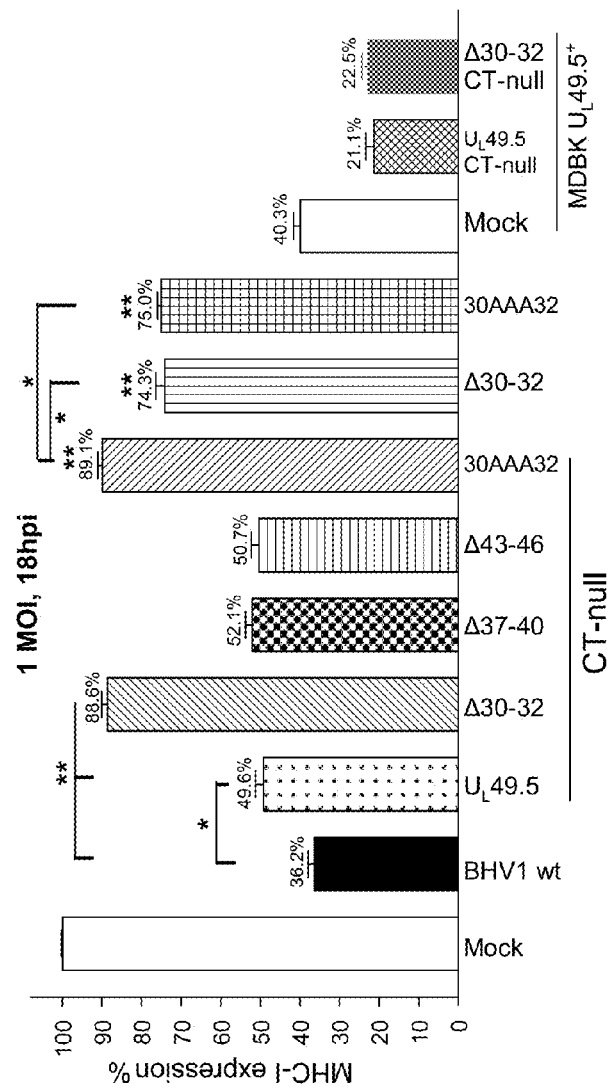
FIG. 9B illustrates the means of three independent experiments using fluorescence activated cell sorter (FACS) for MHC-I expression on the MDBK cells or MDBK-$U_L$49.5+ cells infected with BHV-1 wt, or various BHV-1 $U_L$49.5 mutant viruses. Infected MDBK cells or $U_L$49.5 expressing MDBK-$U_L$49.5+ cells were stained with anti-MHC-I Ab, subsequently incubated with FITC-conjugated rat anti-mouse IgG, and subjected to FACS analysis. The statistical significance is indicated by stars: *, P<0.05, **, P<0.01.

MHC Class I Cell-Surface Expression in BHV-1 $U_L$49.5 Mutants-Infected Cells Experiments were conducted to determine if MHC-I cell surface expression was increased in MDBK cells infected with BHV-1 $U_L$49.5 luminal domain mutants. FIG. 9A illustrates representative fluorescence activated cell sorter (FACS) histograms showing the profile of MHC-I expression in the mock-, BHV-1 wt-, BHV-1 $U_L$49.5 CT-null- and BHV-1 $U_L$49.5Δ30-32 CT-null-infected cell surface. Normal mouse IgG2a served as an isotype-matched control (filled curve). Infected MDBK cells or $U_L$49.5-expressing MDBK-$U_L$49.5+ cells were stained with anti-MHC-I Ab, subsequently incubated with FITC-conjugated rat anti-mouse IgG and subjected to FACS analysis. FIG. 9B shows the means of three independent experiments from the data produced by FACS as shown in FIG. 9A. The statistical significance is indicated by stars: *, P<0.05, **, P<0.01.

As shown in FIGS. 9A and 9B, compared with BHV-1 wt-infected MDBK cells, MHC-I surface expression was increased: (i) in BHV-1 $U_L$49.5Δ30-32- and BHV-1 $U_L$49.5 30AAA32-infected MDBK cells by 2 fold (74.3% and 75.0%, respectively versus 36.2% for the wt; P<0.01); (ii) in BHV-1 $U_L$49.5Δ30-32 CT-null- and BHV-1 $U_L$49.5 30AAA32 CT-null-infected MDBK cells by 2.5 fold (88.6% and 89.1%, respectively versus 36.2% for the wt; P<0.01); and (iii) in BHV-1 $U_L$49.5 CT-null-infected cells by 1.3 fold (49.6% versus 36.2% for the wt; P<0.05). Since a similar 1.2-1.3 fold increase in MHC-I surface expression was also obtained in BHV-1 $U_L$9.5Δ30-32 CT-null- and BHV-1 $U_L$49.5 30AAA32 CT-null-compared with BHV-1 $U_L$49.5Δ30-32 and BHV-1 $U_L$49.5 30AAA32-infected cells (88.6%/89% versus 74.3%/75%), the increase in MHC-I expression due to the deletion of $U_L$49.5 CT sequences alone was significant (P<0.05).

In MDBK-$U_L$49.5$^+$ cells, regardless of BHV-1 $U_L$49.5 CT-null or BHV-1 $U_L$49.5Δ30-32 CT-null virus infection, MHC-I cell-surface expression was down-regulated like in wt BHV-1-infected MDBK cells (FIG. 9B). Therefore, the relative increase in MHC-I surface expression observed for the mutant viruses is due to the effect of specific $U_L$49.5 mutation(s) and is consistent with the peptide transport data obtained for respective mutants with wt or $U_L$49.5 CT-null backgrounds. Taken together, even though $U_L$49.5 residues 30-32 are essential for TAP mediated peptide transport and MHC-I down-regulation, $U_L$49.5 CT residues are important to express full potential of $U_L$49.5-mediated TAP inhibition and MHC-I down-regulation function.

Example 6

Figure 10:
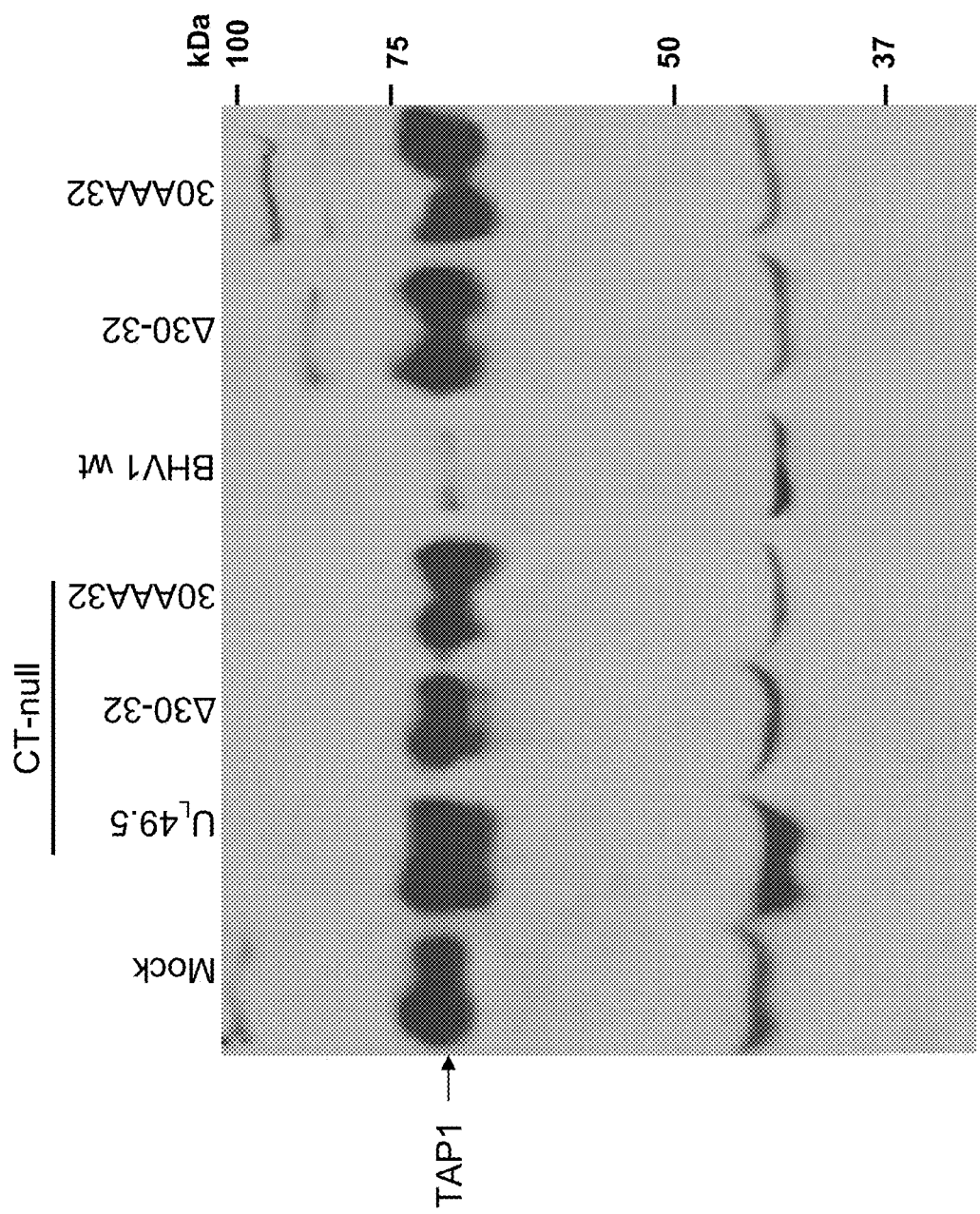
FIG. 10 illustrates the results of an immunoprecipitation/immunoblotting analysis of cellular TAP1. Mock- or various virus-infected cell lysates were immunoprecipitated with goat anti-bovine TAP1-specific antibody followed by immunoblotting with diluted (1:200) rabbit anti-TAP1 polyclonal serum, and then developed by enhanced chemiluminescent substrate.

Status of TAP1 Molecules in the BHV-1 wt Versus BHV-1 $U_L$49.5 CT-Null, BHV-1 $U_L$49.5Δ30-32 and BHV-1 $U_L$49.5 30AAA32 Mutants-Infected Cells In the BHV-1 $U_L$49.5 CT-null virus-infected cells, TAP1 is not degraded [15]. Experiments were conducted to determine the effect of $U_L$49.5Δ30-32 and $U_L$49.5 30AAA32 mutations alone on the status of TAP1 in the respective mutant virus-infected cells compared with the $U_L$49.5 CT-null and wt $U_L$49.5. Mock- or various virus-infected cell lysates were immunoprecipitated with undiluted goat anti-bovine TAP1 specific antibody followed by immunoblotting with diluted (1:200) rabbit anti-TAP1 polyclonal serum, and then developed by enhanced chemiluminescence. The results are shown in FIG. 10. An approximately 70 kDa TAP1 specific band is detectable in the mock-, BHV-1 $U_L$49.5 CT-null-, BHV-1 $U_L$49.5Δ30-32 CT-null, BHV-1 $U_L$49.5 30AAA32 CT-null-, BHV-1 $U_L$49.5Δ30-32-, and BHV-1 $U_L$49.5 30AAA32-infected cell lysates, but not in the case of BHV-1 wt. Note that in case of BHV-1 wt virus-infected lysate TAP1-specific ~70 kDa band is mostly degraded. A 45 kDa (approx.) non-specific protein is also immunoprecipitated and recognized in the immunoblot by the TAP1-specific antibodies in all the samples including the BHV-1 wt. Relative amount of 45 kDa protein immunoprecipitated from each cell lysate sample can be viewed as loading control. Since TAP1 was degraded only in BHV-1 wt infected MDBK cells but not in BHV-1 $U_L49.5$ CT-null-, BHV-1 $U_L49.5\Delta30$-32, BHV-1 $U_L49.5$ 30AAA32, BHV-1 $U_L49.5$ 30AAA32 CT-null-infected MDBK cells (FIG. 10), both $U_L49.5$ residues 30-32 and $U_L49.5$ cytoplasmic tail sequences are important for $U_L49.5$-mediated TAP degradation.

To determine the subcellular localization of the mutant $U_L49.5$ proteins relative to wt $U_L49.5$ protein in the virus-infected cells and to determine the status of TAP1 degradation and co-localization of TAP1 with respect to the mutant $U_L49.5$, confocal microscopy was used. The results showed that at 12 hpi, TAP1 was not detectable in wt-infected cells, but TAP1 was detectable in the ER of $U_L49.5$ CT-null-, $U_L49.5\Delta30$-32 CT-null-, $U_L49.5\Delta37$-40 CT-null- and $U_L49.5\Delta43$-46 CT-null-infected cells (data not shown). However, at 6 hpi minor amounts of TAP1 which colocalized with $U_L49.5$ were detectable in the ER of BHV-1 wt-infected MDBK cells (data not shown).

Considering the TAP1 degradation, peptide transport, MHC-I down-regulation, and $U_L49.5$-TAP1 co-localization data, TAP1 and $U_L49.5$ residues 30-32 interaction in the ER is sufficient to inhibit TAP-mediated peptide transport function. However, both $U_L49.5$ residues 30-32 and the $U_L49.5$ CT residues are required for maximum $U_L49.5$ inhibition of TAP function.

As shown in Examples 1-6, we have constructed several $U_L49.5$ luminal domain mutants in which either residues 30-32 (RRE) or 37-40 (FWSA; SEQ ID NO:17) or 43-46 (YARG; SEQ ID NO:18) were deleted in the background of a $U_L49.5$ CT-null virus. We then analyzed their TAP inhibition/MHC-I down-regulation properties in comparison to wt $U_L49.5$ and $U_L49.5$ CT-null. The results indicated that, while increases in TAP-mediated peptide transport and MHC-I cell-surface expression in BHV-1 $U_L49.5$ CT-null infected MDBK cells were significant when compared with BHV-1 wt, an additional deletion of BHV-1 $U_L49.5$ residues 30-32 (RRE) resulted in even further significant increases in peptide transport and MHC-I cell surface expression when compared with BHV-1 wt and BHV-1 $U_L49.5$ CT-null. Subsequently, the $U_L49.5\Delta30$-32 deletion or $U_L49.5$ 30AAA32 substitutions were introduced into BHV-1 wt and their TAP inhibition/MHC-I down-regulation and TAP degradation functions determined in comparison to wt $U_L49.5$ and $U_L49.5$ CT-null. Based on the results, deletion or alanine exchange of $U_L49.5$ residues 30-32 or $U_L49.5$ lacking the CT residues alone prevented $U_L49.5$-mediated bovine TAP1 degradation. Relative to wt $U_L49.5$ or $U_L49.5$ CT-null, a significant increase in peptide transport and MHC-I cell surface expression was seen in $U_L49.5$ 30-32 alanine substitution or deletion mutations in the wt background. Nevertheless, peptide transport and MHC-I surface expression was increased even more when $U_L49.5\Delta30$-32 and $U_L49.5$ 30AAA32 mutations were introduced in the $U_L49.5$ CT-null background. When MDBK cells expressing the wt $U_L49.5$ were infected with the BHV-1 $U_L49.5$ CT-null-, BHV-1 $U_L9.5\Delta30$-32, and BHV-1 $U_L49.5$ 30AAA32 mutant viruses, the inhibition of peptide transport and down-regulation of MHC-I cell surface expression of the mutant viruses were restored to the BHV-1 wt levels. Taken together, the results of TAP1 degradation, peptide transport inhibitory and MHC-I down regulatory property of the BHV-1 $U_L49.5$ CT-null, BHV-1 $U_L49.5\Delta30$-32, BHV-1 $U_L49.5$ 30AAA32 mutants in MDBK cells and MDBK cells expressing wt $U_L49.5$, we conclude that: (1) $U_L49.5$ residues 30-32 (RRE) and $U_L49.5$ CT residues (80-96) both are important for TAP1 degradation; and (2) even though primary TAP inhibition domain lies in $U_L49.5$ 30-32 residues, the fullest extent of $U_L49.5$-mediated TAP inhibition function additionally required the $U_L49.5$ cytoplasmic tail (CT) residues. Similarly, the fullest extent of $U_L49.5$-mediated down-regulation of MHC-I cell surface expression required both the $U_L49.5$ luminal domain residues 30-32 and the $U_L49.5$ CT residues. In summary, the $U_L49.5$ residues 30-32 and $U_L49.5$ CT residues together inhibit peptide transport and down regulate MHC-I cell surface expression.

Since the mutant $U_L49.5\Delta30$-32 CT-null interaction with the gM and gM maturation was unaffected, and the mutant $U_L49.5$ was incorporated in the virion envelope, without wishing to be bound by this theory, we believe that mutant $U_L49.5$ protein conformation was not affected. Results from the calf experiment in the examples below indicated that immunogenicity of and cellular immunity against BHV-1 $U_L49.5\Delta30$-32 CT-null mutant virus were enhanced when compared with wt BHV-1. Therefore, by incorporating these $U_L49.5$ mutations in a future BHV-1 marker vaccine, we will improve the vaccine efficacy of the current BHV-1 gE-deleted marker vaccine.

Example 7

BHV-1 $U_L49.5\Delta30$-32 CT-Null Mutant and Immune Responses in Calves: Materials and Methods Cells and Virus Strain.

The MDBK cell line was maintained in Dulbecco's modified Eagle's medium (DMEM) supplemented with 5-10% heat-inactivated fetal bovine serum (FBS). The BHV-1 Cooper (Colorado-1) strain, obtained from the American Type Culture Collection (Cat # CRL-1390) and BHV-1 $U_149.5\Delta30$-32 CT-null virus constructed using the parental BHV-1 Cooper strain were propagated and titrated in MDBK cells as described above in Examples 1 and 2.

Antibodies.

Rat anti-bovine IFN-γ-specific MAb (R&D, Cat No. MAB23001), biotinylated goat anti-bovine IFN-γ antibody (R&D), mouse anti-bovine CD8 antibody (VMRD, Inc., Pullman, Wash.; Cat No. CACT80C), APC-conjugated donkey anti-mouse IgG (eBioscience, San Diego, Calif.; Cat. No. 17-4012-82), RPE-conjugated mouse anti-bovine CD4 (AbD Serotec, Raleigh, N.C.; Cat No. MCA 1653PE), mouse anti-bovine CD3 antibody (VMRD, Cat No. MM1A), rat anti-mouse IgG1 microbeads (Miltenyi Biotech, Auburn, Calif., Cat No. 130-047-102) were purchased from the respective commercial sources.

Calf Infection and Challenge.

Calf experiments were performed as published earlier [43]. Briefly, eight BHV-1 and bovine viral diarrhea virus (BVDV) negative, 4-month-old cross-bred calves were selected for the experimental trial. The calves were housed at Louisiana State University (LSU) Agricultural Center large animal isolation facility during the entire experimental period. Animal infection, handling, sample collection and euthanasia protocols were approved by the LSU Institutional Animal Care and Use Committee.

Upon arrival, the calves were randomly allocated into two infected groups containing 3 calves each and one control uninfected group containing two calves. Each group was housed in a biocontainment room for a week prior to experimental infection. Two control calves were inoculated with PBS as sham-infected control. Three calves in a mutant group were inoculated with $1 \times 10^7$ PFU of BHV-1 $U_L49.5\Delta30$-32 CT-null mutant virus per nostril and conjunctival sac (total $4 \times 10^7$ PFU). Three calves in a wild-type (wt) BHV-1 group were similarly infected with wt BHV-1 Cooper. On 28 days past infection (dpi), all calves including the uninfected controls were challenged by inoculation of 2×10⁷ PFU/nostril (total 4×10⁷ PFU) of wt BHV-1. Nasal and eye swabs were collected at days 0, 2, 3, 5, 7, 9, 12, 14, 21 and 28 dpi and at days 2, 3, 5, 7, 9 and 12 days post-challenge (dpc) in 1 ml of tissue culture medium supplemented with 2% penicillin and streptomycin. The samples were processed and stored at −80° C. Blood was collected at days 0, 7, 14, 21, 28 dpi and days 7 and 12 dpc for sera and isolation of peripheral blood mononuclear cells (PBMC).

Clinical Evaluations.

Intensive clinical observation of all calves was performed daily for 12 days following primary virus and challenge virus exposures. Rectal temperatures were recorded every other day. Special attention was given to behavior, appetite, cough, ocular and nasal discharges, hyperemia or lesions of the nasal mucosa, conjunctivitis, and abnormal breathing. In the case of nasal discharge, the parameters were scored as follows: 0 when normal, 1 when moderately serous, 2 when severely serous or when mildly mucopurulent, 3 when moderately mucopurulent, and 4 when severely mucopurulent. In the case of depression, as indicated by behavior (e.g., head down, standing in one corner, not eating, and not drinking), the score was 0 when not present, 1 when mild, 2 when moderate, and 3 when severe. When present, hyperemia and ulcers of nasal mucosa were scored as 1 and 2, respectively. Conjunctivitis, coughing, and dyspnea, when present, were each scored as 2. The daily rectal temperature was scored as 1 when it ranged from 39.7° C.-39.99° C., 2 when it ranged from 40.0° C.-40.5° C., 3 when it ranged from 40.6° C.-41° C., and 4 when it was above 41.0° C. [33]. The daily clinical score for each calf was the sum of scores for each parameter. The mean daily clinical score was calculated for each group and compared among groups.

Virus Isolation, Plaque Assay and Virus Neutralization Assay.

Virus titrations were performed as published earlier [33]. BHV-1 specific virus neutralization (VN) titers were determined as published earlier [25]. The titers were expressed as the reciprocal of the highest dilution that caused a 50% reduction in the number of plaques relative to the virus control.

Isolation and Freezing of PBMC.

Blood was collected in tubes containing sodium citrate for an anticoagulant and transported on ice. Peripheral blood mononuclear cells (PBMCs) were isolated using Ficoll-Paque (Ficoll-Paque™ PLUS, GE Healthcare Life Sciences, Piscataway, N.J.) density-gradient centrifugation as previously published [44]. The PBMCs were resuspended in RPMI-1640 complete medium with 10% FBS. Cell viability was determined by trypan blue exclusion. After determining the cell count, PBMCs were resuspended in 10% FBS-RPMI-1640 medium containing 10% DMSO at a concentration of 5×10⁶ cells/ml and frozen at −20° C., transferred into −80° C., and stored in liquid nitrogen until use.

Gamma Interferon (IFN-γ) Enzyme-Linked Immunospot Assay (ELISPOT) Assay.

ELISPOT was performed to detect IFN-γ+ T cells as published earlier [45], with minor modification. Briefly, an ELISPOT plate (Millipore, Billerica, Mass.) was coated overnight at 4° C. with 100 μl/well (10 μg/ml) of purified rat anti-bovine IFN-γ-specific MAb (R&D Systems, Minneapolis, Minn.; Cat. #MAB 23001). After washing with 0.25% Tween 20-PBS, the plates were blocked with 5% FBS-PBS at 37° C. for 2 h. Then 2×10⁵ PBMCs mixed with 20 μg/ml of the UV-inactivated BHV-1 $U_L49.5\Delta30$-32 CT-null purified virion antigen (Ag) were added into each well. For each PBMC sample, three replicate wells were inoculated. After 24 h, the plates were washed with PBS and incubated with 200 μl of $H_2O$ for cell lysis. The plate was incubated (for 2 h) with 50 μl (2 vg/ml) of biotinylated goat anti-bovine IFN-γ Ab per well. Subsequently, plates were incubated for 2 h with 100 μl/well of streptavidin-AP (SouthernBiotech, Birmingham, Ala.). Finally, after washing, 100 μl/well of 1-step NBT/BCIP (Pierce Biotechnology, Rockford, Ill.) was added and incubated for 10 min to develop visible spots. The plates were washed with water, air dried, and the spots were counted by using an automated ELISPOT reader system (Cellular Technologies LTD., Shaker Heights, Ohio) with ImmunoSpot software. The mean number of spots from triplicate wells was adjusted to 1×10⁶ PBMC, and the ELISPOT data were expressed as the mean±SD. The BHV-1 Ag-specific IFN-γ responses were calculated by subtracting the number of spots formed in negative control wells (medium only) from the number of spots formed in the sample wells in response to the BHV-1 Ag stimulation.

CD8+ Lymphocyte Proliferation Assay.

2×10⁵ PBMCs/well from each calf were labeled with 2 mM/ml of CFSE (5,6-carboxyfluorescein diacetate succinimidyl ester) using the CellTrace CFSE cell proliferation kit (Invitrogen, Carlsbad, Calif.) as published earlier [46]. The CFSE-labeled cells were stimulated with 10 μg/ml of the UV-inactivated BHV-1 $U_L49.5\Delta30$-32 CT-null virion antigen for 96 h in a $CO_2$ incubator. Non-stimulated cells served as negative control. At the end of each assay, the cells were harvested by centrifugation and incubated with mouse anti-bovine CD8 antibody for 20 min, subsequently stained with APC-conjugated donkey anti-mouse IgG and analyzed by flow cytometer.

CD8+ T Cell-Mediated Cytotoxic Assay.

For collection of target cells, 5×10⁶ of PBMC isolated from each calf at 0 dpi were incubated with 20 μl of mouse anti-bovine CD3 antibody for 20 min. After washing with PBS, the cells were incubated with 20 μl of rat anti-mouse IgG1 microbeads for 10 min, passed over a magnetized MS column (Miltenyi Biotech, Auburn, Calif.), and washed three times in the column with PBS buffer. The unbound cells (wash-outs) were collected and counted for the total CD3-negative cell number as described [46]. The CD3-negative PBMCs were pulsed with the BHV-1 virion Ag (10 μg/ml) for overnight incubation, and then the sensitized target cells were labeled with 10 μl of 3,3'-dioctadecyloxacarbocyanine (DiOC, Invitrogen) stock solution according the manufacture's protocol and resuspended in 10% FBS-RPMI-1640 medium at a concentration of 1×10⁶ cells/ml.

For CD8+ T cell isolation, PBMC suspensions from an individual calf at different time-points were incubated with anti-bovine CD8 antibody, washed in PBS twice, and then incubated with rat anti-mouse IgG1 microbeads. The cell suspensions were then passed over a magnetized MS column and washed in the column three times with PBS. The cells bound to the column were eluted by forcing 2 ml PBS through the column with a plunger [46]. The total number of column-enriched CD8+ T cells were counted and used as effector cells to mix with the DiOC labeled target cells with E:T ratio 20:1. The target/effector cell mixture was stained with propidium iodide (PI) solution and incubated 37° C. for 4 h and analyzed by FACS [35].

Statistical Analysis.

Analysis of variance was used to analyze statistical significance of the differences between the respective average data obtained for the three treatment groups; a P value of <0.05 was used as the criterion for statistical significance.

Example 8

BHV-1 $U_L$49.5Δ30-32 CT-Null Mutant and Pathogenicity in Calves

Virus Replication.

Figure 11A:
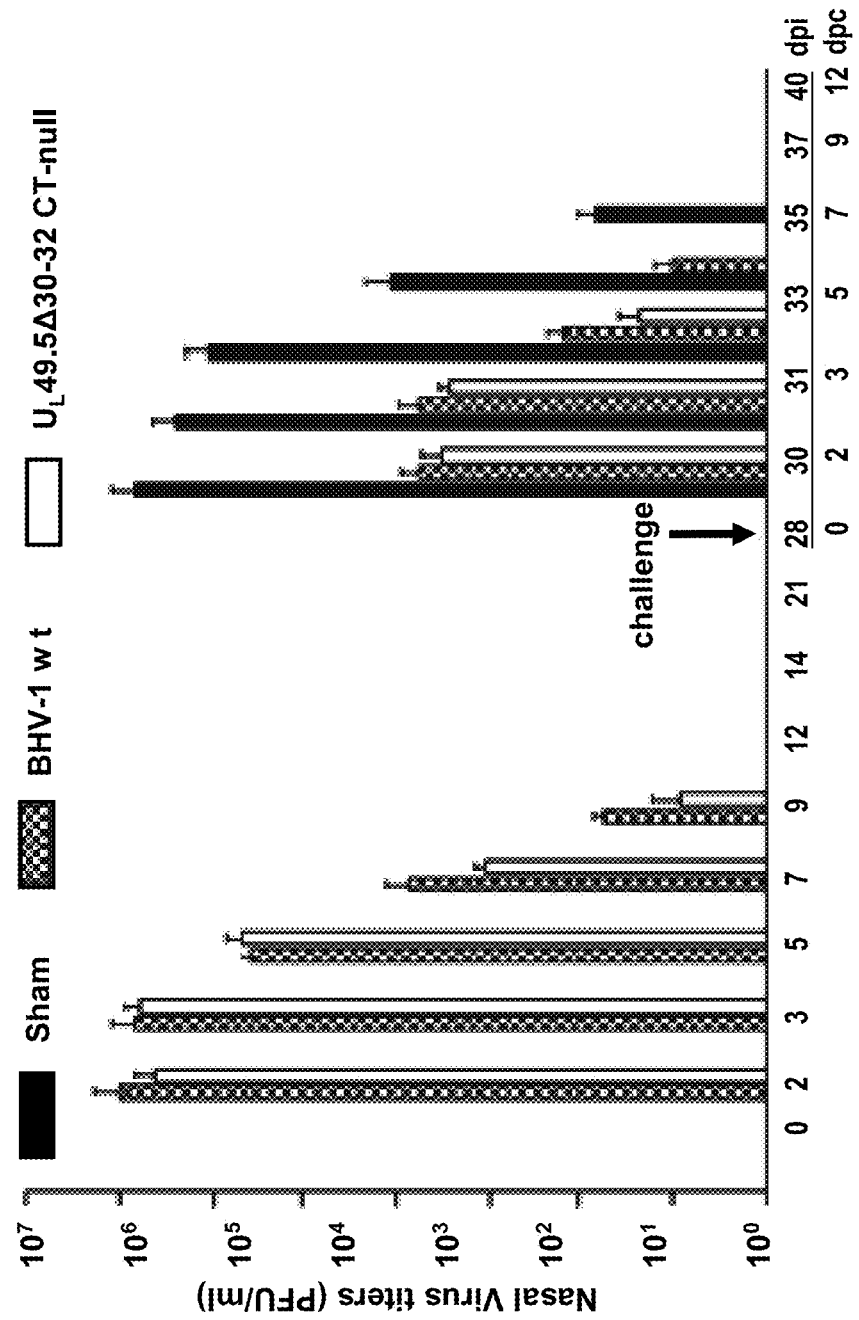
FIG. 11A illustrates the results of an analysis of nasal virus shedding in calves either sham-infected, infected with BHV-1 wt, or infected with BHV-1 $U_L$49.5Δ30-32 CT-null viruses at the indicated intervals (either days post infection (dpi) or days post challenge (dpc)) following primary infection/immunization and following BHV-1 wt nasal challenge.
Figure 11B:
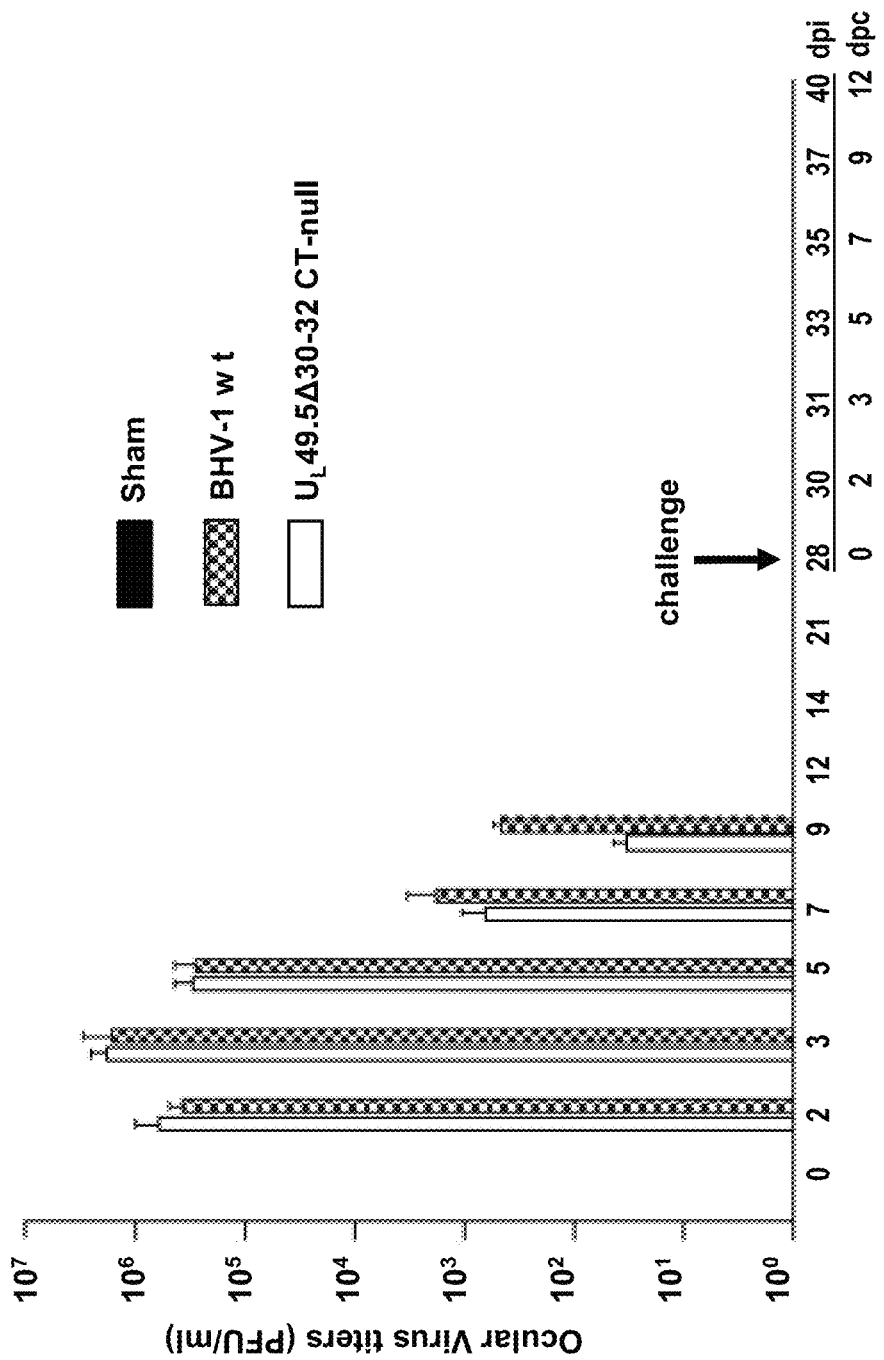
FIG. 11B illustrates the results of an analysis of ocular virus shedding in calves either sham-infected, infected with BHV-1 wt, or infected with BHV-1 $U_L$49.5Δ30-32 CT-null viruses at the indicated intervals (either days post infection (dpi) or days post challenge (dpc)) following primary infection/immunization and following BHV-1 wt nasal challenge.

FIGS. 11A and 11B illustrate the results of an analysis of nasal and ocular virus shedding in calves either sham-infected or infected with BHV-1 wt or BHV-1 $U_L$49.5Δ30-32 CT-null viruses from samples taken at the indicated intervals following primary infection/immunization and following a BHV-1 wt nasal challenge. As shown in FIGS. 11A and 11B, virus was detected in nasal and ocular swabs during days 2-9 dpi in calves infected with both viruses. No significant difference was found in the amounts of virus shed from the nose and eye of calves infected with the either virus. As expected, no virus was detected in nasal and ocular swabs in the sham-infected animals.

Clinical Signs.

Figure 12A:
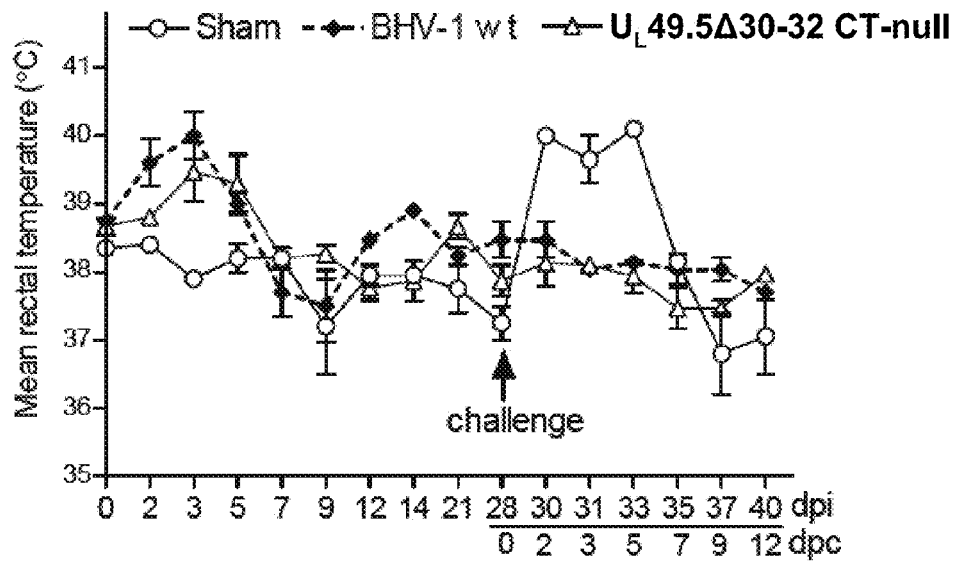
FIG. 12A illustrates the mean rectal temperature for BHV-1 wt-(♦), BHV-1 $U_L$49.5Δ30-32 CT-null mutant-(Δ) or sham-infected (o) calves. The data is presented as mean of two calves (mock) or three calves (virus-infected groups) and standard deviations between the animals at each time point.

Calves infected with either wt BHV-1 or BHV-1 $U_L$49.5Δ30-32 CT-null virus had typical signs of BHV-1 virus infection, including fever, depression, reduced appetite, ocular and nasal discharge, hyperemia and reddening of nasal mucosa, mild ulceration of the nasal mucosa, and coughing. FIG. 12A illustrates the mean rectal temperature for BHV-1 wt-(♦), BHV-1 $U_L$49.5Δ30-32 CT-null mutant-(Δ) or sham-infected (o) calves. The data is presented as the mean of two calves (mock) or three calves (virus-infected groups) and standard deviations between the animals at each time point. As shown in FIG. 12A, the highest rectal temperatures (39.7 to 40.0° C.) were recorded for two days (2-3 dpi) in the BHV-1 wt-infected calves. A similarly high rectal temperature was also recorded in the BHV-1 $U_L$49.5Δ30-32 CT-null mutant virus-infected calves beginning one day later (3 dpi). In both the BHV-1 wt and BHV-1 $U_L$49.5Δ30-32 CT-null mutant infected groups, a mild fever (greater than about 39° C.) lasted until 5 dpi.

Figure 12B:
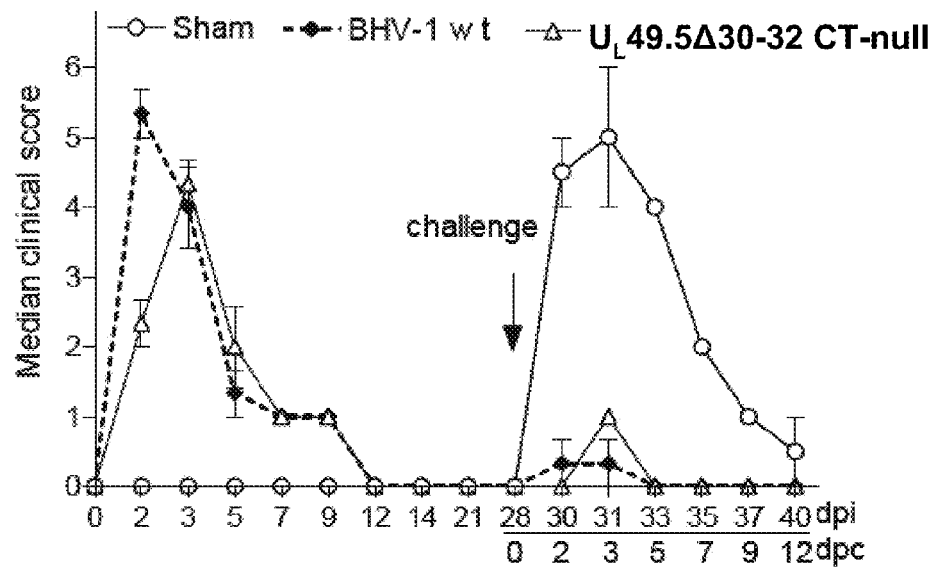
FIG. 12B illustrates the median clinical score for BHV-1 wt-(♦), BHV-1 $U_L$49.5Δ30-32 CT-null mutant-(Δ) or sham-infected (o) calves. The data is presented as mean of two calves (mock) or three calves (virus-infected groups) and standard deviations between the animals at each time point.

FIG. 12B illustrates the median clinical score for BHV-1 wt-(♦), BHV-1 $U_L$49.5Δ30-32 CT-null mutant-(Δ) or sham-infected (o) calves. The data is presented as a mean of two calves (mock) or three calves (virus-infected groups) and standard deviations between the animals at each time points. As shown in FIG. 12B, the high daily clinical scores (~4-5) were obtained for the BHV-1 wt-infected calves for two days (2-3 dpi) while the highest clinical score (4) for the BHV-1 $U_L$49.5Δ30-32 CT-null mutant virus-infected calves was recorded for only one day, a day later at 3 dpi. Therefore, BHV-1 $U_L$49.5Δ30-32 CT-null virus retained a significant pathogenic property, but as compared with BHV-1 wt, the pathogenesis was slightly attenuated in calves.

Example 9

Humoral and Cellular Immune Responses Following BHV-1 $U_L$49.5Δ30-32 CT-Null Mutant Virus Infection in Calves Virus Neutralizing Antibody Response.

Figure 13A:
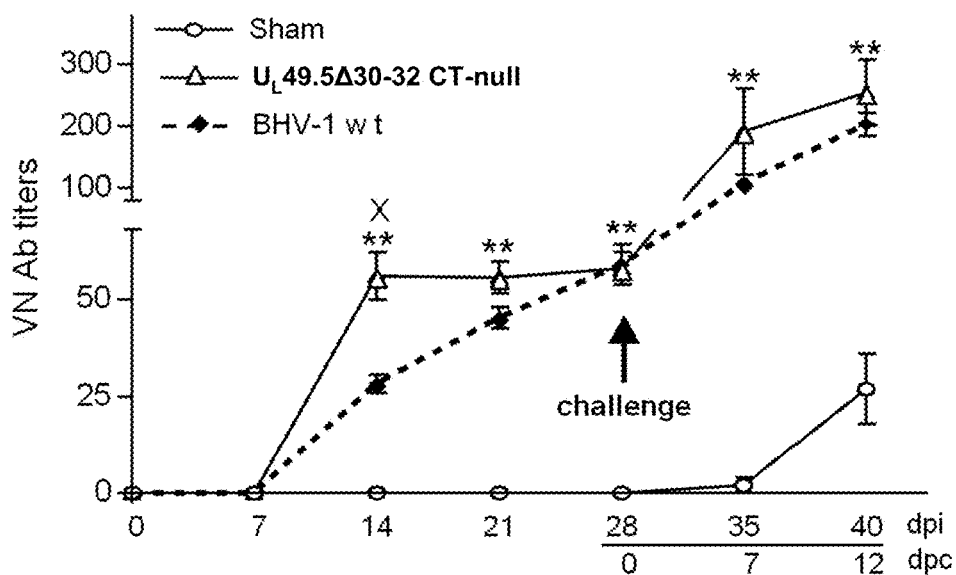
FIG. 13A illustrates an analysis of BHV-1 virus-specific neutralizing antibody (VN) response in the mock-infected and both virus-infected calves following primary infection (immunization) and after BHV-1 wt intranasal challenge. The VN antibody titers were determined in sera collected at the indicated intervals; the titers were expressed as the reciprocal of the highest dilution that caused a 50% reduction in the number of plaques relative to the virus control (100 PFUs). * and ** denote P value <0.05 and <0.01, respectively for the average VN titers in the BHV-1 $U_L$49.5Δ30-32 CT-null mutant group when compared with the sham-infected group. x and xx denote P<0.05 and <0.01, respectively, when results from the $U_L$49.5 mutant group were compared to those for the BHV-1 wt infected group.

FIG. 13A illustrates an analysis of BHV-1 virus-specific neutralizing antibody (VN Ab) response in the mock-infected and both BHV-1 wt and BHV-1 $U_L$49.5Δ30-32 CT-null groups of virus-infected calves following primary infection (immunization) and after BHV-1 wt intranasal challenge. The VN antibody titers were determined in sera collected at the indicated intervals; and the titers were expressed as the reciprocal of the highest dilution that caused a 50% reduction in the number of plaques relative to the virus control (100 PFUs). The symbols "*" and "**" denote P values of <0.05 and <0.01, respectively, for the average VN titers in the $U_L$49.5 mutant group when compared with the sham-infected group; and the symbols "x" and "xx" denote P values of <0.05 and <0.01, respectively, when results from the BHV-1 $U_L$49.5Δ30-32 CT-null mutant group were compared to those for the BHV-1 wt infected group.

As shown in FIG. 13A, both BHV-1 wt and BHV-1 $U_L$49.5Δ30-32 CT-null virus-infected calves generated similar virus neutralizing (VN) antibody titers following primary infection, but the VN antibody response was quicker in the BHV-1 $U_L$49.5Δ30-32 CT-null mutant virus-infected calves. While BHV-1 $U_L$49.5Δ30-32 CT-null mutant virus-infected calves generated an average VN titer of 55 at 14 dpi, it took an additional two weeks (at 28 dpi) for BHV-1 wt virus-infected calves to generate a comparable average VN titer of 58. At 14 dpi, the BHV-1 wt virus-infected calves had an average VN titer of only 27 (two fold less compared with the $U_L$49.5 mutant-infected calves). The BHV-1 $U_L$49.5 mutant infected calves maintained a high VN titers 55-57 during the time period from about 14 dpi to about 28 dpi (FIG. 13A). As expected, sham infected calves were negative for VN titers during this period (FIG. 13A).

Cellular Immune Responses.

The cellular immune responses in calves infected either with BHV-1 $U_L$49.5Δ30-32 CT-null mutant or BHV-1 wt virus were evaluated based on lymphocyte proliferation and number of IFN-γ secreting cells in PBMCs collected following virus infection. Additionally, CD8$^+$T cells from the infected calves were tested for their specific cytotoxic or lysing property of viral antigen-specific target cells. For each assay, PBMCs and CD8+T cells isolated from the calves in the infected group prior to infection (at day 0) as well as from sham-infected calves isolated on the corresponding days post infection served as negative controls.

Figure 13B:
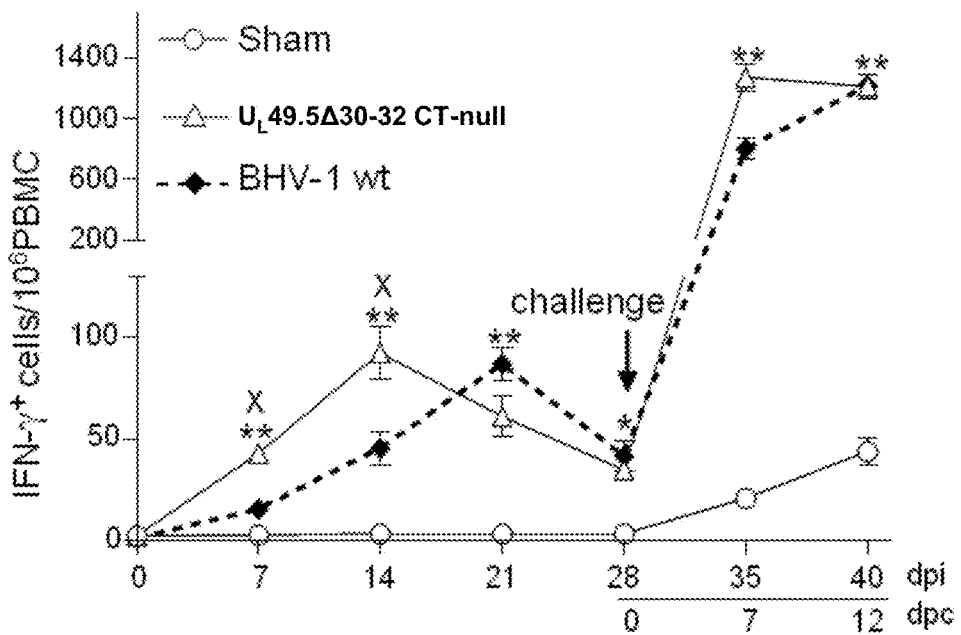
FIG. 13B illustrates an analysis of BHV-1 IFN-γ-producing T cell response in the mock-infected and both virus-infected calves following primary infection (immunization) and after BHV-1 wt intranasal challenge. The measurement of numbers of IFN-γ-producing T cells in the BHV-1 Ag-stimulated PBMCs were determined by ELISPOT. * and ** denote P value <0.05 and <0.01, respectively for the mean number of IFN-γ secreting cells in the BHV-1 $U_L$49.5Δ30-32 CT-null mutant group when compared with the sham-infected group. x and xx denote P<0.05 and <0.01, respectively, when results from the $U_L$49.5 mutant group were compared to those for the BHV-1 wt infected group.

FIG. 13B illustrates an analysis of BHV-1 IFN-γ-producing T cell response in the mock-infected and both groups of virus-infected calves following primary infection (immunization) and after BHV-1 wt intranasal challenge. The measurement of numbers of IFN-γ-producing T cells in the BHV-1 Ag-stimulated PBMCs were determined by ELISPOT. In FIG. 13B, the symbols "*" and "**" denote P values of <0.05 and <0.01, respectively, for the mean number of IFN-γ secreting cells in the $U_L$49.5 mutant group when compared with the sham-infected group; and the symbols "x" and "xx" denote P values of <0.05 and <0.01, respectively, when results from the BHV-1 $U_L$49.5Δ30-32 CT-null mutant group were compared to those for the BHV-1 wt infected group. At 7 and 14 dpi, compared with BHV-1 wt-infected calves, BHV-1 $U_L$49.5Δ30-32 CT-null mutant virus-infected calves developed two fold more IFN-γ secreting T cells (P<0.05; FIG. 13B). Notably, levels of IFN-γ secreting T cells above the controls were reached a week earlier (day 7) in BHV-1 $U_L$49.5Δ30-32 CT-null-infected calves than the BHV-1 wt-infected calves (day 14) (FIG. 13B).

Figure 14A:
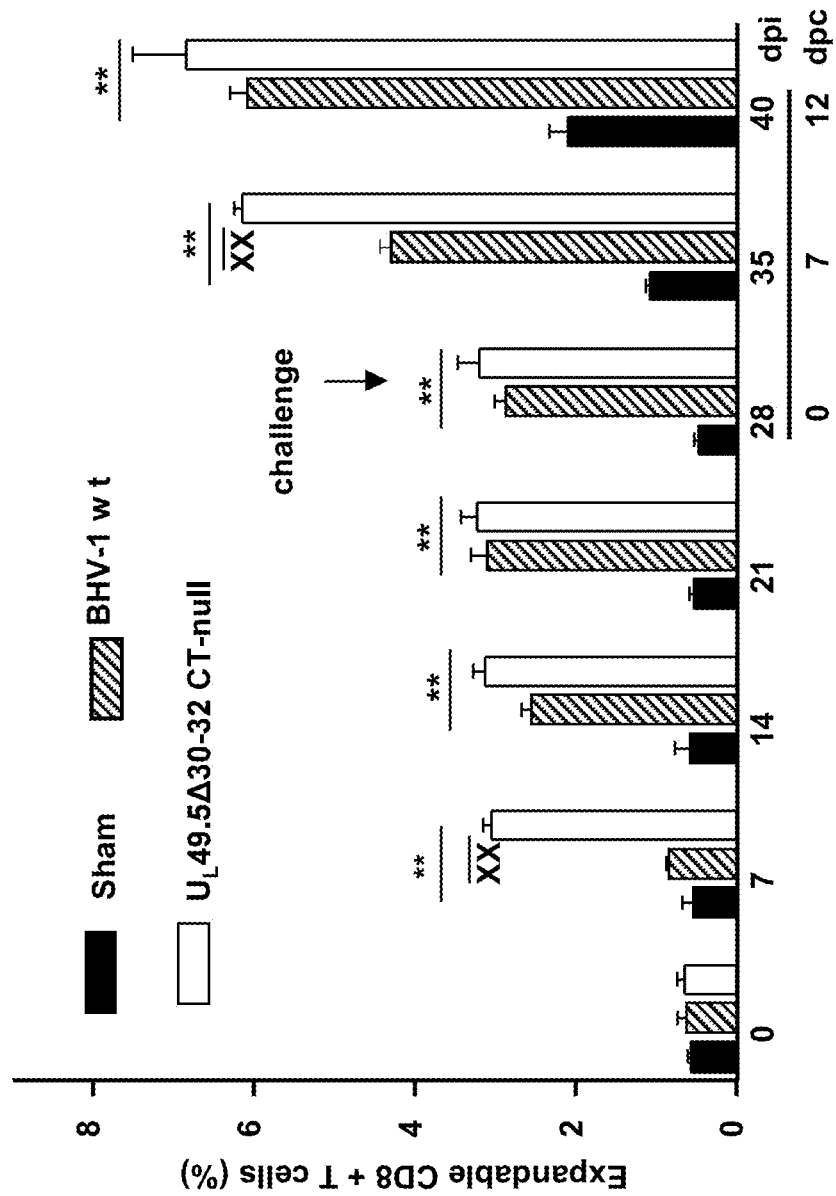
FIG. 14A illustrates the results of FACS analysis of CD8+ T cell proliferation in the mock-infected, BHV-1 wt- and BHV-1 $U_L$49.5Δ30-32 CT-null mutant virus-infected calves following infection (immunization) and after BHV-1 wt challenge. * and ** denote P value <0.05 and <0.01, respectively for the percentages of individual parameters in the $U_L$49.5 mutant group when compared with the sham-infected group. x and xx denote P<0.05 and <0.01, respectively, when results from the $U_L$49.5 mutant group were compared to those for the BHV-1 wt infected group.

FIG. 14A illustrates the results of FACS analysis of CD8+ T cell proliferation in the mock-infected, BHV-1 wt- and BHV-1 $U_L$49.5Δ30-32 CT-null mutant virus-infected calves following infection (immunization) and after BHV-1 wt challenge. In FIG. 14A, the symbols "*" and "**" denote P values of <0.05 and <0.01, respectively, for the percentages of individual parameters in the $U_L$49.5 mutant group when compared with the sham-infected group; and the symbols "x" and "xx" denote P values of <0.05 and <0.01, respectively, when results from the $U_L$49.5 mutant group were compared to those for the BHV-1 wt infected group. The data presented in FIG. 14A show that PBMCs from BHV-1 $U_L$49.5Δ30-32 CT-null mutant virus infected calves had a significantly higher CD8+ lymphocyte proliferation (P<0.01) at 7 dpi compared with that of BHV-1 wt virus-infected calves (>3 fold higher) and of sham-infected calves (>5 fold higher). At 14, 21 and 28 dpi, PBMCs from both BHV-1 wt and BHV-1 $U_L49.5\Delta30$-32 CT-null mutant infected calves developed significantly higher CD8+ T cell responses compared with the sham-infected calves. However, there was no significant difference of CD8 T cell expansion in PBMC between the BHV-1 $U_L49.5\Delta30$-32 CT-null mutant- and BHV-1 wt infected groups (FIG. 14A).

Figure 14B:
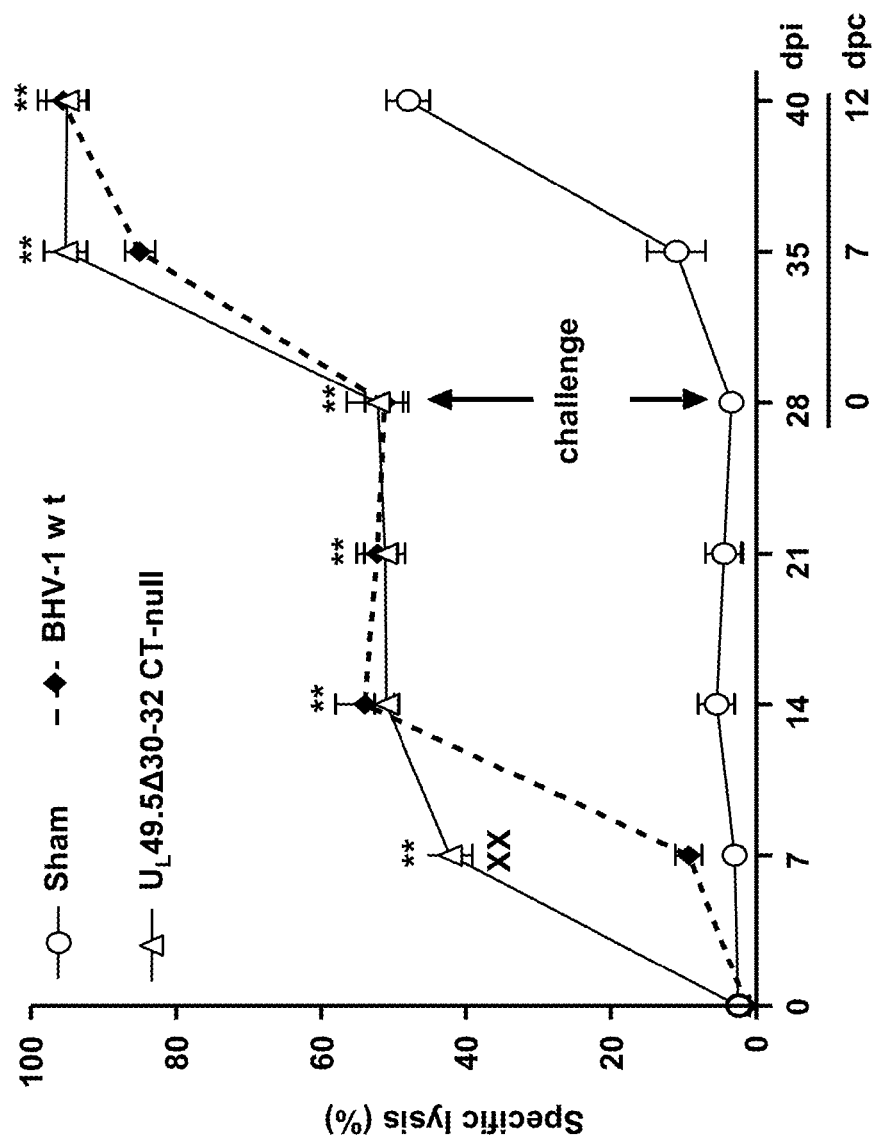
FIG. 14B illustrates the results of an analysis of cytotoxicity of CD8+ T cells in the mock-infected, BHV-1 wt- and BHV-1 $U_L$49.5Δ30-32 CT-null mutant virus-infected calves following infection (immunization) and after BHV-1 wt challenge. * and ** denote P value <0.05 and <0.01, respectively for the percentages of individual parameters in the $U_L$49.5 mutant group when compared with the sham-infected group. x and xx denote P<0.05 and <0.01, respectively, when results from the $U_L$49.5 mutant group were compared to those for the BHV-1 wt infected group.
Figure 16A:
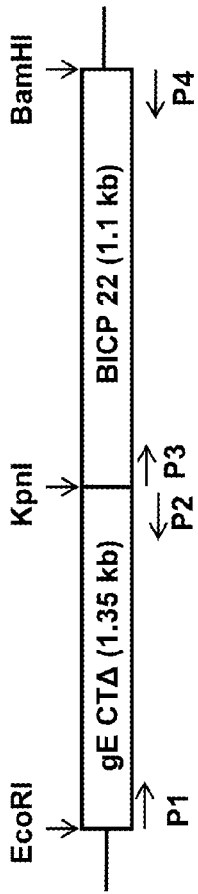
FIG. 16A is a schematic illustration showing the strategy for the pBHV-1 gE CT$\Delta$/Us9$\Delta$ deletion vector construction, showing the location of the primers listed in FIG. 16B and in Table 2.
Figure 17A:
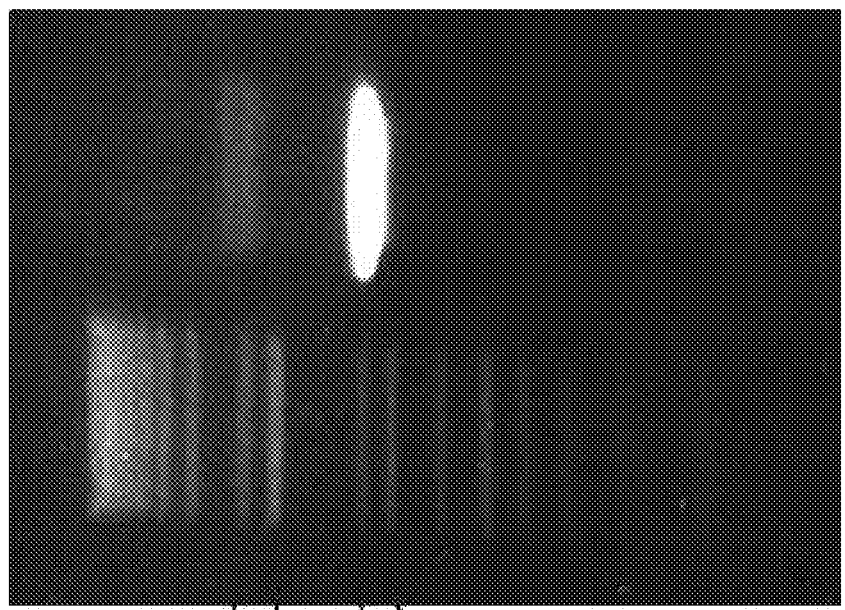
FIG. 17A shows the results of a PCR amplification of partial BHV-1 gE ORF, containing the gE ectodomain and transmembrane domains shown as nucleotides 1-1353 bp in FIG. 18, SEQ ID NO:42.
Figure 17B:
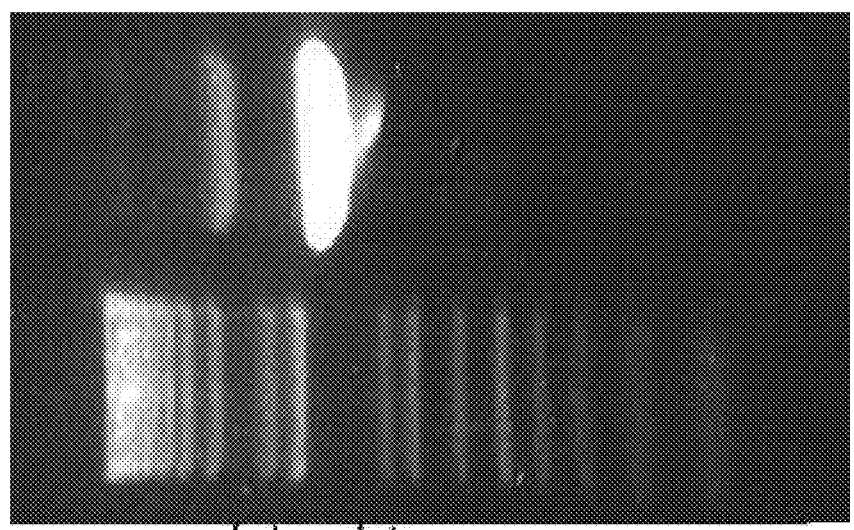
FIG. 17B shows the results of a PCR amplification of BHV-1 Us9 downstream 1.1 kb fragment containing partial bICP22 and Us9/bICP22 intergenic sequence.
Figure 19:
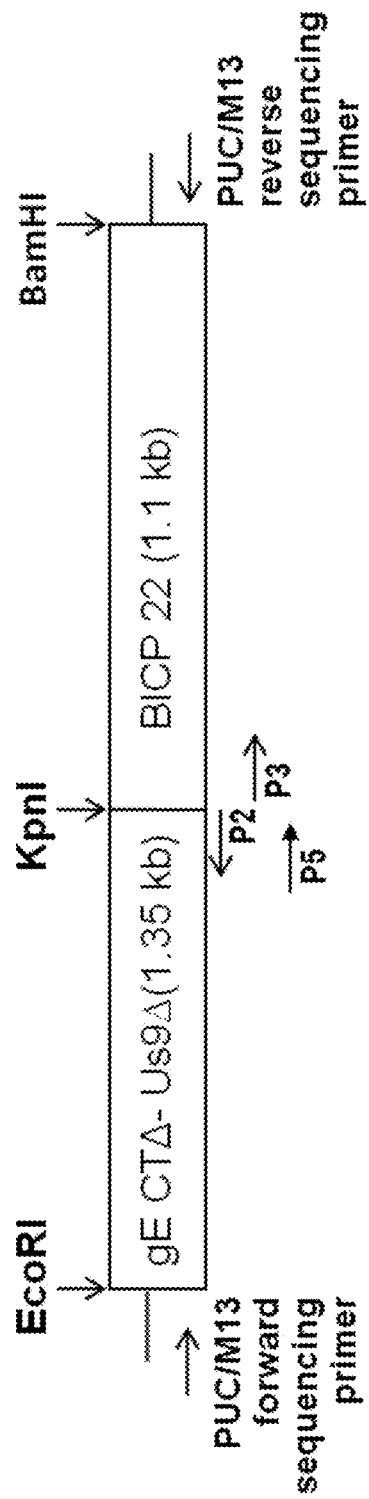
FIG. 19 illustrates the strategy used to design the PCR primers for sequencing and verifying the pBHV-1 gE CT$\Delta$ deletion vector, showing the location of the PUC/M13 forward (SEQ ID NO:23) and reverse (SEQ ID NO:24) primer pair, and the P2 (SEQ ID NO:20), P3 (SEQ ID NO:21) and P5 (SEQ ID NO:26) primers. The sequences for the primers are given in Table 2, except for primer P5 which is given in Table 3.

To compare the relative ability of calves infected either with BHV-1 wt or with BHV-1 $U_L49.5\Delta30$-32 CT-null virus in generating a viral antigen-specific CTL response, CD8+ T cells from sham-infected or respective virus-infected calves (isolated at 0, 7, 14, 21 and 28 dpi) were incubated with auto-sensitized target cells pulsed by the UV-inactivated BHV-1 antigen (Ag). FIG. 14B illustrates the results of an analysis of cytotoxicity of CD8+ T cells in the mock-infected, BHV-1 wt- and BHV-1 $U_L49.5\Delta30$-32 CT-null mutant virus-infected calves following infection (immunization) and after BHV-1 wt challenge. In 14B, the symbols "*" and "**" denote P values of <0.05 and <0.01, respectively, for the percentages of individual parameters in the $U_L49.5$ mutant group when compared with the sham-infected group; and the symbols "x" and "xx" denote P values of <0.05 and <0.01, respectively, when results from the $U_L49.5$ mutant group were compared to those for the BHV-1 wt infected group. As shown in FIG. 14B, 48-50% of the target cells (P<0.01) were lysed when incubated with CD8+ T cells isolated from infected calves for both viruses at 14, 21 and 28 dpi, but not when the cells were incubated with CD8+ T cells from the sham-infected control calves. However, at 7 dpi, the CTL activity of the isolated CD8+ T cells from the BHV-1 wt- and BHV-1 $U_L49.5$ mutant-infected calves was 9% and 45%, (P<0.01), respectively (FIG. 14B). The results of CD8+ T cell proliferation, BHV-1-specific IFN-$\gamma^+$ T-cell response, and CTL activity assays all indicate that BHV-1 $U_L49.5\Delta30$-32 CT-null mutant virus induced significant cellular immune responses as early as 7 dpi. A similar response was delayed in BHV-1 wt-infected calves by about 1 week.

Protection Against Challenge with BHV-1 wt.

To determine protective efficacy of BHV-1 $U_L49.5\Delta30$-32 CT-null mutant-infected/vaccinated calves and to compare recall cellular immune responses in calves infected with BHV-1 wt with those of BHV-1 $U_L49.5\Delta30$-32 CT-null-infected calves, sham-infected and the respective virus-infected calves were challenged intranasally on 28 dpi with $4\times10^7$ PFU of BHV-1 wt virus. After challenge, calves were monitored for clinical signs and rectal temperatures. The sham-infected calves had elevated temperatures (>40° C.) and high clinical scores (4-5) between days 2-7 post challenge (FIGS. 12A and 12B). In contrast, the calves infected previously, either with BHV-1 $U_L49.5\Delta30$-32 CT-null or BHV-1 wt virus, had nearly normal body temperatures (slight or no increase in body temperature) and low clinical scores.

In addition, the amount of virus shedding in the nasal fluids was determined. As shown in FIG. 11A, both BHV-1 wt and BHV-1 $U_L49.5\Delta30$-32 CT-null virus-infected calves shed 3 to 4 logs lower amounts of virus in the nasal swabs between days 2-5 post challenge, as compared with the sham-infected control calves. Nasal virus shedding in the BHV-1 $U_L49.5\Delta30$-32 CT-null virus-infected group lasted for 5 days while it lasted for 7 and 9 days for BHV-1 wt virus-infected and sham-infected calves, respectively.

To determine relative protective immune responses in BHV-1 wt and BHV-1 $U_L49.5\Delta30$-32 CT-null mutant virus-infected calves compared with sham-infected calves against the BHV-1 wt challenge infection, neutralizing antibody and cellular immune responses in calves were compared among the groups. In addition, recall virus neutralizing and cellular immune responses in BHV-1 wt verses BHV-1 $U_L49.5\Delta30$-32 CT-null-infected calves were critically analyzed. The results, as discussed above, show that relative to sham-infected calves, both BHV-1 wt- and BHV-1 $U_L49.5\Delta30$-32 CT-null mutant-infected/immunized calves showed significantly increased virus neutralizing antibody titers (P<0.01), increased CD8+ T cell proliferation (P<0.01, >3-5 fold higher), increased IFN-$\gamma$+ T cell response (P<0.01, >38 to 60 fold higher) and increased CTL activity (P<0.01, >3 fold higher) following a challenge with BHV-1 wt (7-12 days post challenge).

When the recall virus neutralizing antibody responses were compared at 7 days post challenge, calves infected with the BHV-1 $U_L49.5\Delta30$-32 CT-null virus had attained a higher VN titer (200) as compared with BHV-1 wt virus infected calves (115) (FIG. 13A), but the difference was not statistically significant (P>0.05). The magnitude of the recall IFN-$\gamma^+$ T cells and CD8+ T cell proliferation in the BHV-1 $U_L49.5\Delta30$-32 CT-null virus-infected calves was significantly higher than that seen for the BHV-1 wt virus infected calves (P<0.05 and P<0.01, respectively). With respect to CTL function in lysing the BHV-1-pulsed target cells, there was no significant difference between the two virus-infected groups.

Taken together, based on the shorter duration of virus shedding, virus neutralizing and cellular immune responses, both the BHV-1 wt virus- and BHV-1 $U_L49.5\Delta30$-32 CT-null virus-infected calves were protected against challenge with BHV-1 wt. However based on cellular immune responses, protection in the BHV-1 $U_L49.5\Delta30$-32 CT-null mutant virus-infected calves was significantly better than that of BHV-1 wt virus-infected calves.

As shown above, the effect(s) of the BHV-1 $U_L49.5\Delta30$-32 CT-null virus mutation in calves was determined with respect to nasal viral replication and nasal viral shedding properties following intranasal infection. The BHV-1 $U_L49.5\Delta30$-32 CT-null mutant virus was shown to replicate efficiently. For the first 5 days post infection, the amount of BHV-1 $U_L49.5\Delta30$-32 CT-null mutant virus detected in the nasal swabs were similar to that from the wildtype (wt) BHV-1 infected calves. However, at 7 and 9 dpi slightly reduced amounts of BHV-1 $U_L49.5\Delta30$-32 CT-null mutant virus were recovered from the nasal swabs. This indicated that there was no effect of $U_L49.5$ mutation on the initial viral replication and nasal viral shedding. Within 14 days after primary infection, BHV-1 $U_L49.5\Delta30$-32 CT-null mutant virus-infected calves had a VN titer of 55, which was not attained until two weeks later (28 dpi) in the wt virus-infected calves. In addition, PBMCs from calves infected with the BHV-1 $U_L49.5\Delta30$-32 CT-null mutant virus had significantly increased CD8+ cell proliferation and CD8+ T cell mediated cytotoxicity at 7 dpi, and significantly greater numbers of IFN $\gamma^+$ T cells at 7 and 14 dpi. But at 21 dpi, there was no significant difference in cellular immune responses between the BHV-1 wt and BHV-1 $U_L49.5\Delta30$-32 CT-null mutant groups. BHV-1-mediated transient suppression of cellular immune responses occurs during the early phase of infection [2, 34]. Without wishing to be bound by this theory, it is believed that the significant increase in cellular immune response in BHV-1 $U_L49.5\Delta30$-32 CT-null mutant virus infected calves at 7 dpi is due to increased presentation of viral peptide in the context of MHC-I. Since IFN-$\gamma$ alone is known to up-regulate the class II antigen presenting pathway and thus promote peptide-specific activation of CD4+ T cells, the increased IFN-γ production by T cells in calves infected with BHV-1 $U_L$49.5Δ30-32 CT-null virus, both at 7 and 14 dpi, when compared with BHV-1 wt-infected calves, contributed to the higher and early VN antibody response. In summary, the results of nasal virus shedding and immune responses following primary infection in calves clearly demonstrated that BHV-1 $U_L$49.5Δ30-32 CT-null virus induced better primary immune responses than BHV-1 wt and had similar virus replication.

The protective effects of prior infection and immunization with either BHV-1 $U_L$49.5Δ30-32 CT-null mutant or BHV-1 wt on a subsequent infection from a challenge with wt BHV-1 were then compared with respect to nasal virus shedding, clinical scores, VN titers and cellular immune response. Relative to the control uninfected group, both the wt BHV-1 and BHV-1 $U_L$49.5Δ30-32 CT-null mutant infected groups showed significant protection against wt BHV-1 challenge infection. There were significant reductions in nasal virus shedding, clinical scores and rectal temperatures. In addition, both infected groups exhibited rapid recall immune responses such as significant increase in VN titers, IFN-γ$^+$ T cells, CD8$^+$ T cell proliferation and CD8$^+$ T cell-mediated cytotoxicity.

When the values for all the above clinical parameters were compared between the BHV-1 $U_L$49.5Δ30-32 CT-null mutant and BHV-1 wt-infected groups, the duration of nasal virus shedding was two days shorter in the $U_L$49.5 mutant group. Consistent with these results, following wt BHV-1 challenge, the spike in VN titers and the increase in IFN-γ$^+$ T cells and CD8$^+$ T cell proliferation in $U_L$49.5 mutant infected calves were earlier and significantly increased at 7 days post challenge. Since the duration of nasal virus shedding was two days shorter in the $U_L$49.5 mutant infected calves, the earlier virus clearance was probably due to the combined effect of earlier and increased VN antibodies and cellular immune responses. This property is certainly beneficial and desirable in a live, attenuated, genetically engineered vaccine candidate. Since the BHV-1 $U_L$49.5Δ30-32 CT-null mutant virus retained some degree of virulence, incorporation of additional mutations, such as gE cytoplasmic tail and US9 deletions as described below in Examples 10 and 11, was used to attenuate the virus and ensure that the latent vaccine virus will not be shed following reactivation from latency, and to incorporate a serological marker.

Example 10

Generation of BHV-1 gE Cytoplasmic Tail and Us9 Deleted Virus in the Backbone of BHV-1 $U_L$49.5Δ30-32 CT-Null We have made a new mutant virus that can be used as a vaccine by introducing additional gE cytoplasmic tail- (gE CT) and Us9 ORF deletions (gE CTΔ/Us9Δ) in the backbone of the BHV-1 $U_L$49.5 (gN) luminal domain residues 30RRE32Δ and $U_L$49.5 CT-null (cytoplasmic tail truncated) virus (BHV-1 $U_L$49.5Δ30-32 CT-null virus, as described above in Examples 1 and 2, and as shown in FIGS. 15B and 15C). To introduce the gE CTΔ/Us9Δ deletions, first a BHV-1 gE CT-Us9 deletion vector (pBHV-1 gE CTΔ/Us9Δ) was constructed. FIG. 15A is a schematic illustration of the BHV-1 genome showing the locations of the BHV-1 $U_L$49.5, gE, Us9, and bICP22 genes, with the orientations of gE, Us9, and bICP22 gene transcriptions indicated by arrows. FIG. 15B is a schematic illustration of the BHV-1 wt $U_L$49.5 residues, highlighting the luminal domain residues of BHV-1 wt (SEQ ID NO:35) and of BHV-1 $U_L$49.5Δ30-32 CT-null (SEQ ID NO:36). FIG. 15C is a schematic illustration of the BHV-1 $U_L$49.5Δ30-32 CT-null/gE CTΔ/Us9Δ viral genome.

Construction of the Deletion Vector, pBHV-1 gE CTΔ/Us9Δ.

First, using primer pair P1(For) SEQ ID NO:19/P2 (Rev) SEQ ID NO:20 (as shown in Table 2, and FIGS. 16A and 16B) and BHV-1 Cooper strain genomic DNA as a template, a 1.35 kb EcoRI/KpnI fragment spanning the entire gE ectodomain and the transmembrane domain was amplified. FIG. 16A illustrates the strategy for the pBHV-1 gE CTΔ/Us9Δ deletion vector construction, showing the location of the primers listed in FIG. 16B and in Table 2. FIG. 16B shows the sequences of the primers (P1, SEQ ID NO:19; P2, SEQ ID NO:20; P3, SEQ ID NO:21; and P4, SEQ ID NO:22) used to generate pBHV-1 gE CTΔ/Us9Δ. Primers P1 and P2 incorporate the EcoRI and KpnI restriction sites, respectively. The Poly A and Stop sequences designed in P2 are complementary, and the gE nucleotide numbers, 1329-1353, refer to nucleotide sequence spanning the gE, Us9 and part of the bICP22 genes of the BHV-1 genomic sequence (GenBank accession #AJ004801) and as as shown in FIG. 18 (SEQ ID NO:42).

FIG. 17A shows the PCR amplification of partial BHV-1 gE ORF (gE ectodomain and transmembrane domains, from nucleotides (NT) 1-1353 in FIG. 18, SEQ ID NO:42). The P1 forward primer (SEQ ID NO:19) incorporated the EcoRI site (at 5' end) and the P2 reverse primer (SEQ ID NO:20) introduced three stop codons (in all 3 frames) immediately downstream of gE NT 1353 or corresponding amino acid residue 451 (Ala) as noted in FIG. 18. In addition, the P2 primer (SEQ ID NO:20) incorporated a consensus PolyA (AATAAA) and KpnI site (FIG. 16B) at the 3' end of the amplified fragment. The PCR generated fragment was digested with EcoRI and KpnI and cloned into the EcoRI/KpnI sites of pGEM-7Z plasmid (Promega, Madison, Wis.), resulting in plasmid clone pBHV-1 gE CTΔ.

Next, using primer pair P3 (For) (SEQ ID NO:21)/P4 Rev (SEQ ID NO:22) (shown in Table 2 and FIG. 16B), a 1,234-bp Us9 downstream fragment containing bICP22 sequence was amplified. FIG. 17B shows the PCR amplification of the BHV-1 Us9 downstream 1.1 kb fragment containing partial bICP22 and Us9/bICP22 intergenic sequence. The P3 (SEQ ID NO:21)/P4 (SEQ ID NO:22) primer pair introduced KpnI and BamHI sites at the 5' and 3' ends, respectively of the amplified fragment. The KpnI/BamHI digested PCR fragment was then cloned into the KpnI/BamHI sites of pBHV-1 gE CTΔ constructed above, resulting in pBHV-1 gE CTΔ-Us9Δ as schematically illustrated in FIG. 19. FIG. 20 shows the nucleotide sequence of the gE ectodomain-bICP from the plasmid clone pBHV-1 gE CTΔ/Us9Δ DNA. The gE aa451 (alanine) encoded by GCA is marked by an arrow in FIG. 20. In addition, the triple stop codons, poly A sequence, and KpnI sites immediately left (downstream of bICP22 based on the gene orientation shown in FIG. 15A) of the bICP22 are shown. The nucleotide sequences of the insert spanning the gE ectodomain and part of bICP22 in the plasmid clone pBHV-1 gE CTΔ/Us9Δ was determined by sequencing and aligned with wt BHV-1 gE ectodomain sequence (data not shown). The expected changes were verified by the sequencing and alignment. The resulting clone was shown to have the following: (a) NT 1354-2357 (SEQ ID NO:42; FIG. 18), containing the gE CT, the gE-Us9 intergenic region, and the entire Us9 ORF coding sequences were deleted and a 21 bp fragment containing triple stop codon, Poly A sites, and a KpnI site was incorporated as shown in FIG. 16A and FIG. 20 (SEQ ID NO:43); and (b) the remaining gE coding region (NT 1-1353, or corresponding amino acid residues 1-451)

(FIG. 18) was placed immediately adjacent to and left of the bICP22 gene (FIG. 18 and FIG. 20).

Construction and Characterization of BHV-1 $U_L49.5\Delta30$-32 CT-Null/gE CT$\Delta$/Us9$\Delta$ Virus.

Figure 21:
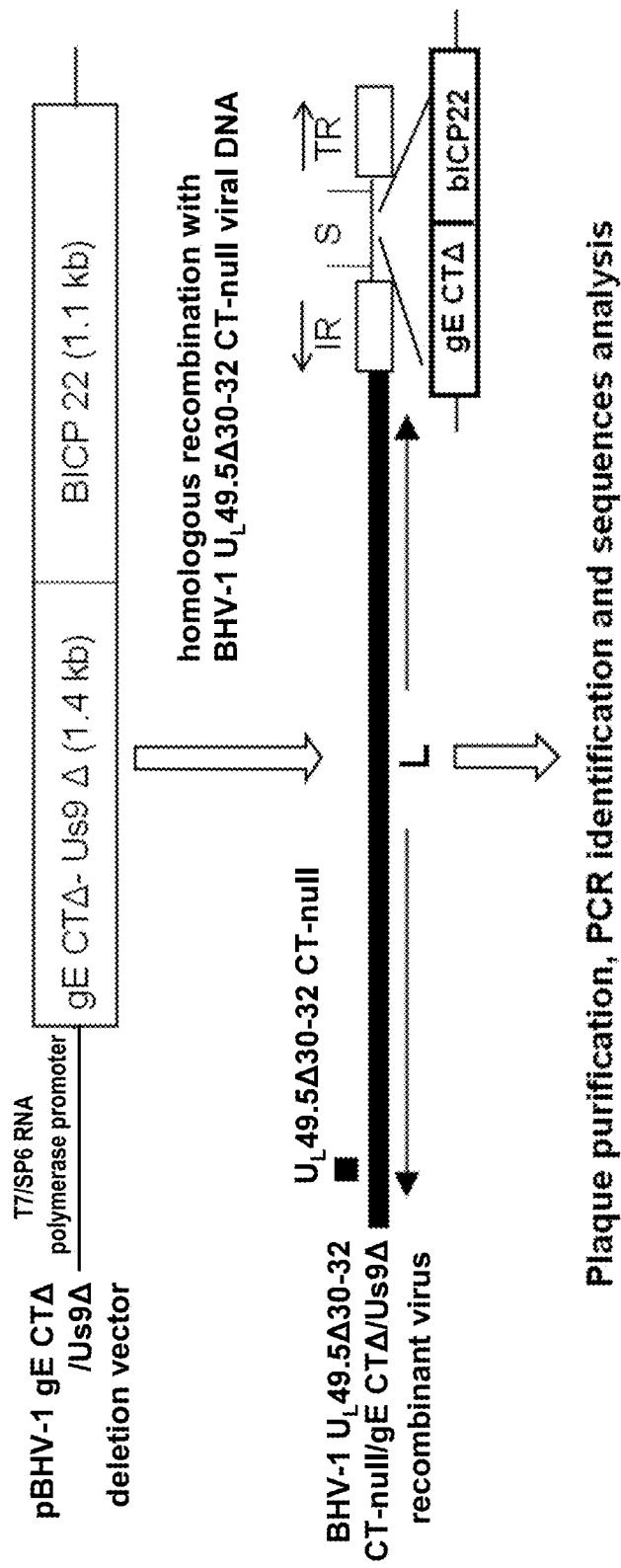
FIG. 21 is a schematic illustration showing the strategy for the BHV-1 $U_L49.5\Delta30$-32 CT-null/gE CT$\Delta$/Us9$\Delta$ recombinant virus plaque purification, PCR identification, and sequence analysis.
Figure 22:
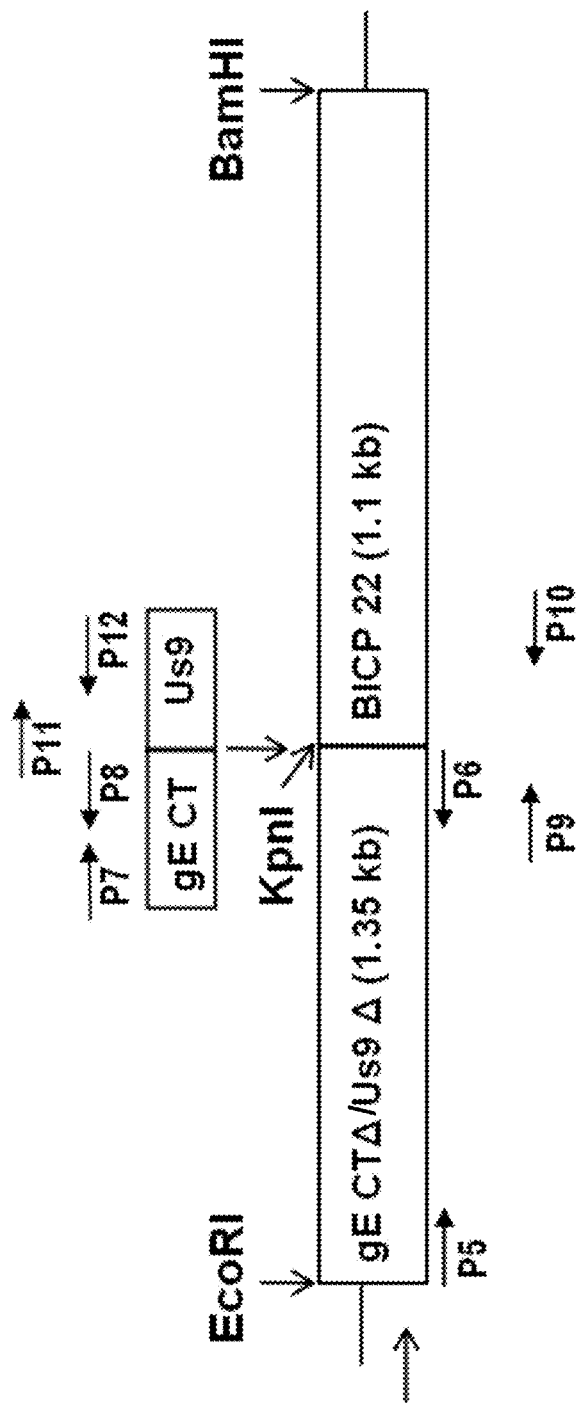
FIG. 22 is a schematic illustration showing the strategy for PCR amplification and/or sequencing for verification of the BHV-1 $U_L49.5\Delta30$-32 CT-null/gE CT$\Delta$/Us9$\Delta$ recombinant virus harboring intended gE CT and Us9 ORF deletions. The locations of the various primers, P5-P12, are shown; and the sequences for these primers are given in Table 3.
Figure 23A:
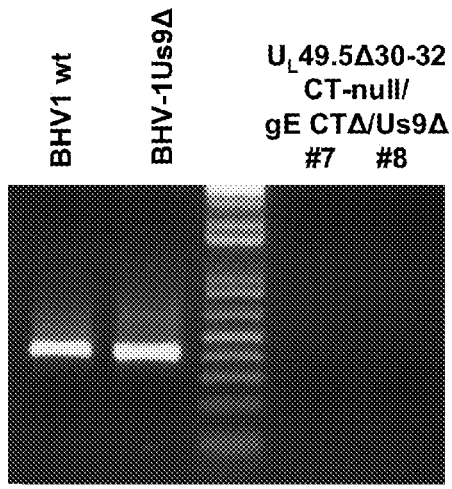
FIG. 23A illustrates the results of PCR identification of the plaque-purified putative BHV-1 $U_L49.5\Delta30$-32 CT-null/gE CT$\Delta$/Us9$\Delta$ mutant virus, and shows the PCR amplification of about 400 bp BHV-1 gE CT fragment using the gE CT-specific primer pair, P7 and P8, shown in Table 3 and FIG. 22.
Figure 23B:
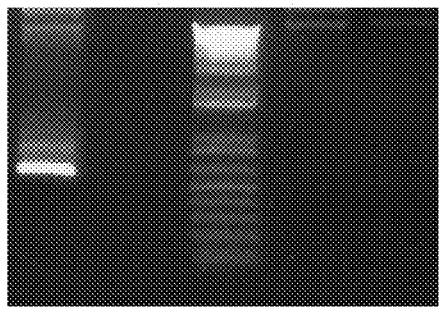
FIG. 23B illustrates the results of PCR identification of the plaque-purified putative BHV-1 $U_L49.5\Delta30$-32 CT-null/gE CT$\Delta$/Us9$\Delta$ mutant virus, and shows the PCR amplification of about 550 bp BHV-1 Us9 fragment using the Us9 ORF-specific primer pair, P11 and P12, shown in Table 3 and FIG. 22.
Figure 23C:
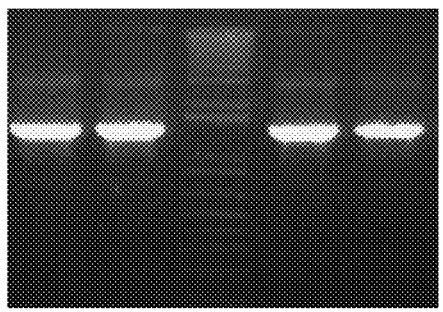
FIG. 23C illustrates the results of PCR identification of the plaque-purified putative BHV-1 $U_L49.5\Delta30$-32 CT-null/gE CT$\Delta$/Us9$\Delta$ mutant virus, and shows the PCR amplification of about 1350 bp BHV-1 gE ectodomain fragment using the gE ectodomain-specific primer pair, P5 and P6, shown in Table 3 and FIG. 22.

To generate a BHV-1 gE CT- and Us9-deleted recombinant virus, EcoRI digested (linearized) pBHV-1 gE CT$\Delta$/Us9$\Delta$ DNA and full-length BHV-1 $U_L49.5\Delta30$-32 CT-null virus genomic DNA (as described above in Examples 1 and 2) were co-transfected in MDBK cells using Lipofectamine (Invitrogen, Carlsbad, Calif.), as schematically shown in FIG. 21. Several recombinant viral plaques showing small plaque phenotype were picked. Two putative recombinant virus plaques (plaques #7 and #8) were plaque purified three times and were analyzed by PCR. FIG. 22 shows the strategy and location of the primers used for PCR amplification and sequencing for verification of the BHV-1 gE CT$\Delta$/Us9$\Delta$ recombinant virus. The sequences of the primers shown in FIG. 22 are given in Table 3. FIG. 23 shows the results of the PCR identification of plaques #7 and #8 as compared to BHV-1 wt and BHV-1 Us9$\Delta$. The PCR verified the presence or absence of the BHV-1 gE CT fragment using primer pairs, P7 (SEQ ID NO:28) and P8 (SEQ ID NO:29) (FIG. 23A), of the BHV-1 Us9 fragment using primer pairs, P11(SEQ ID NO:32) and P12 (SEQ ID NO:33) (FIG. 23B), and of the BHV-1 gE ectodomain fragment using primer pairs, P5 (SEQ ID NO:26) and P6 (SEQ ID NO:27) (FIG. 23C). As depicted in FIG. 23B, the Us9-specific band was deleted in the case of putative recombinant #7 and 8 and in control Us9$\Delta$ virus (BHV-1Us9$\Delta$), but not in wt BHV-1. However, as expected and as depicted in FIG. 23C, gE ectodomain and gE transmembrane sequences containing fragment were present in all the viruses tested.

The nucleotide sequence of the gE-bICP 22-specific PCR fragment amplified from the putative recombinant #7 BHV-1 $U_L49.5\Delta30$-32 CT-null/gE CT$\Delta$/Us9$\Delta$ viral DNA by using primer pair P9/P10 (Table 3; as shown in FIG. 22) was determined (data not shown). As expected, the gE ORF was terminated immediately following the NT 1353 (FIG. 18; SEQ ID NO:42) or codon GCA for gE residue 451 ala. In addition, a Poly A sequence and a KpnI site was found to be incorporated immediately before and adjacent to the bICP22 sequence. Therefore, the entire gE CT and Us9 coding regions (NT 1354-2357 in FIG. 18) of the putative recombinant virus #7 were deleted.

In addition, the nucleotide sequences of the $U_L49.5$ ORF specific PCR fragment (Query) amplified from the putative recombinant #7 BHV-1 $U_L49.5\Delta30$-32 CT-null/gE CT$\Delta$/Us9$\Delta$ viral DNA using primer pair N1 and N2 (Table 3; shown in FIG. 22) was determined and compared with the wt $U_L49.5$ sequence (Gen Bank accession #AJ004801). As expected, the $U_L49.5$ sequence for the putative recombinant virus #7 contained the $U_L49.5$ wt sequences but with residues 30-32 deleted, residues 80-81 deleted, and in addition contained a stop codon immediately following the $U_L49.5$ residue 79, which truncated the entire $U_L49.5$ cytoplasmic tail (data not shown).

Figure 24:
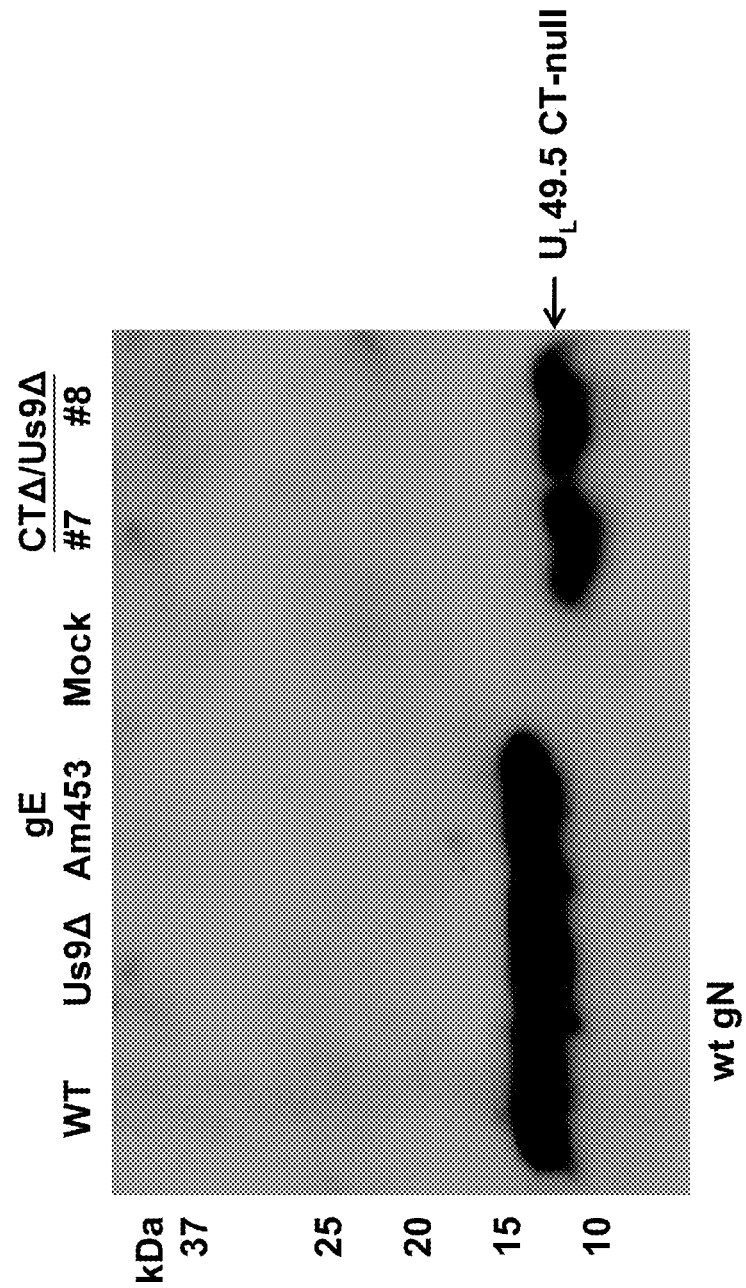
FIG. 24 illustrates the results of an immunoblotting analysis of $U_L49.5\Delta30$-32 CT-null expression in the mutant BHV-1 $U_L49.5\Delta30$-32 CT-null/gE CT$\Delta$/Us9$\Delta$ virus-infected MDBK cells. Uninfected (mock)-, BHV-1 wt-, BHV-1 gE Am453-(32), BHV-1 Us9$\Delta$- (34), and two putative BHV-1 $U_L49.5\Delta30$-32 CT-null/gE CT$\Delta$/Us9$\Delta$ mutant viruses (#7 and #8) infected cell lysates were separated by a 5-20% linear gradient SDS-PAGE and incubated with rabbit anti-BHV-1 $U_L49.5$ polyclonal Ab.

To further verify the $U_L49.5\Delta30$-32 CT-null expressed by the BHV-1 $U_L49.5\Delta30$-32 CT-null/gE CT$\Delta$/Us9$\Delta$ putative recombinant viruses, immuno-blotting analyses were performed. FIG. 24 shows the results of an immunoblotting analysis of $U_L49.5\Delta30$-32 CT-null expression in the mutant BHV-1 $U_L49.5\Delta30$-32 CT-null/gE CT$\Delta$/Us9$\Delta$ virus-infected MDBK cells. Uninfected (mock)-, BHV-1 wt-, BHV-1 gE Am453-, BHV-1 Us9$\Delta$-, and two putative BHV-1 $U_L49.5\Delta30$-32 CT-null/gE CT$\Delta$/Us9$\Delta$ mutant viruses (#7 and #8) infected cell lysates were separated by a 5-20% linear gradient SDS-PAGE and incubated with rabbit anti-BHV-1 $U_L49.5$ polyclonal Ab. The BHV-1 gE Am453 was made as previously described [32], and is mutated such that a stop codon prevents the expression of the CT tail in the protein. As shown in FIG. 24, both the putative recombinant viruses (#7 and #8) depicted a slightly smaller $U_L49.5$ band relative to wt $U_L49.5$ in BHV-1 wt, BHV-1 Us9-deleted (control) and BHV-1 gEAm453 (CT truncated control) virus-infected cell lystes. BHV-1 $U_L49.5\Delta30$-32 CT-null/gE CT$\Delta$/Us9$\Delta$ mutant virus was shown to have a $U_L49.5$ of approximately 8 kDa, which is consistent with the predicted molecular mass of $U_L49.5$ lacking the cytoplasmic tail residues.

Figure 25:
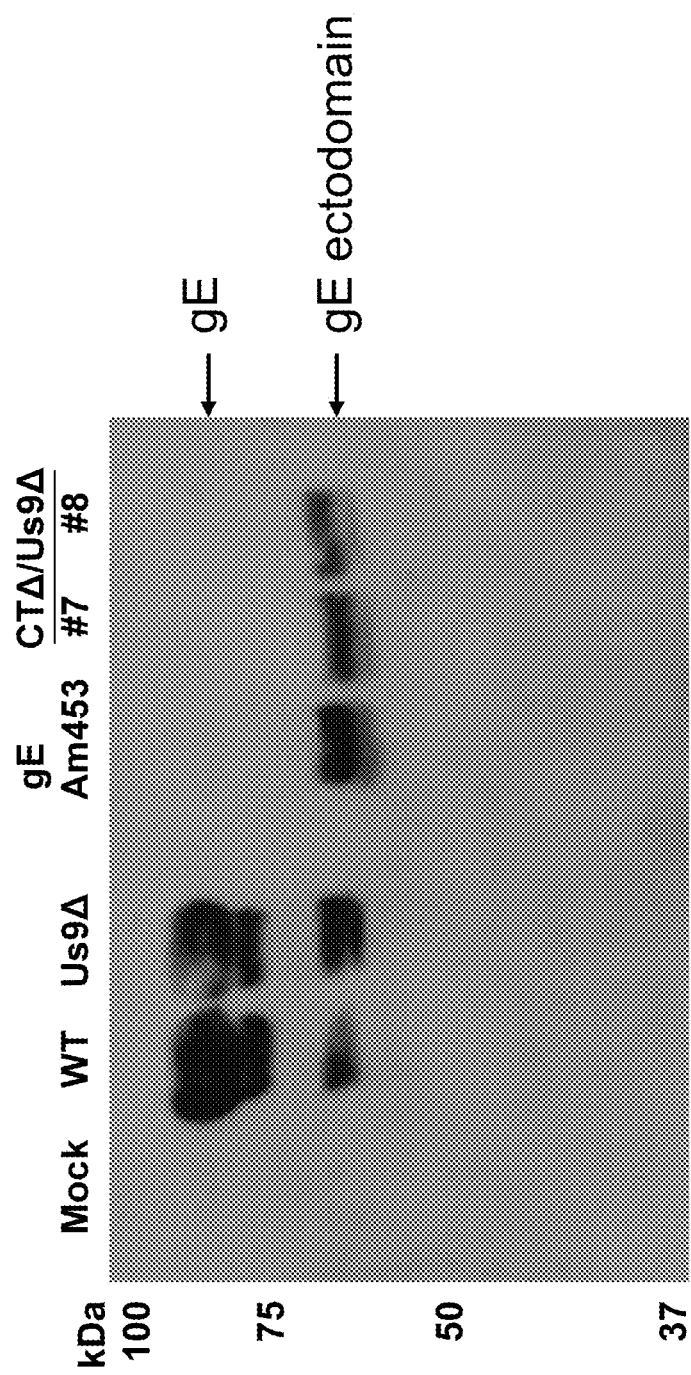
FIG. 25 illustrates the results of an immunoblotting analysis of BHV-1 $U_L49.5$ A30-32 CT-null/gE CT$\Delta$/Us9$\Delta$ showing the mutant gE (CT$\Delta$) incorporation in the virion envelope. Partially purified virions of BHV-1 wt, BHV-1 gE Am453, BHV-1 Us9$\Delta$, and two putative BHV-1 $U_L49.5\Delta30$-32 CT-null/gE CT $\Delta$/Us9 $\Delta$ mutant viruses (#7 and #8) were separated by a 10% SDS-PAGE and incubated with rabbit anti-BHV-1 gE peptide-specific polyclonal antibody.

FIG. 25 shows the results of an immunoblotting analysis of BHV-1 $U_L49.5\Delta30$-32 CT-null/gE CT$\Delta$/Us9$\Delta$ showing mutant gE (CT$\Delta$) incorporation in the virion envelope. Partially purified virions of BHV-1 wt, BHV-1 gE Am453, BHV-1 Us9$\Delta$, and two putative BHV-1 $U_L49.5\Delta30$-32 CT-null/gE CT$\Delta$/Us9$\Delta$ mutant viruses (#7 and #8) were separated by a 10% SDS-PAGE and incubated with rabbit anti-BHV-1 gE peptide-specific polyclonal antibody. BHV-1 $U_L49.5\Delta30$-32 CT-null/gE CT$\Delta$/Us9$\Delta$ mutant virus has a gE of approximately 65 kDa and is similar to BHV-1 gE Am453 virus, which is consistent with the predicted molecular mass of gE lacking the cytoplasmic tail residues. In contrast, the wt gE expressed by the BHV-1 wt and BHV-1 Us9$\Delta$ viruses was about 92 kD. Also, shown in FIG. 25 for WT and Us9$\Delta$, are bands at about 65 kD which represents unprocessed gE.

Figure 26:
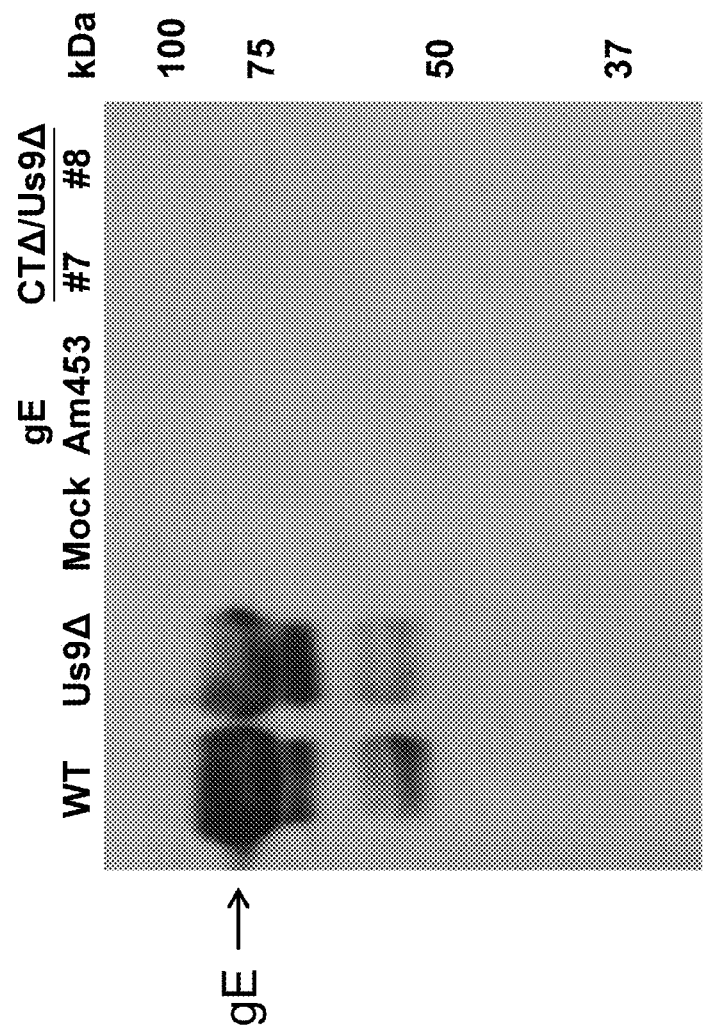
FIG. 26 illustrates the results of an immunoblotting analysis of BHV-1 $U_L49.5\Delta30$-32 CT-null/gE CT$\Delta$/Us9$\Delta$ showing the mutant gE (CT$\Delta$) incorporation in the virion envelope. Partially purified virions of BHV-1 wt, BHV-1 gE Am453, BHV-1 Us9$\Delta$, and two putative BHV-1 $U_L49.5\Delta30$-32 CT-null/gE CT$\Delta$/Us9$\Delta$ mutant viruses (#7 and #8) were separated by a 10% SDS-PAGE and incubated with rabbit anti-BHV-1 gE CT-specific antibody.

FIG. 26 illustrates the results of an immunoblotting analysis of the same cell lysates as in FIG. 25, but using rabbit anti-BHV-1 gE CT-specific antibody for incubation. A 92 kD, gE-specific band is detectable in BHV-1 wt and BHV-1 Us9$\Delta$ infected cell lysates, but not in cases of BHV-1 gE Am453 and BHV-1 $U_L49.5\Delta30$-32 CT-null/gE CT$\Delta$/Us9$\Delta$ mutant virus. The 68 kD band recognized by gE ectodomain-specific antibody in FIG. 25 was absent in the BHV-1 gEAm453, recombinant #7 and #8 lysates. Therefore, the gE CT-specific amino acids were deleted in the case of both the putative recombinant viruses #7 and #8, however, they both expressed the gE ectodomain and the gE transmembrane domain residues (FIG. 25).

Figure 27:
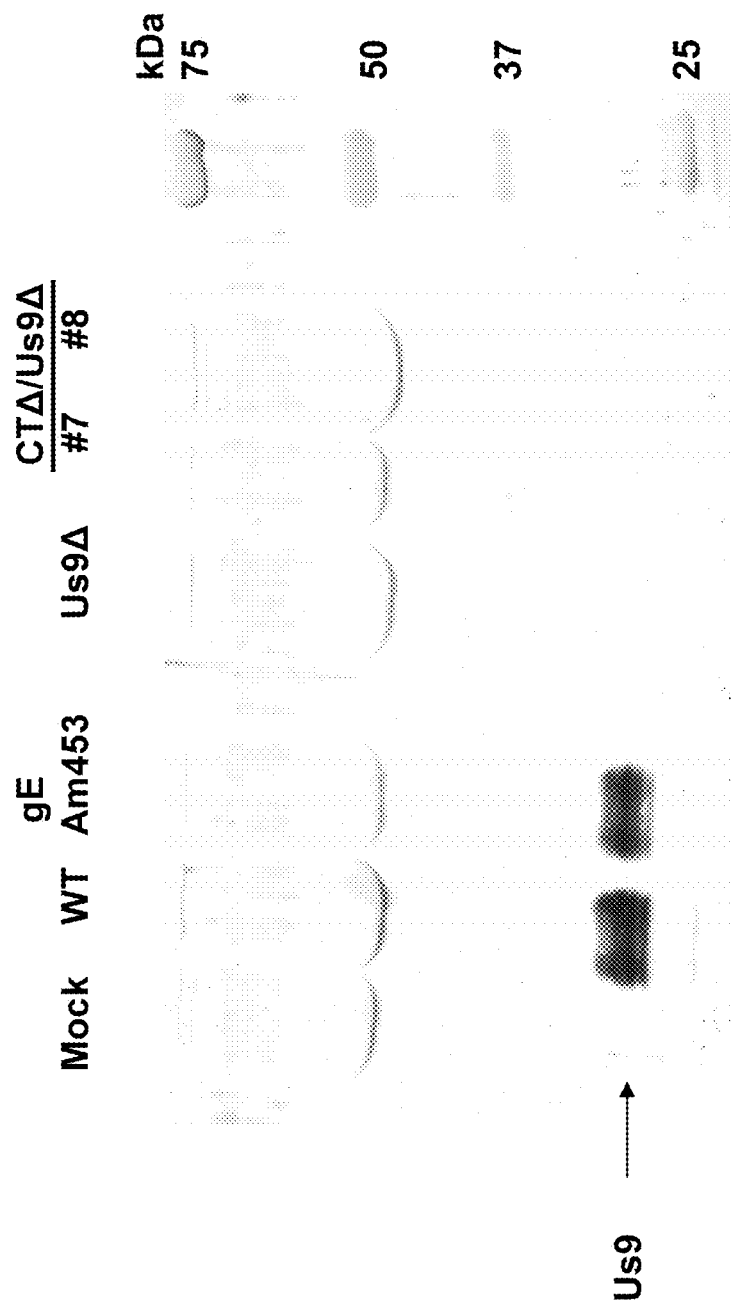
FIG. 27 illustrates the results of an immunoblotting analysis showing the deletion of Us9 in the BHV-1 $U_L49.5\Delta30$-32 CT-null/gE CT$\Delta$/Us9$\Delta$ mutant virus. Uninfected (mock)-, BHV-1 wt-, BHV-1 gE Am453-, BHV-1 Us9$\Delta$-, and two putative BHV-1 $U_L49.5\Delta30$-32 CT-null/gE CT$\Delta$/Us9$\Delta$ mutant viruses (#7 and #8) infected cell lysates were separated by a 10% SDS-PAGE and incubated with rabbit anti-BHV-1 Us9-specific polyclonal serum.

FIG. 27 shows the results of an immunoblotting analysis showing the same cell lysates as above but incubating with rabbit anti-BHV-1 Us9-specific polyclonal serum. A 28 kDa Us9 specific band is detectable in BHV-1 wt and BHV-1 gE Am453 infected cell lysates, but as expected not seen in BHV-1 Us9$\Delta$ and BHV-1 $U_L49.5\Delta30$-32 CT-null/gE CT$\Delta$/Us9$\Delta$ mutant virus. Therefore, the entire Us9 coding region was deleted in the putative recombinants #7 and #8.

Figure 28:
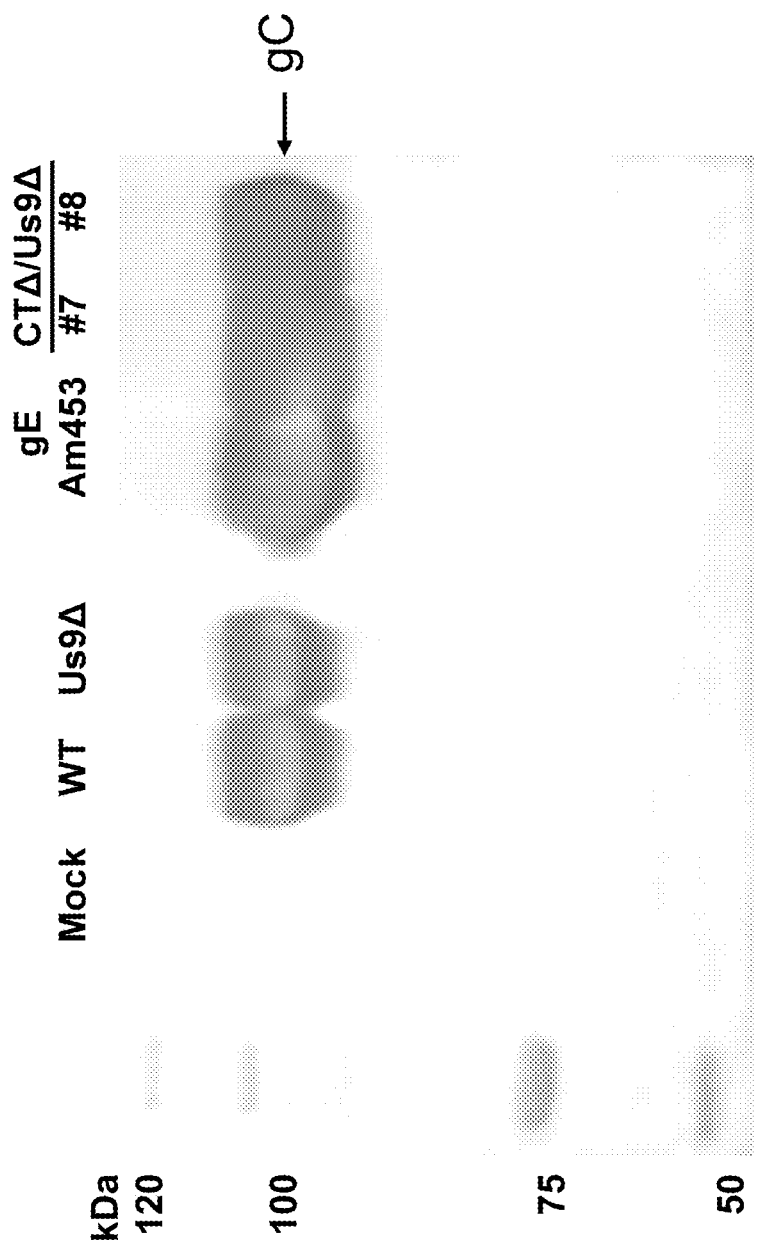
FIG. 28 illustrates the results of an immunoblotting analysis of BHV-1 gC in the BHV-1 $U_L49.5\Delta30$-32 CT-null/gE CT$\Delta$/Us9$\Delta$ mutant virus-infected MDBK cells. Uninfected (mock)-, BHV-1 wt-, and two putative BHV-1 $U_L49.5\Delta30$-32 CT-null/gE CT$\Delta$/Us9$\Delta$ mutant viruses (#7 and #8) infected cell lysates were separated by a 10% SDS-PAGE and incubated with mouse anti-BHV-1 gC-specific McAb.

When the same lysates were immunoblotted with mouse anti-BHV-1 envelope glycoprotein gC-specific MAb F2 (Chowdhury et al., 2000), as shown in FIG. 28, similar amounts of gC were detected for all the viruses. Taken together with these results, the absence of Us9-specific (FIG. 27) and of gE cytoplasmic-tail specific (FIG. 26) bands in the respective immunoblots were due to specific deletions and not due to loading errors.

Example 11

Stability of BHV-1 $U_L49.5\Delta30$-32 CT-Null/gE CT$\Delta$/Us9$\Delta$ Virus Upon Five Consecutive Passages To determine the stability of specific $U_L49.5$, gE CT and Us9 mutations and/or deletions, one of the putative recombinants (#7) was selected for serial passages in MDBK cells. Virus-infected cell DNA was then extracted from passage 0 (P0; original stock), after three passages (P3), and after five passages (P5). The virus-infected cell DNA was then used for PCR amplification and for verification using $U_L49.5$ ORF-specific and/or gE-bICP22-specific primer pairs as shown in FIG. 29A and as listed in Table 3. FIG. 29B shows the results of PCR amplification of the BHV-1 $U_L49.5\Delta30$-32 CT-null/gE CTΔ/Us9Δ virus DNA at passage 0 (P0), three serial passages (P3), and five serial passages (P5) using the $U_L49.5$-specific primer pair of $U_L49.5$-1/$U_L49.5$-2 as shown in Table 3 and FIG. 29A. FIG. 29C shows the results of PCR amplification of the BHV-1 $U_L49.5\Delta30$-32 CT-null/gE CTΔ/Us9Δ virus DNA at passage 0 (P0), three serial passages (P3), and five serial passages (P5) using the gE-ICP22 prim TABLE 3-continued List of primers used for identification BHV-1 U$_L$49.5Δ30-32CT-null/gE CTΔ/Us9Δ recombinant virus and verification deleted and/or mutated sequences stability

| Gene | Name | Primer sequences | Expected PCR size | Sequencing analysis |
|---|---|---|---|---|
| | NO: 28 P8 (Rev) SEQ ID NO: 29 | AJ004801.1)) gtagcggaggatggacttgagtcgc (complementary gE NT 1704-1728, FIG. 4; based on GenBank Accession No. AJ004801.1)) | | negative |
| gE-ICP22 | P9 SEQ ID NO: 30 P10 SEQ ID NO: 31 | caggcccaccgctcaccagcgag (gE NT 1214-1236, FIG. 4; based on GenBank Accession No. AJ004801.1)) gagccggagctttggcccgctcgct (complementary to BICP22 NT 2658-2683, FIG. 4; based on GenBank Accession No. AJ004801.1)) | WT: 1350 bp Mutant: 400bp | Yes |
| Us9 | P11 (For) SEQ ID NO: 32 P12 (Rev) SEQ ID NO: 33 | atggagagtccacgcagcgtcgtc (NT 1835-1858, FIG. 4; based on GenBank Accession No. AJ004801.1)) gaagacaggcgcgggcgtgcgga (complementary to NT 2369-2391, FIG. 4; based on GenBank Accession No. AJ004801.1)) | WT: 550 bp Mutant: negative | |

Example 12

In Vivo Characterization of the Virus in Rabbits and in Calves: Determination of In Vivo Intra Nasal Replication/Shedding Property in

[12] Gopinath R S, Ambagala A P, Hinkley S, Srikumaran S. Effects of virion host shut-off activity of bovine herpesvirus 1 on MHC class I expression. Viral Immunol 2002; 15(4):595-608.

[13] Koppers-Lalic D, Rijsewijk F A, Verschuren S B, van Gaans-Van den Brink J A, Neisig A, Ressing M E, et al. The UL41-encoded virion host shutoff (vhs) protein and vhs-independent mechanisms are responsible for down-regulation of MHC class I molecules by bovine herpesvirus 1. J Gen Virol 2001; 82(Pt 9):2071-81.

[14] Hewitt E W. The MHC class I antigen presentation pathway: strategies for viral immune evasion. Immunology 2003; 110(2):163-9.

[15] Koppers-Lalic D, Verweij M C, Lipinska A D, Wang Y, Quinten E, Reits E A, et al. Varicellovirus UL 49.5 proteins differentially affect the function of the transporter associated with antigen processing, TAP. PLoS Pathog 2008; 4(5):e1000080.

[16] van Drunen Littel-van den Hurk S, Tikoo S K, Liang X, Babiuk L A. Bovine herpesvirus-1 vaccines. Immunol Cell Biol 1993; 71 (Pt 5):405-20.

[17] van Drunen Littel-van den Hurk S, Tikoo S K, van den Hurk J V, Babiuk L A, Van Donkersgoed J. Protective immunity in cattle following vaccination with conventional and marker bovine herpesvirus-1 (BHV1) vaccines. Vaccine 1997; 15(1):36-44.

[18] Harland R J, Potter A A, van Drunen-Littel-van den Hurk S, Van Donkersgoed J, Parker M D, Zamb T J, et al. The effect of subunit or modified live bovine herpesvirus-1 vaccines on the efficacy of a recombinant Pasteurella haemolytica vaccine for the prevention of respiratory disease in feedlot calves. Can Vet J 1992; 33(11):734-41.

[19] van Oirschot J T, Kaashoek M J, Rijsewijk F A. Advances in the development and evaluation of bovine herpesvirus 1 vaccines. Vet Microbiol 1996; 53(1-2):43-54.

[20] Jons A, Dijkstra J M, Mettenleiter T C. Glycoproteins M and N of pseudorabies virus form a disulfide-linked complex. J Virol 1998; 72(1):550-7.

[21] Rudolph J, Seyboldt C, Granzow H, Osterrieder N. The gene 10 (UL49.5) product of equine herpesvirus 1 is necessary and sufficient for functional processing of glycoprotein M. J Virol 2002; 76(6):2952-63.

[22] Wu S X, Zhu X P, Letchworth G J. Bovine herpesvirus 1 glycoprotein M forms a disulfide-linked heterodimer with the U(L)49.5 protein. J Virol 1998; 72(4):3029-36.

[23] Liang X, Chow B, Raggo C, Babiuk L A. Bovine herpesvirus 1 UL49.5 homolog gene encodes a novel viral envelope protein that forms a disulfide-linked complex with a second virion structural protein. J Virol 1996; 70(3):1448-54.

[24] Loch S, Klauschies F, Scholz C, Verweij M C, Wiertz E J, Koch J, et al. Signaling of a varicelloviral factor across the endoplasmic reticulum membrane induces destruction of the peptide-loading complex and immune evasion. J Biol Chem 2008; 283(19):13428-36.

[25] Chowdhury S I. Construction and characterization of an attenuated bovine herpesvirus type 1 (BHV-1) recombinant virus. Vet Microbiol 1996; 52(1-2):13-23.

[26] Konig P, Giesow K, Keil G M. Glycoprotein M of bovine herpesvirus 1 (BHV-1) is nonessential for replication in cell culture and is involved in inhibition of bovine respiratory syncytial virus F protein induced syncytium formation in recombinant BHV-1 infected cells. Vet Microbiol 2002; 86(1-2):37-49.

[27] Chowdhury S I, Mahmood S, Simon J, Al-Mubarak A, Zhou Y. The Us9 gene of bovine herpesvirus 1 (BHV-1) effectively complements a Us9-null strain of BHV-5 for anterograde transport, neurovirulence, and neuroinvasiveness in a rabbit model. J Virol 2006; 80(9):4396-405.

[28] Chowdhury S I, Lee B J, Ozkul A, Weiss M L. Bovine herpesvirus 5 glycoprotein E is important for neuroinvasiveness and neurovirulence in the olfactory pathway of the rabbit. J Virol 2000; 74(5):2094-106.

[29] Al-Mubarak A, Zhou Y, Chowdhury S I. A glycine-rich bovine herpesvirus 5 (BHV-5) gE-specific epitope within the ectodomain is important for BHV-5 neurovirulence. J Virol 2004; 78(9):4806-16.

[30] Tischer B K, von Einem J, Kaufer B, Osterrieder N. Two-step red-mediated recombination for versatile high-efficiency markerless DNA manipulation in *Escherichia coli*. Biotechniques 2006; 40(2): 191-7.

[31] Smith G A, Enquist L W. A self-recombining bacterial artificial chromosome and its application for analysis of herpesvirus pathogenesis. Proc Natl Acad Sci USA 2000; 97(9):4873-8.

[32] Liu Z F, Brum M C, Doster A, Jones C, Chowdhury S I. A bovine herpesvirus type 1 mutant virus specifying a carboxyl-terminal truncation of glycoprotein E is defective in anterograde neuronal transport in rabbits and calves. J Virol 2008; 82(15):7432-42.

[33] Chowdhury S I, Ross C S, Lee B J, Hall V, Chu H J. Construction and characterization of a glycoprotein E gene-deleted bovine herpesvirus type 1 recombinant. Am J Vet Res 1999; 60(2):227-32.

[34] Hinkley S, Hill A B, Srikumaran S. Bovine herpesvirus-1 infection affects the peptide transport activity in bovine cells. Virus Res 1998; 53(1):91-6.

[35] Wei H, Huang D, Lai X, Chen M, Zhong W, Wang R, et al. Definition of APC presentation of phosphoantigen (E)-4-hydroxy-3-methyl-but-2-enyl pyrophosphate to Vgamma2Vdelta 2 TCR. J Immunol 2008; 181(7):4798-806.

[36] Chowdhury, S. I., Coates, C J., Neis, R A., Navarro, S M., Paulsen, D B. And Feng, J-M. (2010). A Bovine Herpesvirus Type 1 (BHV-1) mutant virus with truncated glycoprotein E cytoplasmic tail has defective anterograde neuronal transport in rabbit dorsal root ganglionic primary neuronal cultures in a microfluidic chamber system. J. Neurovirol. 17:457-465.

[37] Kaashoek, M. J., F. A. M. Fijsewijk, R. C. Ruuls, G. M. Keil, E. Thiry, P. P. Pastoret, and J. T. Van Oirschot. (1998) Virulence, immunogenicity and reactivation of bovine herpesvirus 1 mutants with a deletion in the gC, gG, gI, gE, or in both the gI and gE gene. Vaccine. 16: 802-809.

[38] Kaashoek, M. J., F. A. C. van Engelenburg, A. Moerman, A. L. J. Gielkens, F. A. M. Fijsewijk, and J. T. van Oirschot (1996). Virulence and immunogenicity in calves of thymidine kinase- and glycoprotein E-negative bovine herpesvirus 1 mutants. Vet Microbiol. 48:143-153.

[39] Whitbeck, J. C., A. C. Knapp, L. W. Enquist, W. C. Lawrence, and L. J. Bello (1996). Synthesis, processing, and oligomerization of the bovine herpes virus 1 gE and gI membrane proteins. J Virol. 70: 7878-7884.

[40] Chowdhury, S I, M. C. S. Brum, C. Coats, A. Doster, and C. Jones (2011) "A bovine hervesvirus type 1 envelope protein Us9 acidic domain is crucial for anterograde axonal transport," Vet. Microbiol., epub ahead of print, May 13, 2011.

[41] Mars M H, de Jong M C, Franken P, van Oirschot J T (2001). Efficacy of a live glycoprotein E-negative bovine herpesvirus 1 vaccine in cattle in the field. Vaccine. 19:1924-30.

[42] Muylkens B, Meurens F, Schynts F, Farnir F, Pourchet A, Bardiau M, et al (2006). Intraspecific bovine herpesvirus 1 recombinants carrying glycoprotein E deletion as a vaccine marker are virulent in cattle. J Gen Virol. 87:2149-54.

[43] Butchi N B, Jones C, Perez S, Doster A, Chowdhury S I (2007). Envelope protein Us9 is required for the anterograde transport of bovine herpesvirus type 1 from trigeminal ganglia to nose and eye upon reactivation. J. Neurovirol. 3:384-388.

[44] Hutchings D L, van Drunen Littel-van den Hurk S, Babiuk L A (1990). Lymphocyte proliferative responses to separated bovine herpesvirus 1 proteins in immune cattle. J. Virol. 64:5114-22.

[45] Wei H, Huang D, Fortman J, Wang R, Shao L, Chen Z W (2009). Coadministration of cidofovir and smallpox vaccine reduced vaccination side effects but interfered with vaccine-elicited immune responses and immunity to monkeypox. J. Virol. 83:1115-25.

[46] Wei H, Wang R, Yuan Z, Chen C Y, Huang D, Halliday L, et al (2009). DR*W201/P65 tetramer visualization of epitope-specific CD4 T-cell during *M. tuberculosis* infection and its resting memory pool after BCG vaccination. PLoS One. 4(9):e6905.

The complete disclosures of all references cited in this specification are hereby incorporated by reference. Also incorporated by reference is the complete disclosure of Huiyoung Wei, Ying Wang, and S. I. Chowdhury, "Bovine herpesvirus type 1 (BHV-1) $U_L49.5$ luminal domain residues 30 to 32 are critical for MHC-1 down-regulation in virus-infected cells," PLoS ONE, vol. 6(10):e25742, Oct. 26, 2011. In the event of an otherwise irreconcilable conflict, however, the present specification shall control.

We claim:

1. A bovine herpesvirus-1 (BHV-1) mutant virus comprising at least two deletion mutations, wherein the gene encoding UL49.5 (glycoprotein N) is only mutated by deleting nucleotides encoding amino acid residues 30 to 32 and 80 to 96 according to SEQ ID NO: 34.

2. The BHV-1 mutant virus of claim 1, further comprising one or more mutations in one or more genes selected from the group consisting of the gene encoding glycoprotein E and the gene encoding envelope protein Us9.

3. The BHV-1 mutant virus of claim 1, further comprising a deletion in the cytoplasmic tail region of the gene encoding glycoprotein E.

4. The BHV-1 mutant virus of claim 1, further comprising one or more deletions in the gene encoding the envelope protein Us9; wherein at least one said deletion is selected from the group consisting of the deletion of the entire Us9 gene; and a deletion of nucleotides of the Us9 gene encoding residues of the acidic region of the cytoplasmic tail region, said nucleotides encoding residues of the acidic region of the cytoplasmic tail region being nucleotides corresponding to those numbered from about 2068 to about 2128 in SEQ ID NO:42.

5. The BHV-1 mutant virus of claim 4, wherein said one or more deletions comprise a deletion of the nucleotides corresponding to those numbered from about 2081 to about 2104 in SEQ ID NO:42.

6. The BHV-1 mutant virus of claim 1, further comprising one or more deletions in the gene encoding envelope protein Us9, wherein said one or more deletions cause a truncation of all or part of the residues of the cytoplasmic tail region of Us9.

7. A bovine herpesvirus-1 (BHV-1) mutant virus, wherein said mutant virus contains at least three deletion mutations: wherein the first said deletion mutation comprises only one mutation in the gene that encodes UL49.5, wherein said mutation is the deletion of only the nucleotides that encode the UL49.5 amino acid residues numbered from 30 to 32 according to SEQ ID NO:34, wherein the second said deletion mutation is that the nucleotides are deleted that encode at least part of the cytoplasmic tail region of glycoprotein E, and wherein the third said deletion mutation is selected from the group consisting of the deletion of all nucleotides that encode for envelope protein Us9 or deletion of nucleotides 2068 to 2128 according to SEQ ID NO:42 which encode for amino acids 83-90 of Us9.

8. A live attenuated vaccine for protection against BHV-1 infection comprising the BHV-1 mutant virus of claim 1 or claim 7.

9. A vaccine composition, comprising the vaccine of claim 8 and a pharmaceutically acceptable vehicle or adjuvant.

10. A method of immunizing cattle against a BHV-1 infection, said method comprising inoculating the cattle with the vaccine of claim 8.

11. A vector comprising the BHV-1 mutant virus of claim 1 or claim 7 and one or more exogenous genes.

* * * * *